US012588955B2

(12) United States Patent
Lonjaret et al.

(10) Patent No.: US 12,588,955 B2
(45) Date of Patent: Mar. 31, 2026

(54) COMPUTER-ASSISTED SURGERY SYSTEM

(71) Applicant: MINMAXMEDICAL, Saint-Martin-d'Hères (FR)

(72) Inventors: Thomas Lonjaret, Saint-Martin-d'Heres (FR); Elie Fournier, Saint-Martin-d'Heres (FR); Christophe Dehan, Saint-Martin-d'Heres (FR); Stéphane Lavallée, Saint-Martin-d'Heres (FR); Sébastien Camet, Saint-Martin-d'Heres (FR); Sylvain Fontaine, Saint-Martin-d'Heres (FR); Jérémy Quintin, Saint-Martin-d'Heres (FR)

(73) Assignee: MINMAXMEDICAL, Saint Martin d'Heres (FR)

( * ) Notice: Subject to any disclaimer, the term of this patent is extended or adjusted under 35 U.S.C. 154(b) by 253 days.

(21) Appl. No.: 17/962,020

(22) Filed: Oct. 7, 2022

(65) Prior Publication Data

US 2023/0085725 A1     Mar. 23, 2023

Related U.S. Application Data

(63) Continuation-in-part of application No. PCT/EP2022/059540, filed on Apr. 8, 2022.

(30) Foreign Application Priority Data

Apr. 9, 2021     (EP) .................................... 21305465

(51) Int. Cl.
| | |
|---|---|
| *A61B 34/30* | (2016.01) |
| *A61B 34/00* | (2016.01) |
| *A61B 34/10* | (2016.01) |

(52) U.S. Cl.
CPC .............. *A61B 34/30* (2016.02); *A61B 34/10* (2016.02); *A61B 34/25* (2016.02);
(Continued)

(58) Field of Classification Search
CPC ......... A61B 34/10; A61B 34/20; A61B 34/25; A61B 34/30; A61B 34/74; A61B 34/75;
(Continued)

(56)     References Cited

U.S. PATENT DOCUMENTS

| | | |
|---|---|---|
| 10,398,519 B2 | 9/2019 | Kim et al. |
| 10,813,704 B2 | 10/2020 | Kostrzewski et al. |

(Continued)

FOREIGN PATENT DOCUMENTS

| | | |
|---|---|---|
| DE | 3211992 A1 | 10/1983 |
| KR | 20200076172 A | 6/2020 |
| WO | 2007096322 A2 | 8/2007 |

OTHER PUBLICATIONS

PCT Written Opinion in related PCT Application No. PCT/EP2022/059540, mailed Jun. 2, 2022.

(Continued)

*Primary Examiner* — Jason Holloway
*Assistant Examiner* — Blake A Wood
(74) *Attorney, Agent, or Firm* — Thomas | Horstemeyer, LLP

(57)     ABSTRACT

A computer-assisted surgery system allows a user to control movements of a surgical tool by providing, to a control unit, inputs in the form of measured displacements via a movable part of a handle while treating a region of interest with the tool. The control unit is configured to enable motion of the tool with respect to an anatomical structure only if a user moves the movable part, receive the measured displacement of the movable part, receive from a localization unit the relative position and orientation of the tool relative to the (Continued)

anatomical structure, based on the measured displacement, on the surgical plan and on the relative position and orientation of the tool relative to the anatomical structure, compute an instruction to send to a motorized joint to move a robotic arm to operate the tool according to an optimal trajectory, and send the computed instruction to the motorized joint.

31 Claims, 23 Drawing Sheets

(52) U.S. Cl.
CPC ... *A61B 2034/107* (2016.02); *A61B 2034/252* (2016.02); *A61B 2034/305* (2016.02)

(58) Field of Classification Search
CPC ......... A61B 34/76; A61B 90/50; A61B 90/57; A61B 90/90; A61B 90/98; A61B 2017/0042; A61B 2017/00477; A61B 2017/00486; A61B 2034/101; A61B 2034/105; A61B 2034/107; A61B 2034/2055; A61B 2034/2065; A61B 2034/2074; A61B 2034/252; A61B 2034/254; A61B 2034/256; A61B 2034/305; A61B 2034/742; A61B 2090/064; A61B 2090/066; A61B 2090/08021; A61B 2090/0804; A61B 2090/0805; A61B 2090/0818; B25J 9/1676; B25J 13/02; G05B 19/0426; G05B 2219/2617; G05B 2219/45117

See application file for complete search history.

(56) References Cited

U.S. PATENT DOCUMENTS

| 2004/0128026 | A1 | 7/2004 | Harris | |
| 2018/0168759 | A1* | 6/2018 | Kilroy | B25J 13/086 |
| 2019/0231447 | A1* | 8/2019 | Ebbitt | A61F 2/46 |
| 2020/0281676 | A1* | 9/2020 | Rohs | A61B 34/10 |
| 2021/0068845 | A1* | 3/2021 | Schers | A61B 17/02 |
| 2021/0298795 | A1* | 9/2021 | Bowling | B25J 9/1689 |
| 2021/0298846 | A1* | 9/2021 | Dozeman | A61B 90/03 |

OTHER PUBLICATIONS

PCT Search Report in related PCT Application No. PCT/EP2022/059540 mailed Jun. 2, 2022.
European Search Report in related EP Application No. 21305466, mailed Sep. 29, 2021.
European Written Opinion in related EP Application No. 21305466, mailed Sep. 29, 2021.
Lavallée & P. Cinquin: "Computer assisted medical interventions" In K.H. Hohne, editor, NATO ARW, 30 Imaging in Medicine, vol. F60, 301-312, Berlin, Jun. 1990. Springer-Verlag.
"Semi-active guiding systems in surgery. A two-dof prototype of the passive arm with dynamic constraints (PADyC)" published in Mechatronics, vol. 6, Issue 4, Jun. 1996, pp. 399-421, written by Jocelyne Troccaz & Yves Delnondedieu, TIMC/IMAG Laboratory, Faculté de Médecine (IAB), Domaine de la Merci, 3, 38706 La Tronche Cedex, France.
R. A. MacLachlan, B. C. Becker, J. C. Tabares, G. W. Podnar, L. A. Lobes and C. N. Riviere, "Micron: An Actively Stabilized Handheld Tool for Microsurgery," in IEEE Transactions on Robotics, vol. 28, No. 1, pp. 195-212, Feb. 2012.

* cited by examiner

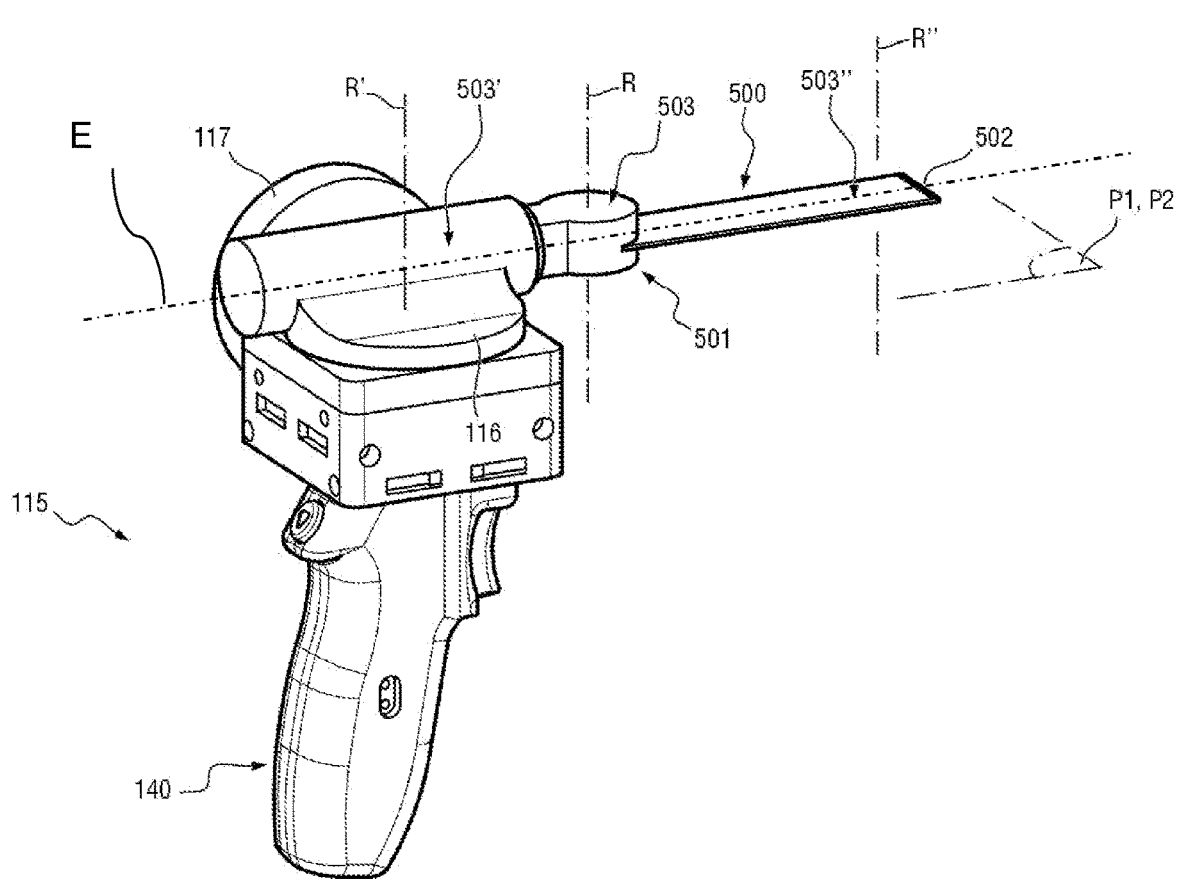
FIGURE 28
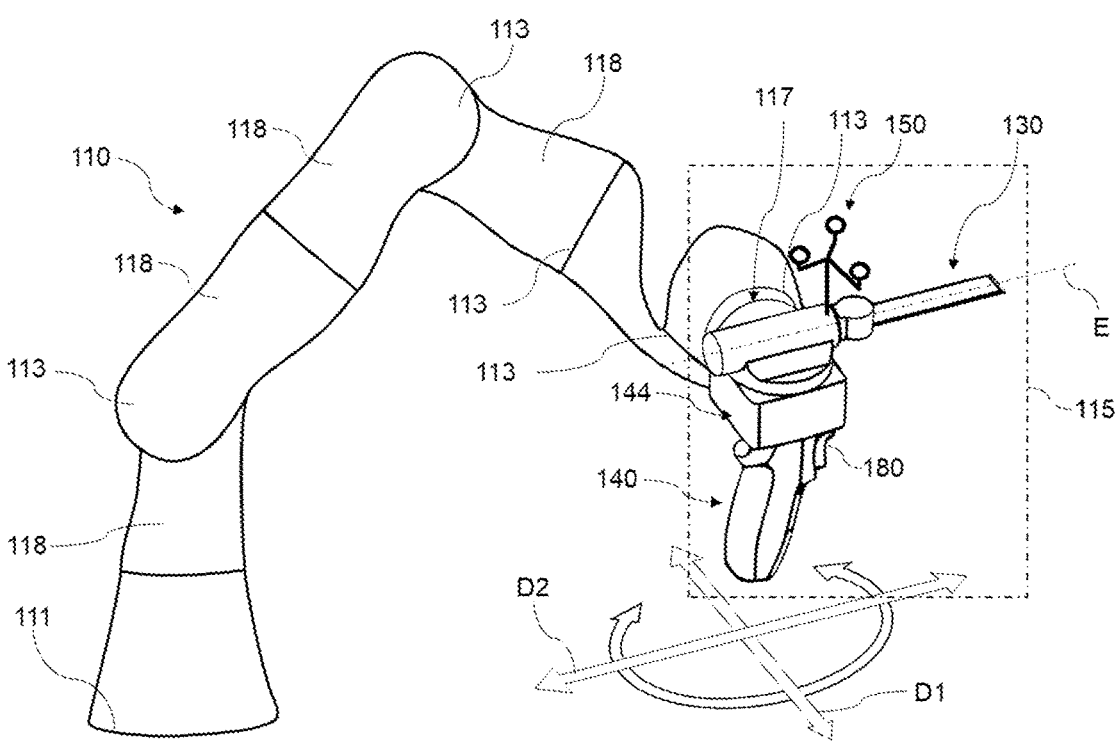
FIGURE 28bis

COMPUTER-ASSISTED SURGERY SYSTEM

CROSS REFERENCE TO RELATED APPLICATIONS

This application is a Continuation-in-Part Application of PCT Application No. PCT/EP2022/059540, filed Apr. 8, 2022, which application claims the benefit of European Application No. EP 21305465.3 filed Apr. 9, 2021, both of which are hereby incorporated by reference herein in their entireties.

TECHNICAL FIELD

The present invention concerns a computer-assisted surgery system which comprises a robotic arm to which a surgical tool is attached. Especially the invention relates to a computer-assisted surgery system dedicated to bone surgery. The operator of such computer-assisted surgery system is typically an orthopedic surgeon, a craniofacial surgeon, a dental surgeon an ENT surgeon or a neurosurgeon depending on the targeted anatomical structure.

BACKGROUND OF THE INVENTION

During the last few decades, the field of computer-assisted systems has significantly grown, and especially computer-assisted surgery systems which are adapted to be used in computer-assisted medical intervention (CAMI), as referred to in the publication of S. Lavallée & P. Cinquin: "*Computer assisted medical interventions*" In K. H. Hohne, editor, NATO ARW, 30 Imaging in Medicine, Vol F60, 301-312, Berlin, June 1990. Springer-Verlag. Such systems aim to help surgeons in performing safer surgical treatments while also improving the accuracy, precision and reproducibility of said treatments. The use of those computer-assisted surgery systems also aims at improving the precision of surgical actions, also lowering invasiveness during those treatments.

Robotic aid to clinicians for the execution of optimal surgery was introduced in the early 1980's in neurosurgery application. Since the 1990's, several assistive technologies combining part or all of 2D/3D imaging, navigation and robotics were developed with the primary focus of improving accuracy of surgical procedures, in view of improving clinical and functional outcomes for the patients.

A first generation of robots were developed as passive-robots. These passive-robots can for example consist of optical localizer or motorless encoded arms and they are particularly well-suited for surgical navigation, but their use is difficult for executing complex surgical strategies. However, these passive-robots can be useful for performing simple surgical treatment such as ones wherein the movements needed are all about one single axis. For instance, the robot Cirq® developed by BrainLab is one of those passive robots.

A second generation of robots were developed as active robots. These active robots are designed to perform at least part of an intervention on their own from a planned procedure, i.e., without any real-time guidance from the surgeon, nor from any other operator. For instance, Robodoc® is an active robot developed by Integrated Surgical Systems, commercialized at the end of the 90's and adapted to perform part of hip replacements surgeries. Such active robots are generally accurate but raise safety and ergonomics concerns.

Nowadays, many medical device suppliers are developing collaborative robots, i.e., robots with which the operators are able to cooperate. Several technologies have been developed to create those collaborative robots, five of them being described below.

A first kind of collaborative robot uses embedded force or torque sensors, most of the time located in an end-effector of the robotic arm, to detect a force or torque applied by an operator, thanks to a controller and the computer-assisted system is then adapted to transform such detected force or torque into a movement of the robotic arm and of any surgical tool attached to said arm. An example of such a robot is for instance the robot ROSA developed by MedTech, today belonging to ZIMMER. Part of such robot ROSA is for instance described in French patent FR2917598B1. One drawback of this kind of robot control is that it is necessary for the operator to exert a force that is transferred to the robot and then compensated by a servo control of the robot, which may lead to inaccurate or lagging motions of the robot, especially when fine and delicate motions are necessary. This drawback is shared by all the systems which include force or torque sensors. Also, the force or torque sensors may detect movements which are not willingly applied on the controller by the operator, resulting in instructing a biased movement to the robotic arm and/or to the associated surgical tool. One other drawback of using such force or torque sensors is that they tend to drift. In other words, a neutral position of such force or torque sensors must be re-calibrated regularly.

A second kind of collaborative robot is designed to detect a force applied directly, by the operator, on one or many of the robotic arm segment(s) and to lean into such movement. For instance, the robotic arm can comprise at least one torque sensor arranged in each of its joints, such torque sensor being adapted to detect a torque applied to the robotic arm and to then drive the actuators of said joints in the sensed torque directions. Stick and slip joint actuation friction effects, as well as torque sensing threshold hamper transparency and smoothness of collaborative movement. Additionally, the joint torque sensors tend to reduce the robot stiffness. Alternately, the robotic arm can be adapted to return to a predefined position after being assigned to a movement by the operator, the movement applied thus being measured based on the current needed for the robotic arm to return to said predefined position. An example of such second kind of collaborative robot is the KUKA LBR Med robot. Unfortunately, those robots are not sufficiently accurate nor sufficiently sensitive to be used for complex surgeries, as they lack stiffness when needed and display a large feedback latency. By nature, such robots always react with annoying lag time, resulting in precision loss.

As described below, the present invention provides another kind of controller which is more accurate and more sensitive than the controller using torque sensors to achieve precise trajectories.

A third kind of collaborative robot is designed to provide kind of a boundary reactive feedback to the operator. Those robots are designed based on the use of dynamic constraints and they can be referred to as "reactive robots". The passive arm is physically displaced by the operator who keeps, therefore, fully involved in the execution of the surgical treatment. At each instant, the motions initiated by the operator are "filtered" with respect to the planned treatment, before being transmitted to the robotic arm and a reactive force is provided by the robot to counter the initial force applied by the operator on the robotic arm, in order to maintain the arm in a predetermined volume. One example of such a "Passive Arm with Dynamic Constraints" (PADyC) is described in an article published in *Mechatronics, Volume 6, Issue* 4, June 1996, Pages 399-421, written by JocelyneTroccaz & Yves Delnondedieu, *TIMC/IMAG Laboratory, Faculté de Médecine* (*IAB*), Domaine de la Merci, 3, 38706 La Tronche Cedex, France. Another example of a reactive robot is the so-called haptic robot developed by Mako Surgical, now a company of Stryker.

In any of those three kinds of collaborative robots, the operator directly moves the surgical tool itself and the robot reacts to the forces or motions of the surgical tool to constraint the surgical tool to some predefined rules or areas. It has the advantage of letting the operator quite free of trajectory and velocity. It has the disadvantage of adding inertia, as well as that some portion of the robot load capacity is used to compensate non desired motions exerted by the operator. Such reaction is also exerted with some latency, which can easily result in overshooting of targeted boundaries.

In a fourth kind of collaborative robots, the surgical tool is mounted on a planar passive articulated device, itself mounted on an active robot such that the user can freely move the surgical tool in a plane positioned by the robot, such as for saw bone cuts. An example of this technology is the Velys robot for knee surgery of Johnson & Johnson. It has the disadvantage that the surgical tool is not prevented from reaching forbidden areas since it is totally free, in said positioned plane.

A fifth kind of collaborative robot is designed as a tele-operable robot. This kind of robots are operated thanks to a remote control placed in a master console, distant from the slave robot itself, and can be referred to as "master-slave systems". For this kind of robots, the movement applied, from a distance, on the remote control are transmitted, as such, to the robotic arm and, consequently, to any surgical tool attached to said robotic arm. One example of such tele-operable robot is the DaVinci robot commercialized by Intuitive Surgical used for soft tissue surgeries, with visual control from the operator. Many variations of this model have been proposed for surgical robots, including the introduction of force feedback in the master control. These robots are not suitable for performing tasks such as drilling and sawing on bones since the surgeon is not in direct contact with the surgical field where many additional tasks are necessary.

It is also possible to use a robotic arm attached to a compact or miniature base, said base being held by the operator, and said base containing actuators that drive a surgical tool fixed to the robotic arm. One example of such computer-assisted surgery system is the Navio of Smith Nephew wherein the actuator has only one degree of freedom. Another example is described in the European patent EP3007636B1 which describes a robot wherein the actuators have three degrees of freedom and are adapted to drive a spherical burr. Those systems have the disadvantage that the user must hold the base of the robot, which may induce some fatigue. The use of such systems thus usually necessitates a support function to offer some rest to the operator, which in turn generates constraints. Some small robots have been developed also to react and compensate shakiness, but they need to be held in hands which is not stable and does offer a rest position. An example of such robot is for instance described in R. A. MacLachlan, B. C. Becker, J. C. Tabares, G. W. Podnar, L. A. Lobes and C. N. Riviere, "Micron: An Actively Stabilized Handheld Tool for Microsurgery," in IEEE Transactions on Robotics, vol. 28, no. 1, pp. 195-212, February 2012.

Finally, the U.S. Pat. No. 9,084,613B2 describes an active robot which can be switched to be used manually. The active robot described in said patent is adapted to perform, autonomously and based on pre-planned cutting instructions, at least part of a cutting surgery. If needed, the operator of the robot can set such robot in a manual mode, provided that he/she records manual cutting boundaries beforehand to limit cutting by the robot when said robot is under the manual control. Those manual cutting boundaries are set as a maximum depth of the manual cutting, and as maximum longitudinal and lateral movements of the manual cutting. As the cutting boundaries are set by the operator, they are subjected to potential human errors which can lead to serious damages on the cut anatomical structure and its surroundings. With such robot, the operator transmits his/her instructions of movements through a remote joystick or force sensor and the robot software is adapted to execute such instructions, with the sole limitation of the manually set boundaries. Such boundaries are set for the entire phase of the manual cutting and cannot be modified during said manual cutting phase. A feed rate of the cutting is controlled, exclusively, by a software of the robot. Due to its remote workstation location and degrees of freedom, the joystick does not reproduce nor a usual user's grip on a tool handle, nor a natural tool-hand-eye coordination. This document also describes a handle attached to the robot and which comprises six degrees of freedom monitored by a force sensor. A force or torque sensor is, by design, ideally an infinitely stiff system, insensitive to minute displacements. Any non-user triggered movement of the robot, such as for the robot to follow the patient's movements, including as a result of breath or tool cutting efforts, makes it virtually impossible for the user to follow without lag, so generating out-of phase force changes, making it impossible for the user to maintain a relative constant force applied on the force sensor, which end-result is oscillating or erratic robot displacement. Additionally, force/torque sensor results in non-null outputs as soon as the handle is oriented in space away from initial zeroing, due to the own weight of the handle applied to the sensors. Using such a force sensor also results in the transmission of all of the efforts, threshold and user intended, applied on the handle to the robot, thus diminishing the accuracy of such robot. As a result, this set-up is limited in applicability to surgery where the anatomical structures is either attached to the robot structure or maintained very stiff and stable despite any applied surgery induced efforts. The latter is rarely the case as bones are surrounded by flesh.

In summary all the aforesaid mentioned collaborative robots lack of sensitivity and accuracy, especially in presence of patient skeletal movements which restricts their applications.

The present invention falls within this context and aims to solve at least part of the mentioned drawbacks of described collaborative robots currently used by surgeons, mainly on bony structures.

Especially, the present invention relates to a computer-assisted surgery system which presents improved accuracy and improved sensitivity. According to the invention, a surgical tool is attached to a robotic arm and a robot user is actively directing the task from a handle positioned near the tool, so that his expertise and real-time awareness to detect, analyze and react to unwanted critical situations is at its full. The navigated computer-assisted surgery system of the invention offers accuracy of tool placement within a pre-planned region of interest, safety stops at blind or poor visibility anatomical structures transitions, tool weight bearing, machining forces and vibration filtering, as well as filtering of potential hand shakiness.

Advantageously, the computer-assisted surgery system of the invention also permits to follow the motion of anatomical structures, such as bones, in real-time, while the user only provides the main direction of the surgical tool displacements. Currently, the most popular localization technologies for orthopedics are based on optical technology. One or several cameras are used to acquire images of several active and/or passive markers, such as spheres or disks, or natural surfaces and the acquired images are then sent to a computing system which is configured to compute the position and orientation of the markers, and to determine a position and orientation of an object on which are fixed said markers such as bones and surgical tools.

An object of the present invention more specifically concerns a computer-assisted surgery system for treating a region of interest of an anatomical structure with a surgical tool according to a surgical plan, comprising:

a robotic arm comprising at least three motorized joints;

a surgical tool attached to the robotic arm;

a handle comprising:

a fixing part attached to the robotic arm in a fixed position relative to the surgical tool, and a movable part movable relative to the fixing part according to at least three degrees of freedom, at least one activation mechanism configured to control, at least one working parameter of the surgical tool;

a localization unit configured to determine, in real time, relative position and orientation of the surgical tool with respect to the anatomical structure;

a control unit configured to:

send instructions to at least one motorized joint to move the robotic arm, the computer-assisted surgery system being operable in an operative mode allowing a user to control movements of the surgical tool by providing to the control unit inputs in the form of measured displacements applied by the user to the movable part of the handle while treating the region of interest with the surgical tool, wherein the control unit is configured to, as long as the operative mode is enabled:

enable motion of the surgical tool with respect to the anatomical structure only if a user moves the movable part of the handle, receive the measured displacement of the movable part of the handle, receive from the localization unit the relative position and orientation of the surgical tool with respect to the anatomical structure, based on the measured displacement, on the surgical plan and on the relative position and orientation of the surgical tool with respect to the anatomical structure, compute at least one instruction to be sent to at least one of the motorized joints to move the robotic arm to operate the surgical tool according to an optimal trajectory;

send the computed instruction to at least one of the motorized joints.

Especially, the control unit is adapted to determine an intended direction of displacement based on the measured displacement and to consider such intended direction of displacement when it computes the instruction(s) to be sent to the motorized joint(s). The "intended direction of displacement" here refers to a direction along which the user wants the surgical tool to be displaced. Such intended direction of displacement can thus encompass displacement(s) according to one or several degrees of freedom whether translational degree(s) of freedom or rotational degree(s) of freedom. If no other constraint is considered, that is to say if the surgical plan and the relative position and orientation of the surgical tool with respect to the anatomical structure were not considered, such intended direction should be identical, in direction, to the displacement of the robotic arm which results from the execution of the computed instruction(s).

According to the invention, the optimal trajectory is defined as a trajectory permitting to perform the entire treatment of the region of interest as fast as possible and with as more accuracy as possible. By "as fast as possible" we here mean that the optimal trajectory is defined so as to treat the region of interest in the smallest amount of time possible, while ensuring that the surroundings of the anatomical structure to be treated are protected. For instance, the optimal trajectory can be defined based on a strategy defined by the user, before the beginning of the treatment, and which can for instance include safety considerations, such as a region to avoid to protect the surroundings of the anatomical structure to be treated, and/or an as short tool path as possible to perform the planned treatment. Obviously, other constraints can be included in said strategy, such as the selected surgical tool for instance. As detailed below, the control unit can thus be adapted to ensure, for instance, that the surgical tool does not treat the same part of the region of interest more than twice. The control unit can also be adapted to ensure that the execution of the instruction actually permits the surgical tool to treat the region of interest, that is to say that the control unit can be adapted to ensure that the computed instruction(s) are coherent with an attainability of the surgical too. Advantageously, the control unit can also be adapted to ensure that the computed instruction(s) are coherent with a targeted accuracy. Such targeted accuracy can for instance be defined in the strategy defined by the user and can depend on the kind of treatment to be performed. For instance, if the goal if the treatment is to remove big parts of bones, the targeted accuracy will be lower than if the goal of the treatment is to shape the bone to permit the positioning of an implant. The strategy defined by the user can for instance form part of the surgical plan.

Moreover, the control unit is adapted to ensure that the movements of the robotic arm are consistent with the surgical plan, both when the surgical tool is within the region of interest, and also when the surgical tool is approaching such region of interest.

The surgical tool can for instance comprise at least one power tool adapted to drive a tool, such as a cutting tool or a screwdriver for instance. Such cutting tool can for instance be a drill bit, a saw blade, a reamer, or any other known surgical tool. Alternately, the surgical tool can be a non-mobile tool, deprived of power tool, without departing from the scope of the invention. For instance, the non-mobile tool can be a scalpel, a palpation probe or any other known non-mobile tool. Obviously, any other known surgical tool could be used within the scope of the invention.

As mentioned, the surgical tool is fixed in position with respect to the handle fixing part. Especially, the fixing part is fixed in position with respect to the handle as long as the operative mode is enabled. If needed, the user is allowed to displace such handle, for instance between a first phase of the planned treatment and a second phase of said planned treatment, in order to make the manipulation of such handle easier. Additionally, the surgical tool can be changed between said first phase and said second phase. The surgical tool is thus fixed in position with respect to the handle during the first phase and during the second phase but such relative position of the surgical tool with respect to the handle can be different during the first phase than during the second phase. According to the invention, the user must disable the operative mode, before modifying the position of the handle and before changing the surgical tool.

No articulation is formed between the handle fixing part and the surgical tool. The only authorized movement of the surgical tool with respect to the fixing part of the handle, while the operative mode is enabled, are parasitic movements induced, for instance, by vibrations.

Optionally, the handle could be attached directly on the surgical tool. If so, the handle could be attached on the power tool of such surgical tool within the scope of the invention.

The words "motorized joints" here refer to a joint which can be subjected to a linear deformation or to an angular deformation. The robotic arm can thus be realized as a serial robotic arm, as a parallel robotic arm or as a combination thereof. According to an embodiment of the invention, the robotic arm comprises several segments, each segment being separated from the next one by at least one motorized joint, the handle and the surgical tool being attached to the same segment of the robotic arm. Advantageously, the handle and the surgical tool can be attached to the last segment of the robotic arm, that is to say the segment arranged the farthest from a base of the computer-assisted surgery system from which the robotic arm extends. Alternately, the handle and the surgical tool can be attached to two distinct segments of the robotic arm. For instance, the surgical tool can be attached to its last segment while the handle can be attached to its second to last segment.

The working parameter mentioned above can for instance be a working speed of the surgical tool, that is to say a speed at which said surgical tool is adapted to perform the planned treatment. For instance, if the surgical tool is a burr, its working speed is a speed at which such burr rotates. If the surgical tool is an oscillating saw, its working speed is a speed at which the saw blade oscillates. By controlling the working speed of the surgical tool, the activation mechanism is adapted to activate and deactivate such surgical tool.

The words "movable part" here refers to a part of the handle adapted to be displaced along at least 2 mm in translation and by 2° in rotation.

The present invention thus proposes a computer-assisted surgery system wherein the user's input, transmitted in the form of the measured displacement applied to the handle movable part, is not the only input considered by the control unit to compute the instruction(s) to be sent to the motorized joints. The presence of the handle not only aims to provide the user input to the control unit but also participates to the user-friendliness of the method. Indeed, the user actually applies a displacement on the handle, thus providing him/her the intuitive feeling that he/she is actually performing the treatment but preventing any human mistake by using a control unit to modify such displacement with other inputs, and especially with at least one input related to the surgical plan and at least one input related to the relative position and orientation of the surgical tool with respect to the anatomical structure. It is also possible to take into account, as an input, the status of the treatment to be performed at any time, for example the areas of the anatomical structure that have already been treated (sawed, burred or drilled for instance) and the areas that remain to be treated, in order to optimize the surgical time and avoid as much as possible passing on previously treated areas, as well as treating the remaining areas in an optimal way, including an optimal path of the surgical tool trajectory and, as detailed below, an optimal displacement speed of such surgical tool. This principle is further described below as dynamic boundaries.

According to the invention, a reference frame To is attached to the surgical tool, and a reference frame BJ is attached to the handle fixing part, the reference frame To and the reference frame BJ being related to each other thanks to a transform matrix determined by the user and/or by the control unit. As long as the operative mode is enabled, the transform matrix is fixed. Indeed, as previously mentioned, the relative position of the fixing part with respect the surgical tool is fixed as long as the operative mode is enabled. According to the invention, the reference frame To is defined by at least three axes, and the reference frame BJ is defined by at least three axes. Optionally, the transform matrix can be determined such that the three axes defining the reference frame To and the three axes defining the reference frame BJ are parallel, two by two.

Advantageously, at least one of the axes of the reference frame To can be aligned with one of the axes of the reference frame BJ. More advantageously, such axes can also be aligned with a main axis of extension of the surgical tool. As mentioned above, the fixing part is fixed in position with respect to the handle as long as the operative mode is enabled. Consequently, the transform matrix relating the reference frame To and the reference frame BJ is fixed as long as the operative mode is enabled. Such transform matrix can be modified if the relative position of the handle fixing part with respect to the surgical tool is modified. In other words, the transform matrix relating the reference frame To attached to the surgical tool to the reference frame BJ attached to the handle fixing part can be different between a first phase of the planned treatment and a second phase of the planned treatment.

The surgical plan comprises the region of interest and at least one constraint set as one or several of the following:

the kind of treatment to be performed on the anatomical structure, the type of surgical tool used to perform said treatment, a surgical tool access path within the anatomical structure.

According to an aspect of the invention, the control unit is further configured to, as long as the operative mode is enabled:

receive the measured displacement of the movable part of the handle and determine a requested displacement speed of the surgical tool based on said measured displacement, based on the requested displacement speed, on the surgical plan and on the relative position and orientation of the surgical tool with respect to the anatomical structure, compute at least one instruction to be sent to at least one of the motorized joints to move the robotic arm to operate the surgical tool according to an optimal displacement speed, send the computed instruction to at least one of the motorized joints.

The words "displacement speed" here refer to a speed at which the surgical tool progresses, either in approaching the region of interest of the anatomical structure or within it. For instance, the requested displacement speed can be determined based on a length of the measured displacement, the longer the measured displacement is, the faster the requested displacement speed is. The optimal displacement speed is here defined as a speed which permits the surgical tool to perform the planned treatment with efficiency. Such optimal displacement speed is also defined so as to permit the user to lead and follow the displacements of such surgical tool.

The optimal displacement speed can for instance depend on the relative position and orientation of the surgical tool with respect to the anatomical structure. Especially, such optimal displacement speed can for instance depend on the nature of the anatomical structure which is being treated at a given time. For instance, the control unit can be adapted to compute instruction(s) so as for the displacement speed of the surgical tool to be faster in soft bones than in cortical bones. Additionally, the control unit can be adapted to compute instruction(s) so as for the displacement speed of the surgical tool to be faster in parts of the region of interest wherein the treatment has already been performed than in parts of the region of interest wherein the treatment remains to be performed. As previously mentioned, the control unit is also adapted to determine an intended direction of displacement. Obviously, such intended direction of displacement and requested displacement speed can be determined simultaneously, as they depend on the same measured displacement of the handle movable part.

Optionally, the activation mechanism can be adapted to control the requested displacement speed of the robotic arm.

According to the invention, the control unit can also be configured to, as long as the operative mode is enabled:

based on the measured displacement, on the surgical plan and on the relative position and orientation of the surgical tool with respect to the anatomical structure, compute a working range and limit the at least one working parameter of the surgical tool to remain within the computed working range. For instance, such computed working range is defined by one or several of the following parameters:

a maximum displacement speed of the surgical tool, a minimum displacement speed of the surgical tool, a maximum working speed of the surgical tool, a minimum working speed of the surgical tool.

As the working range is computed based on the surgical plan, on the measured displacement and on the relative position and orientation of the surgical tool with respect to the anatomical structure, a value of the at least one parameter which defines such working range is re-calculated permanently and can be modified.

It is understood that the user remains in charge of requesting any displacement speed of the surgical tool, through the displacement of the handle movable part, within the limits defined by the minimum displacement speed and the maximum displacement speed of the surgical tool.

The maximum displacement speed and the maximum working speed can be varied depending on the surroundings of the anatomical structure to be treated, or on the nature of this anatomical structure, thus aiming to prevent damages on said surroundings of the anatomical structure such as vessels or nerves. Additionally, the maximum displacement speed can be varied depending on the targeted accuracy.

According to an example of the invention, the maximum displacement speed and/or the maximum working speed of the surgical tool can depend on a distance measured between the position of the surgical tool and at least one predetermined point of the region of interest. According to this example, such predetermined point(s) of the region of interest can be part of a boundary limiting the region of interest. If so, the smaller such distance is, the lower the maximum working speed and the maximum displacement speed are. In other words, the maximum working speed and the maximum displacement speed of the surgical tool are lower and lower as the surgical tool comes closer to said boundary. Such maximum working speed and maximum displacement speed of the surgical tool can be set to zero when the distance measured between the surgical tool and the predetermined point(s) of the region of interest reaches zero, that is to say, when the position of the surgical tool reaches the position of the predetermined point(s). The predetermined point(s) can be realized as at least one dynamic point. As such, this predetermined point(s) can be redefined permanently by the control unit, for instance, depending on the direction of displacement of the surgical tool.

Alternately or cumulatively, the maximum displacement speed and the maximum working speed of the surgical tool can depend on the hardness of the part of the anatomical structure on which the treatment is currently performed, that is to say depending if the treatment is currently performed on a cortical bone or on a soft bone for instance. As explained below, these information about the hardness of the anatomical structure is recorded before the beginning of the treatment.

According to the invention several of these parameters can be coupled to one another, and such coupling or interaction can vary over the planned treatment. In other words, at least some of the parameters related to the planned treatment can be dependent from one another. For instance, the maximum working speed of the surgical tool and the maximum displacement speed of such surgical tool may be coupled to a certain degree by the control unit. The maximum working speed of the surgical tool and/or the maximum displacement speed of such surgical tool may be limited based on the nature of the anatomical structure and on a dissipated power of the surgical tool to progress. Limiting the maximum working speed and/or the maximum displacement speed of the surgical tool based on the dissipated power of the surgical tool to progress permits to avoid thermal damage which could for example result in necrosis of remanent structures, poor healing, inflammation of tissues, longer recovery timelines. The chosen surgical tool can also be coupled to other parameters, such as the maximum working speed or the minimum working speed of the surgical tool, the maximum displacement speed of the surgical tool or a set of needed operative degrees of freedom to perform the treatment. Also, the maximum working speed can be coupled to the geometry of the surgical tool access path constraint within the anatomical structure and to the provided positions of environmental obstacles.

According to the invention, the interaction between these parameters can be defined before the beginning of the planned treatment and/or they can be varied during such planned treatment.

According to an aspect of the invention, the control unit or the user can set at least one static boundary, based on the region of interest, the control unit being adapted to compute instructions so as to prevent the surgical tool from crossing said static boundary. Such static boundary ensures that the treatment is performed only within the region of interest. For instance, such static boundary can be set before the enabling of the operative mode and cannot be modified as long as said operative mode is enabled, neither by the user of the computer-assisted surgery system, nor by the control unit.

For instance, if the planned treatment consists in drilling a hole in the anatomical structure, a first static boundary can be a peripheral contour of such future hole, which can be shaped as a cylinder, and a second static boundary can be an end of the hole not to be crossed beyond by the drill bit. Optionally, at least one entry boundary can also be set at the surface of the anatomical structure to be drilled. In another example, the static boundary can be a contour of a planar cut to be performed in a bone during an osteotomy, for example it can be for high tibial osteotomy procedures, or total knee arthroplasty, or cut of femur for placing a hip implant. In another example, the static boundary can be the surface of a bone that must be burred to place an implant, such as a keel of a prosthesis. Such static boundary can thus contribute to define the optimal trajectory and the optimal speed.

According to another aspect of the invention, the control unit can be configured to set at least one dynamic boundary, the control unit being adapted to modify the dynamic boundary during the course of the treatment and the control unit being adapted to compute instructions so as to prevent the surgical tool from crossing said dynamic boundary. This dynamic boundary can be modified without specific input from the user. Such dynamic boundary can also contribute to define the optimal trajectory and the optimal displacement speed.

For instance, the control unit can be adapted to reduce the displacement speed of the surgical tool to zero along at least one direction as the surgical tool reaches the at least one static boundary or the at least one dynamic boundary, so as to prevent the surgical tool from crossing, respectively, said static boundary or said dynamic boundary.

Alternately or cumulatively, when the surgical tool reaches the at least one static boundary or the at least one dynamic boundary, the optimal trajectory is defined so as for said surgical tool to be displaced along the concerned static boundary or the concerned dynamic boundary.

Optionally, the control unit can be adapted to compute instruction(s) so as for the surgical tool to be snapped on one of the static boundary or the dynamic boundary, as soon as a distance measured between such surgical tool and the concerned static boundary or the concerned dynamic boundary, is below a predefined value.

As previously mentioned, the optimal trajectory can for instance imply that the surgical tool does not treat three times the same parts of the region of interest. In other words, the optimal trajectory can imply that the surgical tool does not treat the same parts of the region of interest more than twice. One way to do such is to set the at least one dynamic boundary, to prevent the surgical tool to operate three times at a same location of the region of interest. As mentioned above, such dynamic boundary is set by the control unit. In other words, the at least one dynamic boundary can be set, by the control unit, as the contour of the parts of the anatomical structure on which the planned treatment has already been performed. Such dynamic boundary thus permits the surgical tool to overlay some already treated parts of the anatomical structure, thus ensuring that the wanted treatment—for instance the wanted cutting—is completed, while ensuring that the surgical tool is not unnecessarily re-operated in an already treated part of the region of interest. Such dynamic boundary thus aims at performing the planned treatment as fast as possible. The modification of the dynamic boundary permits to give access to the user, only to area(s) wherein part of the planned treatment has not yet been performed, thus optimizing the trajectory and avoid unnecessary displacements.

Additionally, the optimal trajectory can also imply that the surgical tool is adapted to treat the region of interest along such optimal trajectory. To do such, the at least one dynamic boundary is set, by the control unit, so as for the displacements of the robotic arm to be coherent with the attainability of the surgical tool.

The words "attainability of the surgical tool" here refers to a geometric zone wherein the surgical tool is actually adapted to perform the planned treatment. Several examples of how to comply with such attainability of the surgical tool are described below. For instance, if the surgical tool is a drill to which a burr is attached, the surgical tool is adapted to cut only parts of the anatomical structure in contact with said burr, the dynamic boundary can, in this situation, be set so as to prevent the user from inserting the surgical tool too deeply into the region of interest, thus preventing to damage such surgical tool, while still permitting to perform the planned treatment. Alternately or cumulatively, such at least one dynamic boundary can also be used to forbid some displacements of the surgical tool. For instance, if the surgical tool is a saw adapted to perform a cut only along one direction, at least one dynamic boundary can be set by the control unit, to prevent displacements of the surgical tool along, at least some of, the other directions. As the planned treatment is performed, some of these displacements can later become available, the control unit thus being adapted to set a new corresponding dynamic boundary. If the planned treatment consists in removing a volume of the anatomical structure with the surgical tool, the dynamic boundary can be the corresponding parts of the anatomical structure that are to be removed within cutting capabilities of the surgical tool at any point in time and space. This dynamic boundary thus changes during the course of the treatment, as the cutting is performed. According to different ways of carrying the invention, this dynamic boundary can be modified as the planned treatment is performed, until the dynamic boundary reaches the static boundary. Optionally, the maximum displacement speed of the surgical tool can be increased in areas wherein the planned treatment has already been performed, such that the user can come freely in any area and avoid losing time in areas that have been treated already. In other words, these dynamic boundaries can also be used to define the optimal displacement speed of the surgical tool.

Obviously, the features described with reference to each of these examples can be combined within the scope of the invention. The control unit can thus be adapted to set at least one static boundary, at least one dynamic boundary so as to prevent the surgical tool from being operated more than twice at a same location of the region of interest, and/or at least one dynamic boundary so as to be coherent with the attainability of the surgical tool, within the scope of the invention. Obviously, any other combination of the static and dynamic boundaries can be realized without departing from the scope of the invention.

Optionally, the control unit or the user can set at least one entry boundary, based on the region of interest, such entry boundary forming an access zone to the region of interest, the control unit being adapted to compute instruction(s) so as for the surgical tool to cross said entry boundary to reach the region of interest. Such entry boundary thus forms an access zone or an access point to the region of interest. The control unit is adapted to compute instructions so as for the surgical tool to necessarily cross such entry boundary, at least once.

As mentioned above, the surgical plan comprises a defined surgical tool access path constraint. According to an aspect of the invention, the control unit can thus be adapted to compute instruction(s) so as for the surgical tool to be displaced within such surgical tool access path for reaching the region of interest, the surgical tool access path being defined by at least the entry boundary and by at least one protective boundary set by the control unit or by the user.

The at least one protective boundary thus aims to prevent the surgical tool to damage the surroundings of the access zone, often made of soft tissues, nerves and/or vessel. The surgical tool access path constraint within the anatomical structure can be defined so as for the planned treatment to be optimized. For instance, this surgical tool access path constraint can be defined so as to provide access to the region of interest but preventing any interference with other anatomical structures. For example, this access path constraint can form a tunnel through which the surgical tool is inserted, the limits of such tunnel being set as protective boundaries by the control unit, and such access path constraint can encompass a pivot point or pivot area of the surgical tool at the entry boundary, thus ensuring that such surgical tool is able to reach any part of the region of interest while preventing damaging soft tissues through which such surgical tool has been inserted. Obviously, this is only an example and the access path constraint could be of any geometry within the scope of the invention.

The system of the invention is also adapted to permit the user to define an extended region of interest, such extended region of interest extending beyond the at least one static boundary. Optionally, the control unit can be adapted to compute a more stringent working range in the extended region of interest than in the region of interest.

For instance, the user can define such enlarged region of interest by creating an offset to an existing static boundary, by drawing such on a human-machine interface which can for instance be realized by a display or a touchscreen.

According to the invention, the enlarged region of interest can be formed as a part of a region defined as a region to avoid wherein the user is able to perform part of the planned treatment. As the user of the computer-assisted surgery system performs the treatment, he/she can need to perform part of such treatment outside the defined region of interest, that is to say in a part of the region to avoid. The method of the invention permits such user to indicate that he/she needs to override the static boundaries of the defined region of interest and that he/she needs to operate treatment in some part(s) of the region to avoid. Said part(s) of the region to avoid thus becomes available to the user, optionally with a more stringent working range. For instance, the maximum working speed of the surgical tool or the maximum displacement speed of the surgical tool can be lower in such enlarged region of interest than in the region of interest.

According to an aspect of the invention, the control unit can be configured to detect a vibration applied on the handle movable part and to filter the detected vibration when computing the instruction(s) to be sent to the motorized joint(s).

The eventual shakiness of the user is thus not transmitted to the robotic arm. For instance, these vibrations can be detected thanks to an accelerometer implemented in the handle. Alternately or cumulatively, the control unit can be adapted to detect such vibrations based on the frequency of the measured displacements, the control unit being adapted to filter the measured displacements which present a frequency above a defined threshold. Optionally, the motor of the power tool of the surgical tool can be adapted to send an information to the control unit related to an amount of current it uses, the control unit being adapted to compute the instruction(s) considering such value of the current. For instance, if the value exceeds a predetermined threshold, the control unit can be adapted to warn the user that he/she is probably trying to perform a forbidden movement. Optionally, the control unit can be adapted to stop the surgical tool when the value of the current used by the motor of the surgical tool exceeds said predetermined threshold. Each motor of the motorized joints can also be adapted to send such information to the control unit.

According to an aspect of the invention, the handle movable part comprises at least one translational degree of freedom, said translational degree of freedom being parallel to a main axis of extension of the surgical tool.

Optionally, the computer-assisted surgery system can comprise at least one detecting device adapted to detect that the handle is held by the user's hand, the control unit being configured to enable movement of the surgical tool only if the handle is held by the user's hand, as long as the operative mode is enabled. Such detecting device can be arranged on the handle. Especially, such detecting device can be housed in a gripping part of such handle. Alternately, the detecting device can be arranged on any other part of the computer-assisted surgery system or realized as a pedal. This detecting device thus ensures that the control unit considers the measured displacement applied on the handle movable part, only when the user willingly applies said displacement, therefore preventing any unwanted displacement of the surgical tool and/or of the robotic arm.

According to an aspect of the invention, the surgical tool comprises an immaterial tool center point which forms an origin of the reference frame To. Consequently, such immaterial tool center point forms a point around which rotations of the surgical tool are applied, an axis of rotation of the rotation applied around the tool center point being parallel to an axis of rotation of the rotation applied on the handle movable part. The control unit can be adapted to dynamically modify the immaterial tool center point during the course of the treatment. As such, depending on a depth along which the surgical tool is inserted in the region of interest, the modification of the tool center point permits the user to gain more accuracy in the requested displacements, thanks to easier hand movement coordination.

According to an aspect of the invention, the handle can comprise at least three displacement sensors, each displacement sensor being adapted to detect and measure the displacements of the movable part according to at least one respective degree of freedom, at least two of said displacement sensors being configured to redundantly detect and measure displacements of the movable part according to at least one same degree of freedom. According to this aspect of the invention, the displacements measured by the two displacement sensors can be measured identically, the same measure being thus realized by both the displacement sensors. Alternately, the two displacement sensors can be adapted to measure the displacements according to at least two independent manners, the values obtained by such displacement sensors then being compared to each other.

According to a configuration of the system, the handle can be shaped as a pistol grip, an angle formed between a main axis of extension of the handle and a main axis of extension of the surgical tool being greater or equal to 30°. An assembly of the handle with the surgical tool thus present a L-shape. Such configuration is really close to the shape of traditional surgical tools used in orthopedic surgeries. Therefore, the time needed for the user to be comfortable using the system of the invention instead of said traditional surgical tool is greatly reduced.

According to another configuration of the system, the mains axis of extension of the handle can be aligned with the main axis of extension of the surgical tool. This other configuration is also close to the shape of some traditional surgical tools adapted to be manipulated as stylus. Again, such configuration reduces the time needed by the user to be comfortable using the system of the invention.

According to yet another configuration, the surgical tool can be attached to the robotic arm thanks to a shaft and the handle can surround, at least partially, the surgical tool's shaft. Such configuration additionally improves the user-friendliness of the system by giving the user the intuitive feeling that he/she is actually performing the treatment. This configuration thus aims to make the system transparent for the user.

According to the invention, the computer-assisted surgery system is operable in a collaborative mode allowing the user to control movement of the robotic arm by providing to the control unit inputs in the form of measured displacements applied to the movable part of the handle while the surgical tool is deactivated. According to the invention, the control unit is configured to, as long as the collaborative mode is enabled:

receive the measured displacement of the movable part of the handle, determine, based on the measured displacement, the intended direction of displacement, based on the measured displacement, compute at least one instruction to be sent to at least one of the motorized joints to move the robotic arm to move the robotic arm according to the intended direction of displacement;

send the computed instruction to at least one of the motorized joints.

The collaborative mode thus differs from the operative mode in that the handle is used to control the robotic arm, instead of the surgical tool, and in that the relative position and orientation of the surgical tool with respect to the anatomical structure are not considered by the control unit to compute the instruction(s). When the collaborative mode is enabled, the activation mechanism can be adapted to control a displacement speed of the robotic arm. Optionally, the control unit can be adapted to consider a region to avoid in the computing of the instruction(s) when the collaborative mode is enabled. Such region to avoid can, in this situation, be formed as the patient's body plus a safety layer.

The control unit can be adapted to select a first set of degrees of freedom during a first phase of the treatment and the control unit can be adapted to select a second set of degrees of freedom during a second phase of the treatment, distinct from the first set of degrees of freedom. The selection of a set of degrees of freedom permits the control unit to define which degrees of freedom to consider while computing the instruction(s), thus ensuring that the execution of the computed instruction(s) permits the surgical tool to be operated within the defined region of interest.

For instance, the computer-assisted surgery system can be operated according to the collaborative mode during the first phase of the treatment and according to the operative mode during the second phase of the treatment. Obviously, this computer-assisted surgery system can also be used to perform any multiple-phase treatment wherein each phase is realized in the operative mode and wherein each phase necessitates the control unit to consider a specific set of degrees of freedom. The set of degrees of freedom considered by the control unit can be changed during the treatment performed with the help of the computer-assisted surgery system. This selection of the set of operative degrees of freedom considered by the control unit can be done before starting the planned treatment or while performing it within the scope of the invention. Optionally, the system can be adapted to force the user to disable the operative mode to permit the control unit to select a new set of degree of freedom.

According to a first example of the invention, the handle movable part can comprise at least three degrees of freedom, upon which a first translational degree of freedom, a second translational degree of freedom and a rotational degree of freedom. As an example, the selection of the set of degrees of freedom considered by the control unit can result in that the control unit only considers the first translational degree of freedom and the activation mechanism when computing the instruction(s). Such a configuration can for example be selected when the planned treatment is set as drilling a hole into a bone and when, consequently, the surgical tool is a drill bit. During such treatment, the user indeed only needs to move the surgical tool along one axis and to activate such surgical tool to perform such drilling. According to this first example, the handle thus controls the activation and the movements of the drill bit only in one direction and the displacements applied on the movable part along the other directions are filtered and ignored by the control unit.

Obviously, the same goal can be achieved with a handle movable part comprising more than three degrees of freedom, all of them but one being deactivated so as for the control unit to only consider the translational degree of freedom of interest in its calculation of the instructions to be sent to the surgical tool.

According to a second example of the invention, the handle movable part can comprise four degrees of freedom, upon which a first translational degree of freedom, a second translational degree of freedom, a third translational degree of freedom and a rotational degree of freedom, the selection of the set of degrees of freedom considered by the control unit resulting in that the control unit only considers the first translational degree of freedom, the second translational degree of freedom, the rotational degree of freedom and the activation mechanism when computing the instruction(s). According to this other example, the rotational degree of freedom can for instance be related to a rotation realized around an axis perpendicular to a plane defined by the first and the second translational degrees of freedom, the first translational degree of freedom being parallel to the main axis of extension of the surgical tool. This second example can for instance be useful to perform a cut within a predetermined cutting plane and with an oscillating saw. The three operative degrees of freedom thus permits to move the oscillating saw only within the predetermined plane, while the fourth degree of freedom, in this case the third translational degree of freedom, is filtered and ignored by the control unit.

According to a third example of the invention, the handle movable part can comprise six degrees of freedom, upon which three translational degrees of freedom and three rotational degrees of freedom. According to this other example, the handle can be used, during a first phase of the planned treatment, in the collaborative mode, to rapidly position the robotic arm and the surgical tool attached to such robotic arm, thus using all the six available degrees of freedom. The user can use the handle to position the surgical tool held by the robotic arm close to the region of interest in position and orientation. During this first phase, the user can have a full view of the scene, thus permitting him/her to quickly position the robotic arm and the attached surgical tool without any conflict with the eventual obstacles that can be present in the vicinity of the system. This first phase can then be followed by a second phase, called a "pre-operative phase" during which the control unit makes a precise alignment of the surgical tool with respect to the region of interest, without user directional input. The first and second phase can be followed by a third phase, where the planned treatment is actually performed. As mentioned above, this planned treatment can for instance consist in drilling a hole in a bone which necessitates only one translational degree of freedom and the activation mechanism. The selection of the set of degrees of freedom considered by the control unit here permits to switch from the handle encompassing six degrees of freedom to a handle encompassing only the useful degree of freedom. Thus, the step of selecting the set of degrees of freedom considered by the control unit here consists in the deactivation of five of the six degrees of freedom. This deactivation is digital, that is to say that the user can still displace the handle movable part along said deactivated degrees of freedom but that the control unit is adapted to filter and ignore such displacements. Alternately, the planned treatment can consist in performing a planar cut with a saw which necessitates three operative degrees of freedom. According to this alternative for a saw cut, the step of modifying the set of degrees of freedom considered by the control unit here permits to switch from the handle encompassing six degrees of freedom to a handle encompassing only the three useful degrees of freedom.

Of course, those are only examples of the sets of operative degrees of freedom which can be selected and any other combination of operative degrees of freedom can be chosen within the scope of the invention.

To generalize, any combination of the degrees of freedom can be selected, the set of operative degrees of freedom being selected depending on the surgical plan and on the mode which is currently enabled. According to the invention, the selection of the set of degrees of freedom considered by the control unit can be done while preparing the treatment and/or during said treatment. For example, one can foresee the case of a treatment in which a first phase requires the use of three degrees of freedom to perform a cut within a predefined plane and in which a second phase requires the use of only one degree of freedom to perform said second phase of said treatment within a predefined line for drilling a hole. In the present description, the "set of degrees of freedom considered by the control unit" is also referred to as "operative degrees of freedom".

Optionally, the selection of the set of operative degrees of freedom can be done manually. To do so, the computer-assisted surgery system of the invention can comprise at least one manually activated device adapted to select a specific set of degrees of freedom which can for instance be arranged on the handle. This manually activated device can for instance be formed as a switch or as a joystick arranged on the handle. Obviously, it is only an example of the invention and the concerned manually activated device could take any other form and be arranged on any other part of the computer-assisted surgery system without departing from the present invention. For example, the user may interact with a human-machine interface to select the set of operative degrees of freedom. According to another example, the modification of the set of operative degrees of freedom can be controlled by a voice command.

According to the invention, the computer-assisted surgery system is operable in a pre-operative mode allowing the control unit to control movement of the robotic arm while the surgical tool is deactivated, the control unit being adapted to, as long as the pre-operative mode is enabled:
receive from the localization unit the relative position and orientation of the surgical tool with respect to the anatomical structure,
based on the surgical plan and on the relative positions and orientations of the surgical tool with respect to the anatomical structure, compute at least one instruction to be sent to at least one of the motorized joints to move the robotic arm to position the surgical tool so as for a main axis of extension of said surgical tool to be aligned with at least one planned working direction within the region of interest;

send the computed instruction to at least one of the motorized joints.

Here, the words «working direction» must be understood as a direction along which at least part of the planned treatment must be performed. For instance, if the planned treatment consists in drilling a hole, the at least one working direction corresponds to an axis along which said hole must be drilled. It is understood that when such pre-operative mode is enabled, the displacements of the movable part eventually detected are not considered by the control unit when it computes the instruction. When the pre-operative mode is enabled, the control unit can be adapted to compute instruction(s) so as to ensure that the surgical tool will not cross the entry boundary.

According to an aspect of the invention, the alignment of the surgical tool with the region of interest, and especially of the surgical tool main axis of extension with the at least one working direction, can be realized by snapping such surgical tool to the nearest boundary, whether it is a static boundary or a dynamic boundary. The control unit can thus be adapted to compute instruction(s) so as to ensure that such snapping will result from the execution of the instruction(s).

According to an example of the invention, the region of interest can be formed as an infinite plane. Alternately, the region of interest can be formed as a planar portion of the anatomical structure. The instruction(s) are thus computed so as for the surgical tool to remain in said cutting plane, or in said infinite plane, as long as the operative mode is enabled. The instructions are also computed so as for the surgical tool to remain in said cutting plane or in said infinite plane even in the enlarged region of interest defined above.

According to a feature of the invention, the user may have main visual feedback of his/her inter-active guidance from the system. In a preferred embodiment, a human-machine interface, such as a display or a touchscreen, can be positioned in the vicinity of the anatomical structure, such human-machine interface being adapted to represent the real time position of the surgical tool, and especially of a surgical tool tip, with respect to the anatomical structure to be treated while permitting the user to have direct-sight towards the region of interest. For instance, the human-machine interface can be mounted on an articulated arm, itself attached to a surgical table so as for the user to be able to see the information displayed on such human-machine interface. Alternately, the human-machine interface can be mounted on the end-effector or in the vicinity of the fixing part of the handle. Alternately, the human-machine interface can be realized as an augmented reality, video see-through headset and the like.

The static and dynamic boundaries previously mentioned can be displayed on the human-machine interface with different colors, so as to be quickly understandable for the user.

The present invention thus provides a flexible interface between the handle and the surgical tool so that a displacement exerted by the user on the handle movable part does not necessarily generate any direct displacement of the surgical tool, but such that said displacement exerted on the handle movable part generates a command that is processed by the control unit to generate an active displacement of the robot holding the surgical tool in directions that are a combination of the directions detected by the displacement sensors—also referred to as "user's input"—and/or of the surgical plan and/or of the provided relative position and orientation of the surgical tool with respect to the anatomical structure to execute an optimal action on the anatomical structure to be treated.

In other words, the directions detected by the displacement sensors are processed with predefined constraints when computing the instruction(s), such constraints having many different formats. First, we can cite some geometric constraints which constrain the surgical tool to remain within a region of interest and outside a region to avoid. For example, those geometric constraints can be staying in a line, staying on a plane with boundaries wherein the surgical tool extremity must execute a complete removal of a bone area for efficient surgery and not go outside said boundaries to protect some structures integrity, or staying inside a volume with boundaries wherein the surgical tool extremity must not go to protect some structures integrity. Second, we can cite some displacement constraints, which ensure that the surgical tool's movements are adapted to perform the planned treatment, in an optimized way. For instance, these displacement constraints can comprise an optimal speed at a given location taking into account characteristics of the anatomical structure at the location of the surgical tool. For example, mechanical properties of a bone that can be deduced from absorbed tool power or from the intensity of a corresponding 3D images can be used to assign a property such as soft bone (cancerous bone) or hard bone (cortical bone) and the speed of displacement of a saw or burr can be adapted to be faster in soft bone and slower in hard bone.

Other examples of displacement constraints can result in filtering the displacements exerted by the user to suppress shakiness, in processing the displacements exerted by the user to maintain an optimal trajectory of the surgical tool, in processing the displacements exerted by the user to optimize the trajectory of the surgical tool to avoid areas wherein the surgical tool has already performed part of the planned treatment and therefore save time or in processing the displacements exerted by the user to optimize the trajectory of the surgical tool to approach the anatomical structure with an optimized cutting angle. Obviously, those are only examples of the constraints that can be considered by the control unit to compute the instructions to be sent to the motorized joints. According to an example of the invention, the sensitivity of the handle is directly related to the sensibility of the displacement sensors.

BRIEF DESCRIPTION OF THE DRAWINGS

Further details and features of the invention are described below with reference to the following drawings:

FIGS. 28 to 30 illustrate different embodiments of a surgical tool adapted to be used with the computer-assisted surgery system of the invention, FIGS. 28 and 28b is illustrating a surgical saw, FIG. 29 illustrating a surgical burr and FIG. 30 illustrating a femoral head impactor.

Unless otherwise specified, all the features described below can be combined with each other, even if not described or shown on the same figure or if described with reference to distinct embodiments of the invention.

DETAILED DESCRIPTION OF EMBODIMENTS

Figure 1:
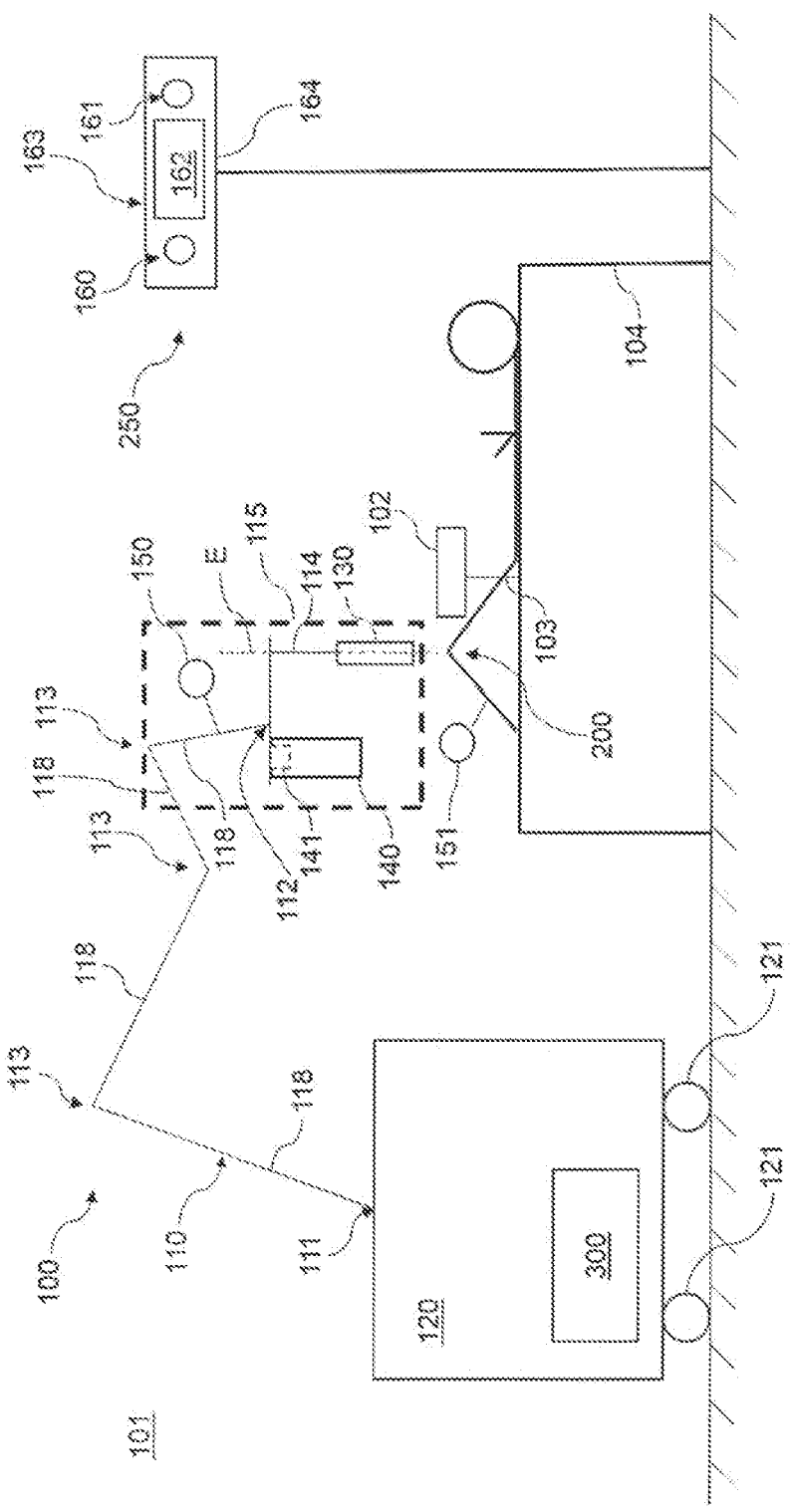
FIG. 1 illustrates, schematically, a computer-assisted surgery system of the invention illustrated in an operating room, while performing a planned treatment on an anatomical structure.

FIG. 1 illustrates, schematically, a computer-assisted surgery system 100 according to an embodiment of the present invention, such computer-assisted surgery system 100 being represented in an operating room 101. In the following specification, the words "computer-assisted surgery system 100" and "system 100" are used without any distinction. This computer-assisted surgery system 100 comprises at least one robotic arm 110 extending between a first end 111 and a second end 112. As shown, the first end 111 is attached to a base 120 of the computer-assisted system 100 and the second end 112 forms a flange of the robotic arm 110 to which an end-effector 115 is fixed. As described below, the end-effector 115 can also comprise part of the robotic arm 110 located before its flange, that is to say between the base 120 and the flange.

According to the illustrated embodiment, the base 120 is a movable base, and comprises wheels 121. Such embodiment allows the user of the system to easily move the base depending on the treatment to be performed. According to non-illustrated embodiments, the base can be movable along rails or it can alternately be a fixed base, or it can be arranged on any suitable device. Obviously, when a mobile base is used, it encompasses means adapted to lock the position of such base during the planned treatment.

At least three motorized joints 113 are formed between the first end 111 and the second end 112 of the robotic arm 110. More than three motorized joints 113 can be formed between the first end 111 and the second end 112 of the robotic arm 110. The words "motorized joint" here refer to a joint driven by its own motor, such joint being adapted to be subjected to a linear deformation or to an angular deformation, within the scope of the invention. In other words, if n joints are formed between the first end 111 and the second end 112 of the robotic arm 110, the robotic arm 110 comprises n motors, each of which being adapted to drive one of the joints. The robotic arm 110 comprises several segments 118. According to the illustrated embodiment, each segment 118 is separated from the next one by at least one motorized joint 113. According to the invention, the words "end-effector" 115 designates the last segment 118 of the robotic arm 110, that is to say the segment of such robotic arm 110 positioned the farthest from the base 120 of the system 110, or the second to last segment 118 of the robotic arm 110. Alternately, the end-effector 115 can comprise one or several motorized joint(s) and it can thus comprise at least two segments 118 of the robotic arm 110. In specific embodiment of the invention, the end-effector 115 can itself encompass one or several additional segments and related degrees of freedom, such as a power tool in translation, irrigation and suction apparatus, safety observation instrumentation etc.

The robotic arm 110 illustrated is a serial robotic arm, but this robotic arm could be a parallel robotic arm, or a combination thereof within the scope of the invention. According to an embodiment of the invention, the robotic arm can present at least six motorized joints.

The computer-assisted surgery system 100 also comprises at least one surgical tool 130 adapted to be used to perform a treatment on an anatomical structure 200 and at least one handle 140. The surgical tool 130 and the handle 140 are both attached to the robotic arm 110. According to the illustrated embodiment, the handle 140 and the surgical tool 140 form parts of the end-effector 115 of the robotic arm 110. As the surgical tool 130 and the handle 140 form part of the end-effector 115, it is understood, from what have been described above referring to the end-effector, that such surgical tool 130 and such handle 140 can be arranged on the last segment 118 of the robotic arm 110 or on the second to last segment 118 of such robotic arm 110. According to the illustrated embodiment, the surgical tool 130 and the handle are fixed to the flange of the robotic arm 110. For instance, the surgical tool 130 can be fixed to such flange thanks to a shaft 114. Alternately, the surgical tool 130 can be directly mounted on the flange of the robotic arm 110. According to a non-illustrated embodiment, the handle 140 can be directly fixed to the surgical tool 130.

According to an embodiment of the present invention, the surgical tool 130 can comprise at least one power tool adapted to drive a tool. The tool can for instance be a cutting tool, such as a saw, a drill, a reamer or a burr. According to another embodiment of the invention, the surgical tool 130 can be a cutting guide or an insertion guide. Obviously, those are just examples of the surgical tool 130 and any other known surgical tool 130 can be used without departing from the scope of the present invention. Any surgical tool that is adapted to act on or to treat an anatomical structure can be attached to the robotic arm within the scope of the invention. For example, the surgical tool can be also an ultrasonic bone scalpel, a bone shaver, a laser that can cuts tissues or bones, a knife, a lancet, a cryosurgery probe, any radiofrequency tool, a microwave probe, a waterjet device, or a screwdriver.

According to an example of application of the invention, the anatomical structure 200 can be a bone of a patient. According to the illustrated embodiment, the anatomical structure 200 is for example a tibial bone of the patient. As previously mentioned, the illustrated embodiment is only one example of how to carry the invention and the anatomical structure could be any other anatomical structure of said patient within the scope of the invention. For instance, this anatomical structure could be a femur bone, a shoulder scapula or humerus, a maxillo-facial bone, a small hand or foot bone such as metatarsal bone or talus, a vertebra, a pelvis, a tooth or mandible, a skull, a brain etc. . . . . The system 100 of the invention is particularly well suited to be used during orthopedic, ENT, cranio-facial, dental surgeries, or neurosurgery.

The system 100 of the invention further comprises at least one control unit 300. A function of the control unit 300 is to compute and instruct movement(s) to the motorized joints 113 of the robotic arm 110 which holds the surgical tool 300. The control unit can, for instance, comprise one or more microprocessor, one or more random access memory (RAM) and/or one or more read-only memory (ROM), one or more calculators, one or more computers and/or one or more computer programs. The computer program(s) comprise code instructions to compute the needed instructions to be sent to the motorized joints 113 of the robotic arm. 110. In addition, the control unit 300 may include other devices and circuitry for performing the functions described herein such as, for example, a hard drive, input/output circuitry, and the like. The input/output circuitry can be adapted to treat digital and/or analog signals.

According to the invention, the instructions adapted to be sent by the control unit 300 are computed by said control unit 300 based on several inputs, parameters and constraints described below. According to the illustrated embodiment, the control unit 300 is integrated within the base 120 but such control unit 300 could be remoted without departing from the scope of the invention. As detailed after, the surgical tool 130 comprises a tool center point which forms the point of such surgical tool around which are applied the rotations requested by the user—and modified by other inputs. This tool center point can be modified during the course of the treatment.

According to the invention, the handle 140 comprises at least one movable part 141 which presents at least three degrees of freedom. Among these three degrees of freedom, at least one can be a translational degree of freedom. Such translational degree of freedom can be parallel to a main axis of extension E of the surgical tool 130. For instance, the number of degrees of freedom of the handle movable part can be identical to the number of motorized joints of the robotic arm. Different embodiments of such handle 140 are for instance illustrated on FIGS. 2 to 13. As explained below, the at least three degrees of freedom can for instance comprise at least one rotational degree of freedom and at least two translational degrees of freedom. Of course, this is only one embodiment of the invention and those degrees of freedom could be different without departing from the scope of the invention. For instance, the handle 140 can comprise up to six degrees of freedom, upon which three translational degrees of freedom and three rotational degrees of freedom. In a non-illustrated embodiment, the handle movable part can encompass three degrees of freedom made of three rotations. A compliance of the handle movable part 141 can be higher than a compliance of the robotic arm 110, said compliance being measured along the same degree of freedom. In other words, the handle 140, and especially the handle movable part 141, presents a lower stiffness than the robotic arm 110. Such difference of compliances—or stiffnesses—prevents the displacement applied on the handle movable part from being mechanically transmitted to the robotic arm.

According to an aspect of the invention, at least a portion of the movable part 141 can be urged to a neutral position by at least one elastic return means. Such elastic return means can for instance be formed as a spring or as an elastic band. As explained in an example given below, this at least one elastic return means is adapted to counter a weight of the handle 140 and thus to keep the handle movable part 141 in a neutral position. For instance, the concerned portion of the movable part 141 can be urged to the neutral position along a first direction thanks to one elastic return means and it can be urged to the neutral position along a second direction, secant to the first direction, thanks to another elastic return means distinct from the first one. This other elastic return means can for instance be realized by a spring or an elastic band.

Optionally, the system 100 of the invention can also comprise a human-machine interface 102, positioned in the vicinity of the anatomical structure. As shown on FIG. 1, this human-machine interface 102 can be supported by an articulated arm 103 attached to a surgical table 104 on which the patient lies. Alternately, the human-machine interface can be mounted on the end-effector 115 or in the vicinity of the handle 140. These positions of the human-machine interface

102 all permit the user to be able to look, almost simultaneously, the patient, and especially the anatomical structure 200 on which the planned treatment has to be performed and said human-machine interface 102 which provides him/her with information that cannot be obtained by only looking at the anatomical structure, especially when the planned treatment is a minimally invasive surgery. For instance, the human-machine interface 102 is adapted to display the real time position of the surgical tool, and especially of a surgical tool tip, with respect to the anatomical structure to be treated while permitting the user to have direct-sight towards the region of interest. This human-machine interface 102 can for instance be realized as a display or a touchscreen. According to a non-illustrated embodiment, the human-machine interface 102 can be realized as an augmented reality, video see-through headset or the like. More details are given below with respect to the information displayed on such human-machine interface.

Figure 2:
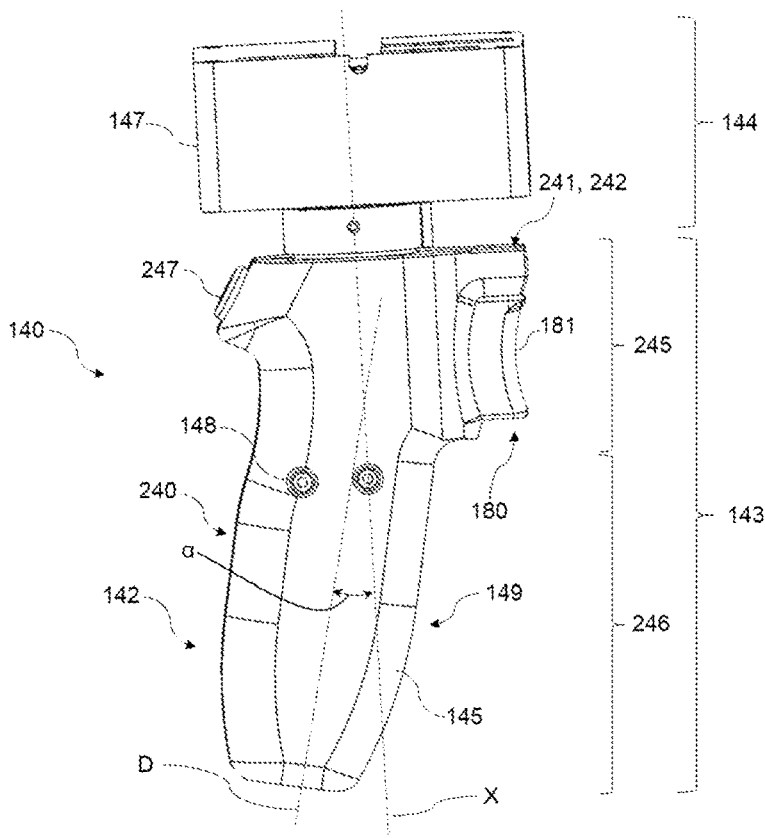
FIG. 2 illustrates, in a perspective view, a handle of the computer-assisted surgery system according to a first embodiment of the invention.
Figure 14:
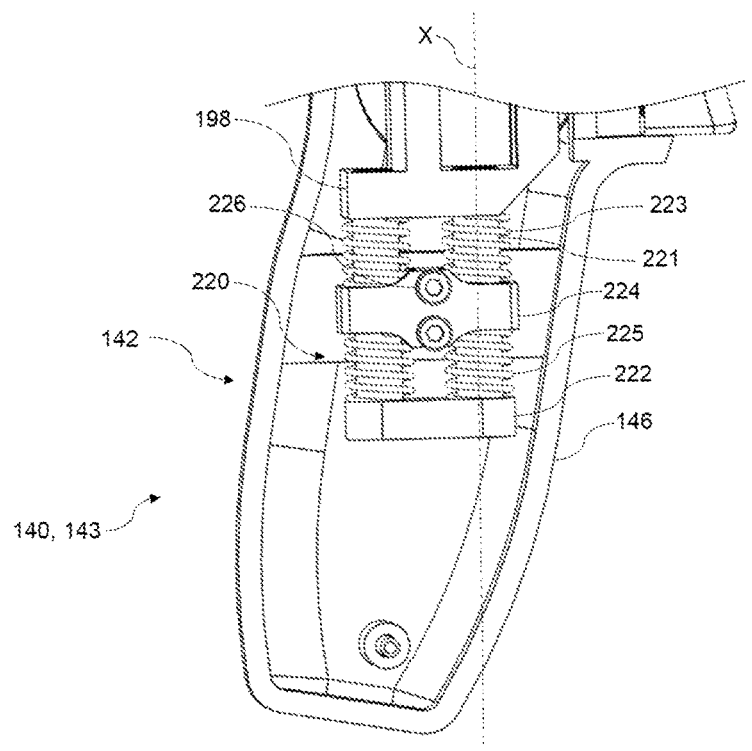
FIG. 14 illustrates a mechanical apparatus housed in a gripping part of the handle's housing, FIG. 14 representing a partial view of such gripping part, without some part of the handle's housing so as to make visible said mechanical apparatus.

As illustrated on FIGS. 2 and 14, the handle 140 generally extends along a main axis of extension X.

The handle 140 comprises a housing 142 which houses at least part of the movable part. According to the invention, the handle 140 comprises at least one gripping part 143 adapted to be held by a user's hand and at least one fixing part 144 adapted to be fixed to the robotic arm of the system. This fixing part 144 is fixed in position with respect to the surgical tool, whether they are attached to the same segment of the robotic arm or not. According to the illustrated embodiment, the gripping part 143 and the fixing part 144 are formed by different parts of the housing 142. As detailed below, the handle may also contain several buttons to control various modes of the system that can be activated with a finger or a thumb depending on the position of the concerned switch with respect to the handle 140.

In order to provide a more ergonomic handle 140, the gripping part 143 presents an upper part 245 which mainly extends along the handle's main axis of extension X and a lower part 246 which mainly extends along a straight-line D, an angle α formed between the handle's main axis of extension X and the lower part's main axis of extension D being comprised between 0° and 45°. Advantageously, this angle α is lower than 20°. Even more advantageously, this angle α is equal to 10°. Optionally, the handle gripping part 143 can present another angle, measured in a plane perpendicular to the main axis of extension X of the handle 140, also comprised between 0° and 45°.

Figure 3:
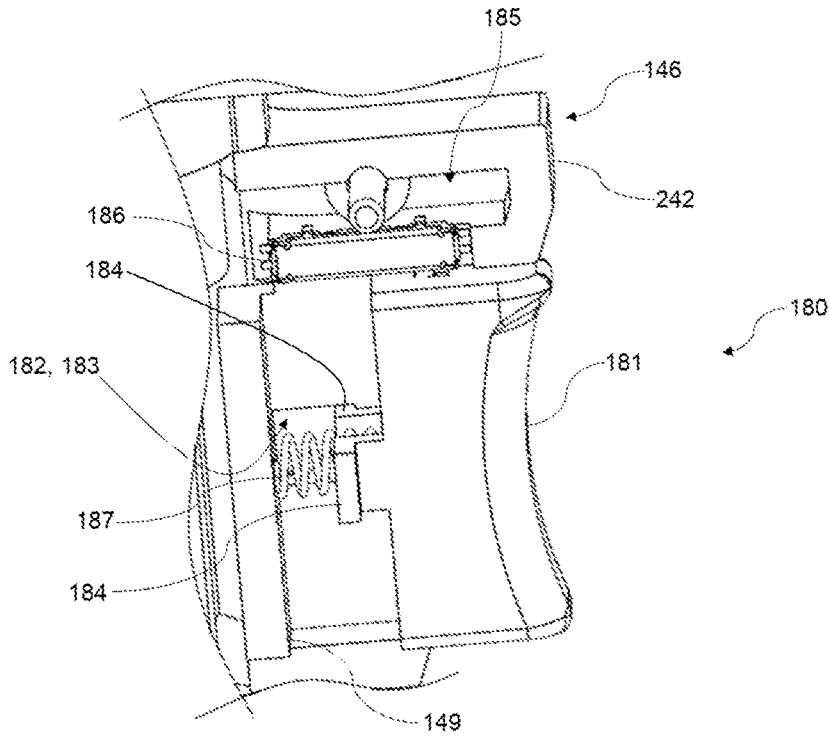
FIG. 3 is an enlarged view of an activation mechanism arranged on the handle of the computer-assisted surgery system.

According to the illustrated embodiment, the housing 142 comprises a right part 145, a left part 146—for instance referenced on FIG. 3 and on FIGS. 14 to 17—and a top part 147, an assembly of the right part 145 with the left part 146 forming the gripping part 143 of the handle 140 and the top part 147 forming the fixing part 144 of such handle 140. The right part 145 and the left part 146 are attached to one another. The attachment of those parts 145, 146 can be realized by any known fixation means 148, such as screws, plastic clips, or rivets. Alternately, the attachment of those parts 145, 146 can be realized thanks to ultrasonic welding, or glue for instance. The gripping part 143 thus presents at least two large faces linked to each other with two small faces 149, 240, the small faces 149, 240 being formed by the junction between the right part 145 and the left part 146. In the following description, a first small face is referred to as the housing's "front part 149" and a second small face is referred to as the housing's "rear part 240".

The handle 140 also comprises at least one activation mechanism 180 adapted to control, at least, one working parameter of the surgical tool. According to the embodiments illustrated, the activation mechanism 180 is formed as a finger activated button 181, acting as a trigger or as a variable command. FIG. 3 more particularly focuses on this finger activated button 181 and represents an enlarged view of the portion of the handle which encompasses the activation mechanism 180, such portion of the handle being represented without the housing's right part.

As shown on this FIG. 3, this finger activated button 181 is mounted on a rail 182 which comprises at least one slit 183 cut in the handle's housing. Especially, each of the right part 145 and of the left part 146 comprises at least one protrusion 241, 242 which extends from the handle's front part 149, away from the handle's gripping part 143, at least one slit 183 being formed in each of those protrusions 241, 242, and those two slits 183 forming the rail 182 along which the finger activated button 181 can be displaced. Especially, the slits 183 are cut in an internal face of the concerned housing's part, that is to say a face of the housing which faces the finger activated button 181.

The finger activated button 181 comprises at least one projection 184 adapted to be received in one of the slits 183. Advantageously, the finger activated button 181 comprises two projections 184, respectively adapted to be received in one of the slits 183. The slits 183 thus form a guiding means for the finger activated button 181, and especially for the projections of such finger activated button 181.

According to a non-illustrated embodiment, the rail can be formed as an added piece which can for instance be glued or screwed in the handle's housing, and especially to the internal faces of the protrusions of such housing.

We also note that the assembly of the protrusions 241, 242 forms a compartment 185 which receives a movement sensor 186 connected to the finger activated button 181. This movement sensor 186 is adapted to detect a movement of the finger activated button 181 and to send a corresponding information to the control unit of the system.

The movement sensor 186 can also be adapted to measure the finger activated button's displacement and to send a corresponding information to the control unit. For instance, the quantified displacement of the finger activated button can be related to the at least one working parameter of the surgical tool requested by the user. The working parameter of the surgical tool can for instance be its working speed. The words "working speed" here refer to a speed at which the surgical tool performs the treatment. For instance, if the surgical tool comprises a burr mounted on a drill, its working speed corresponds to a speed at which the burr rotates. If the surgical tool comprises an oscillating saw, its working speed corresponds to a speed at which the saw oscillates. According to the illustrated embodiment, such working parameter can be monitored by measuring a length of the finger activated button's movement along the rail. For instance, the longer the movement is the faster the user wants the surgical tool to work, such movement being detectable and measurable by the movement sensor 186 mentioned above. For example, this movement sensor 186 can be a potentiometer. Alternately, this movement sensor could be a magnetic sensor or an optical sensor within the scope of the invention. According to a non-illustrated embodiment, the working parameter can be monitored by measuring a force exerted on the finger activated button. As detailed hereafter, the information related to the working parameter is sent to the control unit which will consider such requested working parameter in the computing of the instruction(s) to be given to the motorized joint(s). The activation mechanism 180 can thus be adapted to convey an information related to the working speed the user wishes the surgical tool 130 to reach.

Of course, other working parameter(s) can be controlled by the activation mechanism 180. Optionally, this activation mechanism 180 can form a means which permits the user to communicate with the human-machine interface of the system. Alternately, or cumulatively, this activation mechanism can be used to control a displacement speed of the motorized joints, for instance, when the surgical tool is not in use. The surgical tool can be deactivated when a collaborative mode or when a pre-operative mode is selected by the user of the system. Such collaborative mode and pre-operative mode are described below.

According to the illustrated embodiment, at least one elastic return device 187 is arranged behind the finger activated button 181, that is to say between the finger activated button 181 and the front face 149 of the handle's housing 142. This elastic return device 187 can for instance be a spring and it permits the finger activated button 181 to recover its original position when the user does not apply any displacement on it.

Obviously, the activation mechanism 180 could take another shape than a finger activated button within the scope of the invention. For instance, this activation mechanism could be a voice command, or a knob and it could be arranged on any other part of the system.

Referring back to FIG. 2, the handle's housing 142, and especially the rear part 240 of this housing 142, also comprises at least one manually activated device 247. According to the illustrated embodiment, this manually activated device 247 is realized as a switch but it could be realized according to any other shape within the scope of the invention. For instance, this manually activated device 247 could be a joystick. This manually activated device 247 can be adapted to control different inputs to be sent to the control unit 300. This manually activated device 247 can permit the user to interact with the system, or with the human-machine interface of such system. For instance, the manually activated device 247 can be used to indicate that a first phase of the planned treatment is completed, and that the user is ready to move to the second phase of such planned treatment. Alternately, this manually activated device 247 can be adapted to modify the set of operative degrees of freedom of the handle's movable part. More details will be given about this manually activated device 247 below.

Figure 4:
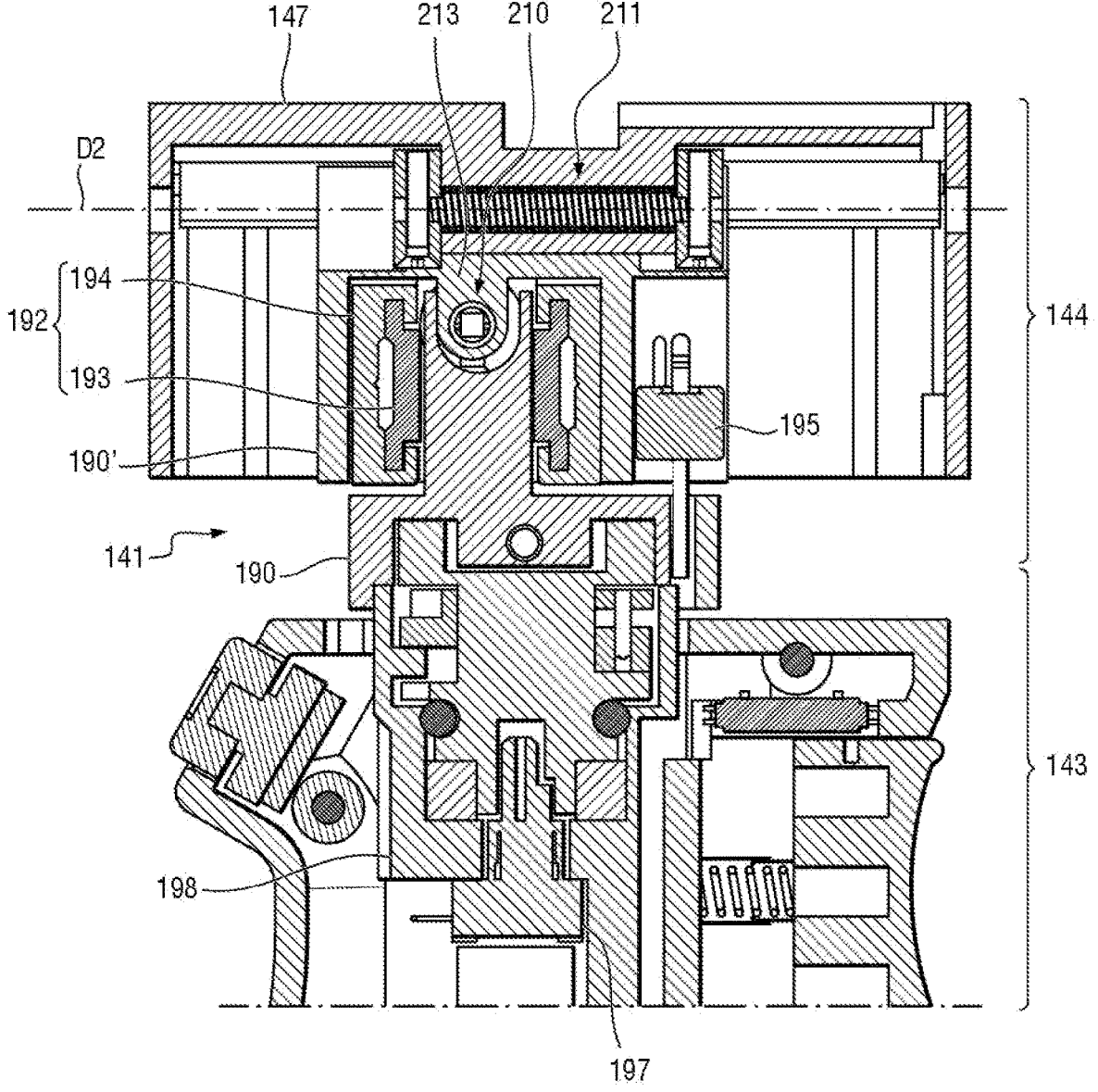
FIGS. 4 and 5 illustrate, partially, in a cross-section views, the handle of the computer-assisted surgery system according to the first embodiment and represented without some parts of its housing, the cross-section views being realized according to two perpendicular planes which include a main axis of extension of the handle.
Figure 5:
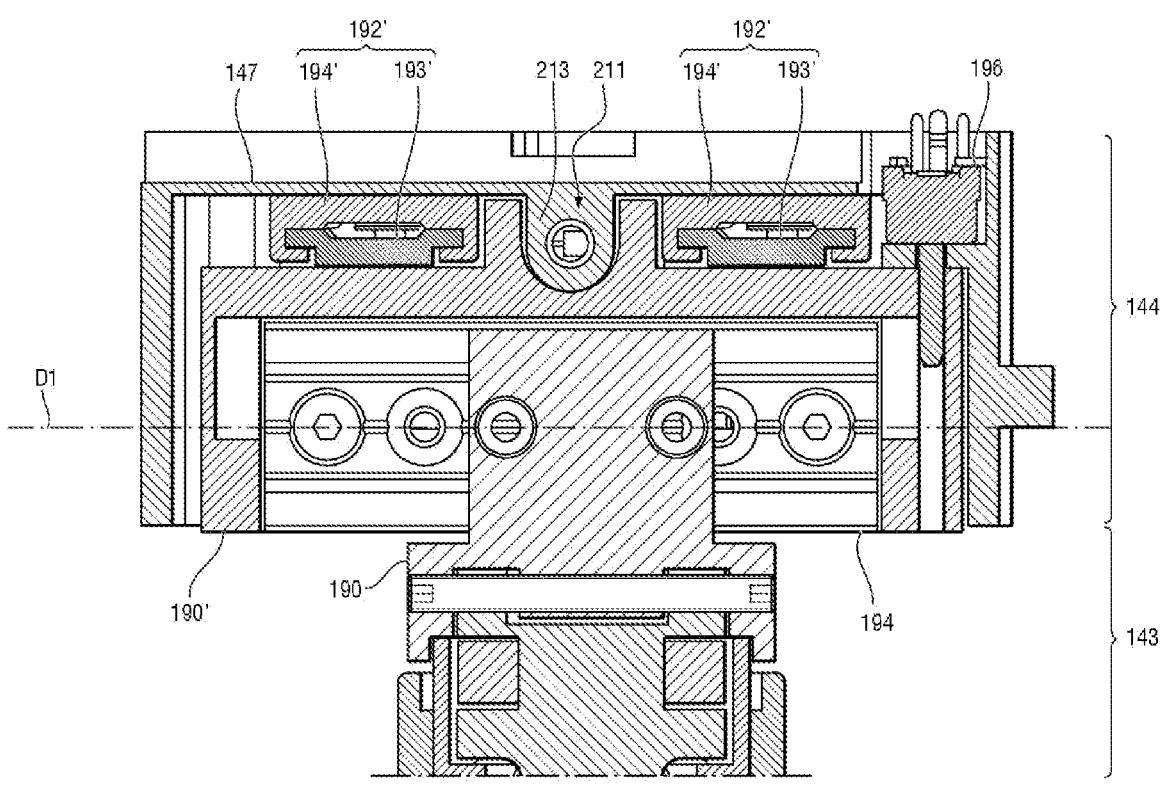
Figure 6:
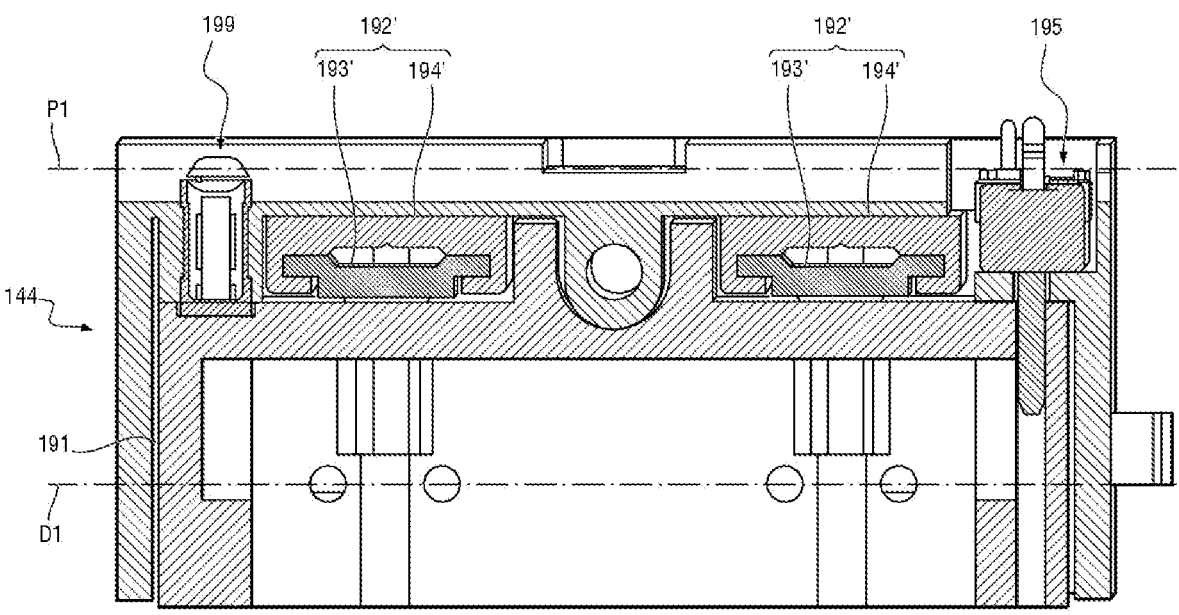
FIG. 6 is a cross-section view of a fixing part of the handle according to a variant of the first embodiment illustrated on FIGS. 4 and 5.
Figure 7:
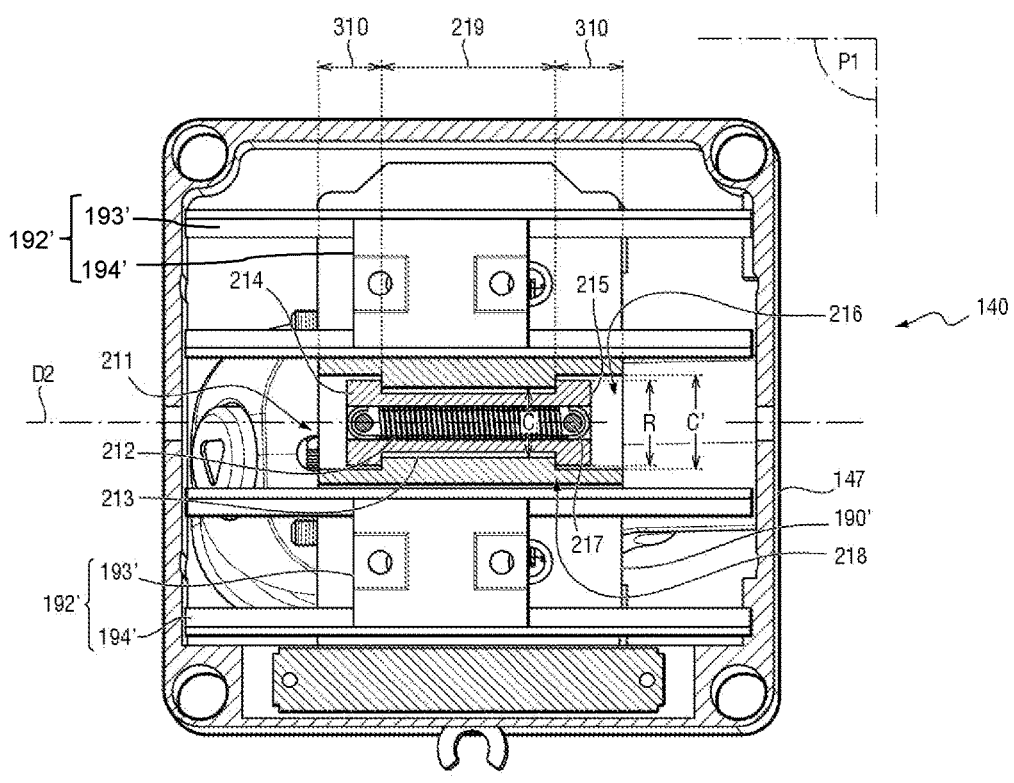
FIG. 7 is a cross-section view of a top part of the handle's housing, this cross-section view being illustrated as a top view of said handle according to the first embodiment.
Figure 8:
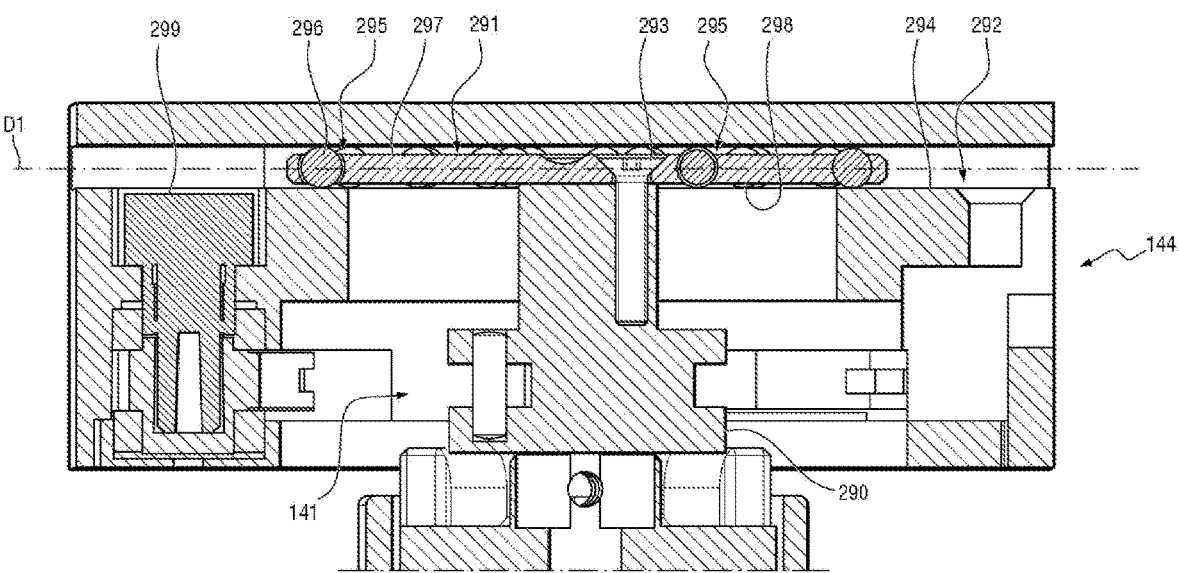
FIG. 8 is a cross-section view of the fixing part of the handle according to a second embodiment of the invention.
Figure 9:
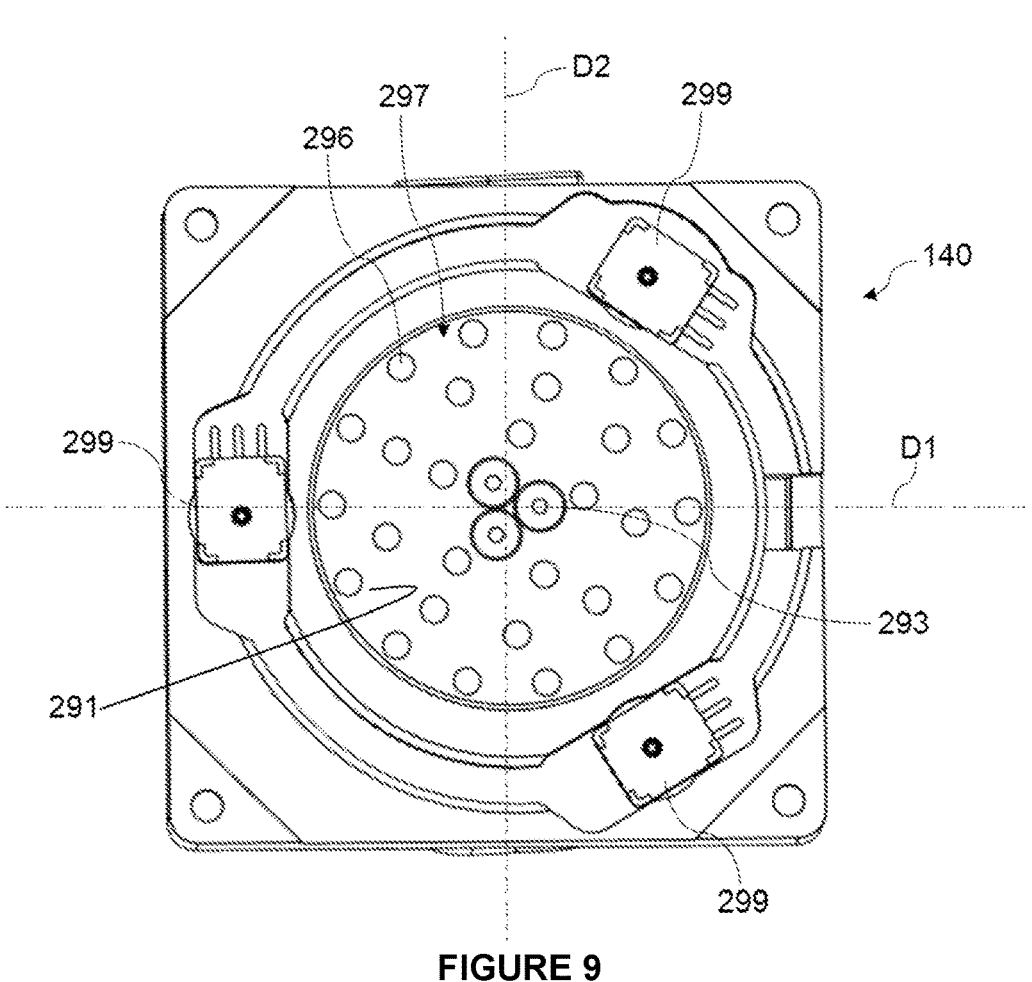
FIG. 9 is a top view of the handle according to the second embodiment of the invention.
Figure 10:
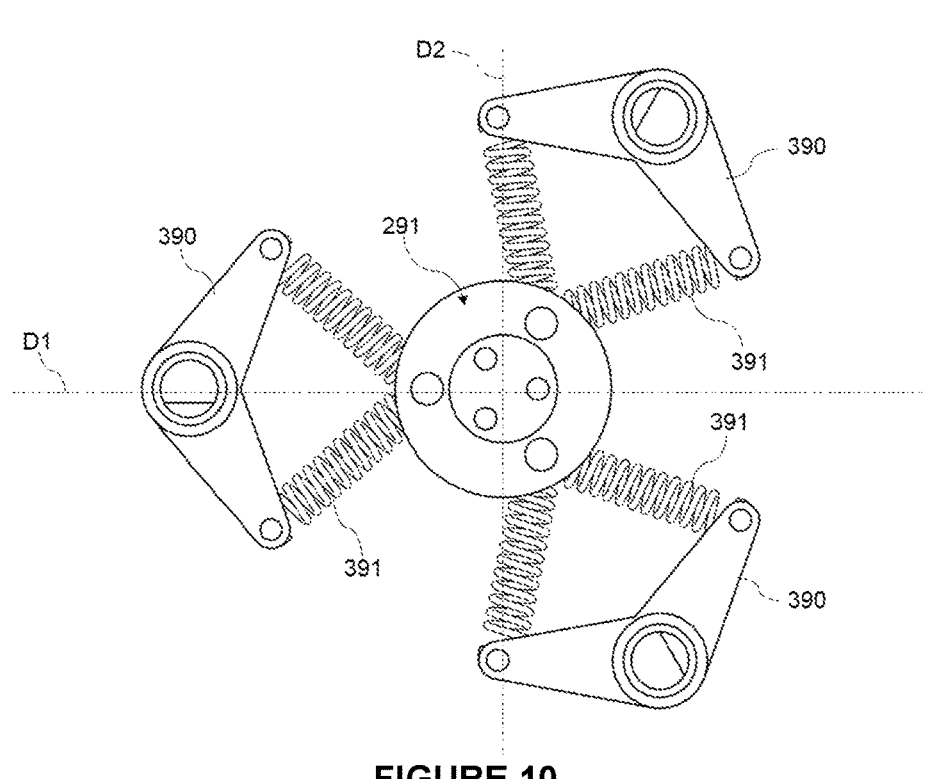
FIG. 10 is a partial top view of a movable part of the handle according to the second embodiment of the invention.
Figure 11:
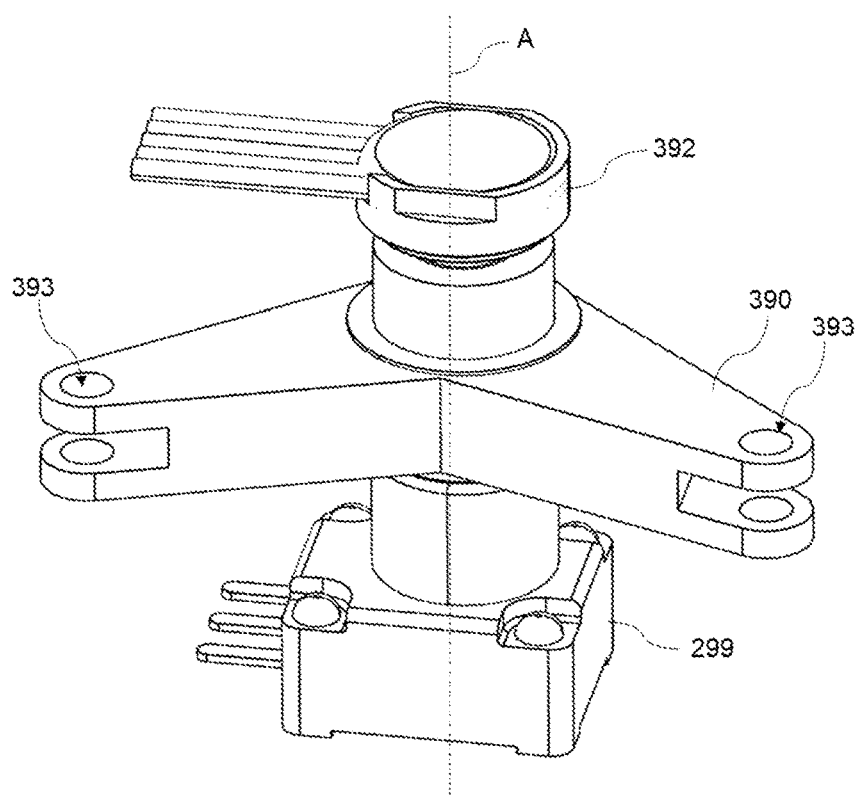
FIG. 11 is a perspective view of a pivoting piece of the handle movable part according to a variant of the second embodiment.
Figure 12:
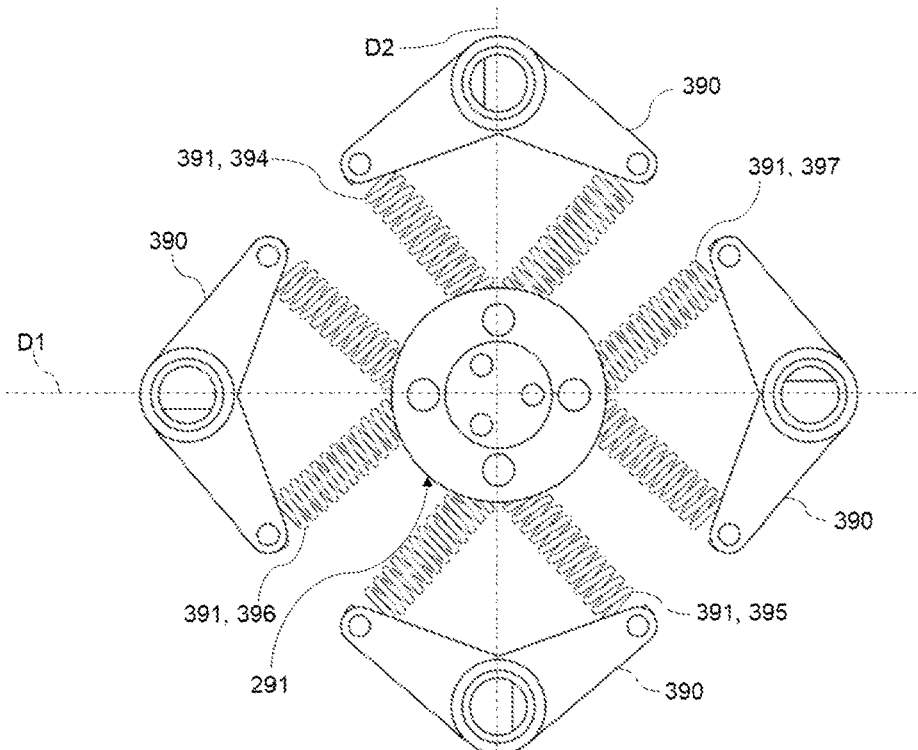
FIG. 12 is a top view of the movable part of the handle according to another variant of the second embodiment.
Figure 13:
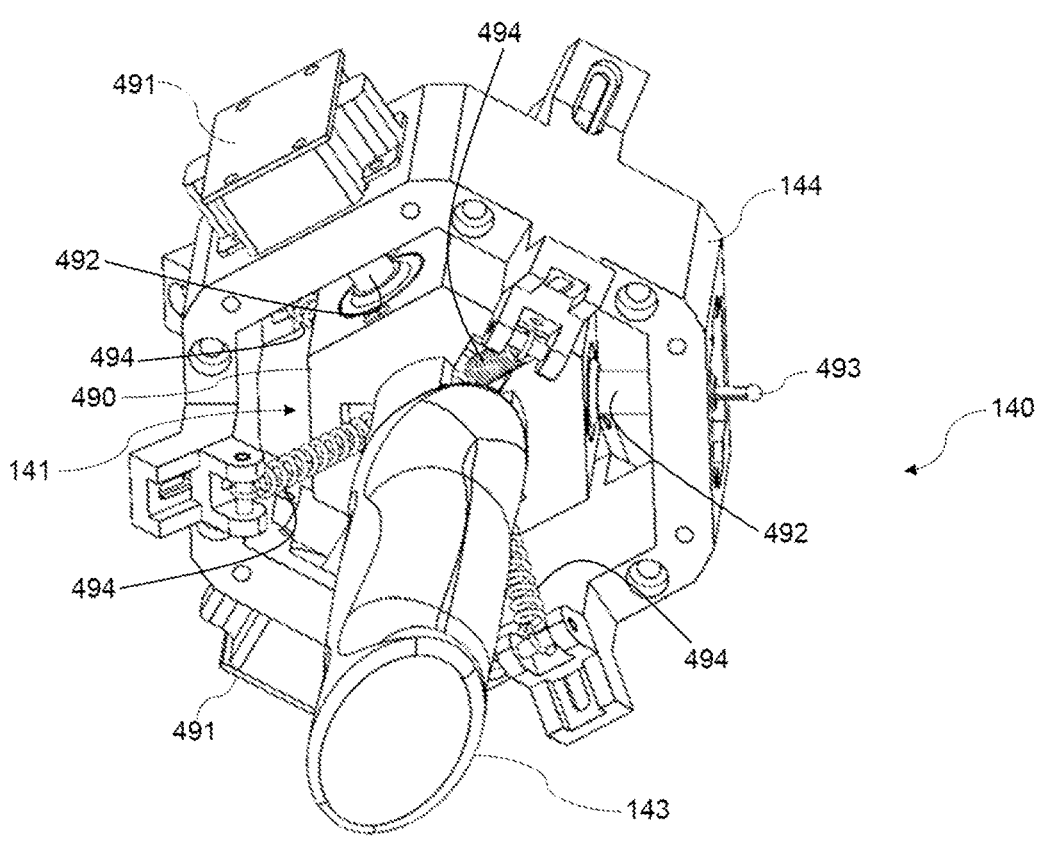
FIG. 13 is a perspective view of the handle according to a third embodiment of the invention.

FIGS. 4 to 5 and 7 illustrate the handle 140 according to a first embodiment of the invention, FIG. 6 illustrates a variant of this first embodiment, FIGS. 8 to 10 illustrate the handle 140 according to a second embodiment of the invention, FIGS. 11 and 12 illustrate variants of this second embodiment and FIG. 13 illustrates the handle 140 according to a third embodiment of the invention. According to any of those embodiments, the handle movable part 141 comprises at least one carriage 190, 190', 290, 490 adapted to be displaced, relative to the handle fixing part 144, in a first plane P1 parallel, or coincident, with a second plane P2 in which the surgical tool mainly extends. The first plane P1 is for instance represented on FIGS. 6, 7 and 28, and the second plane P2 is for instance illustrated on FIGS. 28 and 29.

Now referring to FIGS. 4 and 5, we are going to describe the movable part 141 of the handle 140 according to the first embodiment of the invention, FIGS. 4 and 5 illustrating cross-section views of the handle's fixing part 144 realized according to planes wherein the main axis of extension of the handle extends. FIG. 4 is more particularly a cross-section view realized according to a plane which includes the handle's main axis of extension and FIG. 5 is more particularly a cross-section view realized according to a different plane which includes the handle's main axis of extension, those cross-section planes being perpendicular to each other and also perpendicular to the first plane P1 as represented on FIG. 7.

According to the first embodiment, the movable part 141 comprises at least a first carriage 190 adapted to be displaced along a first direction D1 and at least a second carriage 190' adapted to be displaced along a second direction D2 perpendicular to the first direction D1. The first direction D1 is illustrated on FIG. 5 while the second direction D2 is illustrated on FIGS. 4 and 7. As mentioned above, the first direction D1 and the second direction D2 are both included in the first plane P1 in which the surgical tool 130 mainly extends. In the following specification, the second direction D2 is also referred to as "plunging direction D2". According to the illustrated embodiments, the second direction D2 is parallel to the main axis of extension of the surgical tool.

Each of these carriages 190, 190' is provided with at least one linear guiding device 192, 192'. Each of those linear guiding devices 192, 192' comprises at least one guided portion 193, 193' and at least one linear guiding portion 194, 194', the guided portion 193, 193' being attached to the corresponding carriage 190, 190' and the guided portion 193, 193' being adapted to be displaced along the linear guiding portion 194, 194'. According to the illustrated embodiment, each linear guiding device 192, 192' comprises two linear guiding portions 194, 194' which are formed as rails and two guided portions 193, 193' which respectively engages in one of the guiding portions 194, 194' of the corresponding linear guiding device 192, 192'. Especially, FIG. 4 illustrates the linear guiding device 192 associated with the first carriage 190 while the linear guiding device 192' associated with the second carriage 190' is more particularly shown on FIGS. 5 and 6.

Alternately, the linear guiding portions could be shaped as rods and the guided portions could be shaped as hollow cylinders arranged around said rods within the scope of the invention. According to another alternative, each linear guiding device can comprise ball bearing tracks. Obviously, the linear guiding devices could take any other shapes as long as they encompass all the functional features described in the present document.

As shown on FIGS. 4 and 5, the handle 140 further comprises at least one displacement sensor 195, 196, 197 adapted to measure a displacement applied on the handle 140, that is to say to detect such a displacement and to measure it. Especially, according to the illustrated embodiment, the handle 140 comprises three displacement sensors 195, 196, 197, two of them being housed in the handle's fixing part 144 and the other one being housed in the handle's gripping part 143—only partially represented on FIGS. 4 and 5. According to the illustrated embodiment, a first displacement sensor 195 and a second displacement sensor 196 are both translational displacement sensors and form the two displacement sensors housed in the handle's fixing part 144 while a third displacement sensor 197 is a rotational displacement sensor and is housed in the gripping part 143. Especially, this third displacement sensor 197 is housed in a dedicated casing 198—only partially shown on FIG. 4—itself housed in the handle's gripping part 143. Obviously, this is only an example of the invention, and the displacement sensors could all be housed in the fixing part of the handle within the scope of the invention. All those displacement sensors can for instance be realized as potentiometers, optical sensors or magnetic sensors. Magnetic displacement sensing may be based of quasi-static magnetic field sensing such as from the field generated from a magnet, like as hall effect sensors, magnetoresistance sensors, fluxgate sensors or else. Magnetic displacement sensing may also be based on variable field generation and sensing, such as inductive coupling type, single axis coil coupling, multiple degree of freedom coil coupling. Linear Variable Differential Transformer sensors are for instance of this later type. Other combinations of single or multiple axis field generation and magnetic sensing may be used without departing from the scope of the invention.

As shown on FIG. 4, the first carriage 190 is connected to the first displacement sensor 195 while, as shown on FIG. 5, the second carriage 190' is connected to the second displacement sensor 196. Consequently, the first displacement sensor 195 is adapted to detect and quantify the displacements applied on the handle along the first direction D1 while the second displacement sensor 196 is adapted to detect and quantify the displacements applied on the handle along the second direction D2.

Using the linear guiding devices 192, 192' as described above results in a more ergonomic handle 140. Indeed, thanks to the use of such linear guiding devices 192, 192' the relations between the handle's displacements and the displacements of the handle's movable part are linear. Consequently, if the user wants to move the surgical tool along a translational direction, he/she must move the handle 140 along the same translational direction, thus improving the intuitiveness and the user-friendliness of the system. This configuration aims to make the user feel like he/she is actually directing the requested treatment. Such a configuration aims at making the use of the system 100 transparent for the user.

As detailed after, when the computer-assisted surgery system comprises several displacement sensors, each of them can be independently activated or deactivated.

The handle also encompasses one rotational displacement sensor 197, illustrated on FIG. 4. This rotational displacement sensor 197 is fixed in translation with respect to the first carriage 190, and this rotational sensor 197 is connected to the handle's gripping part 143. The user who wishes to rotate the surgical tool must rotate the handle, and especially the gripping part 143 of this handle 140 so as for the third displacement sensor 197 to detect and measure said rotation and to transmit a corresponding information to the control unit of the system. The connection between the third displacement sensor 197 and the handle's gripping part 143 is realized so that when a clockwise rotation is applied to the handle's gripping part 143, an instruction to rotate the surgical tool clockwise is calculated by the control unit of the system. According to the first embodiment illustrated on FIGS. 4 and 5, it is thus understood that the handle's gripping part 143 is also part of the handle movable part 141, thus providing intuitiveness and user-friendliness to the system.

FIG. 6 illustrates, partially, the fixing part 144 of the handle according to a variant of the first embodiment. FIG. 6 is a simplified representation of the fixing part 144 which only illustrates the second carriage 190' and the associated linear guiding devices 192'. According to this variant of the first embodiment, at least one of the degrees of freedom is monitored by two independent displacement sensors 195, 199. According to the illustrated variant of the first embodiment, the second carriage 190' is thus connected to the first displacement sensor 195 mentioned above and to another displacement sensor 199 which forms a redundant displacement sensor, that is to say that this other displacement sensor 199 is adapted to monitor the same degree of freedom as the first displacement sensor 195. Here, the expression "the displacement sensor is adapted to monitor at least one degree of freedom" must be understood as "the displacement sensor is adapted to detect and quantify the displacements of the handle movable part along at least one degree of freedom". This definition applies in all the present document.

According to the illustrated variant, the first displacement sensor 195 and the redundant displacement sensor 199 are of two different kinds, the first displacement sensor 195 being realized as a potentiometer and the redundant displacement sensor 199 being realized as a magnetic sensor. Obviously, this is only an example and those displacement sensors could be identical within the scope of the invention. Alternately, at least one of those displacement sensors could also be realized as an optical sensor.

It is understood that a redundant displacement sensor can be associated to each displacement sensor described above. In other words, the first carriage could be connected to the second displacement sensor and to a redundant displacement sensor, identical to the second displacement sensor or of another kind within the scope of the invention. Also, the handle could encompass the rotational displacement sensor mentioned above and also another rotational displacement sensor—also referred to as "redundant rotational displacement sensor"—adapted to monitor the same degree of freedom. The handle which comprises three degrees of freedom can thus comprise up to six displacement sensors, each degree of freedom being adapted to be monitored, independently, by two of these displacement sensors. Consequently, the handle can, for instance, comprise four translational displacement sensors and two rotational displacement sensors.

This feature of the variant of the first embodiment provides a safer handle especially adapted to be used for performing surgeries. Indeed, for each degree of freedom, the displacements detected and measured by each displacement sensor can be compared in real-time, thus permitting to detect any dysfunction of said displacement sensors and to detect if one of them stops working. If one of the displacement sensors stops working, at least one other displacement sensor can take over the monitoring of the concerned degree of freedom. Alternatively, if one of the displacement sensors stops working or if a dysfunction is detected, at least one of these displacement sensors can be adapted to transmit a corresponding information to the control unit instead of the information related to the detected and measured displacement.

Alternately, each degree of freedom can be adapted to be monitored by one dedicated displacement sensor and by one additional displacement sensor adapted to monitor all the degrees of freedom. The advantages of such alternative are identical to the ones that have just been described. Additionally, this alternative is cheaper as it implements a smaller number of displacement sensors.

The handle 140 further comprises at least one security device 210, 211. According to the first embodiment, the handle 140 comprises two security devices 210, a first security device 210 being associated with the first carriage 190 and a second security device 211 being associated with the second carriage 190'. Those security devices 210, 211 are identical and the description of the second security device 211 given hereunder with reference to FIG. 7 applies mutatis mutandis to the first security device 210, unless otherwise specified. As detailed below, those security devices are adapted to counter a weight of the handle and thus to keep the handle movable part in a neutral position, that is to say a position in which no displacement is detected by the displacement sensor(s) or a position wherein the displacement detected is below a defined value.

Especially, FIG. 7 is a cross-sectional top view of the handle, the cross-section being realized according to a plane perpendicular to the handle's main axis of extension.

As shown, the security device 211 comprises at least one elastic return means 212 received in a tunnel 213. According to the illustrated embodiment, the tunnel 213 receiving the second security device 211 is formed as a part of the housing's top part 147 and the elastic return means 212 is realized as a spring. Therefore, the tunnel 213 and the housing's top part 147 cannot be separated without damaging at least the tunnel 213 of the housing's top part 147. This tunnel 213 can for instance be seen on FIG. 5. As shown on FIG. 4, the tunnel 213 which receives the spring of the first security device 210 is formed, in a similar way, as a part of the second carriage 190'.

The security device 211 also comprises at least two rings 214, 215 respectively arranged at each end of the tunnel 213. The tunnel 213 and the rings 214, 215 are received in a channel 216 formed in the second carriage 190', and especially in an upper face of this second carriage 190', that is to say a face of this second carriage which faces the housing's top part 147. This channel 216 is an open channel adapted to be closed by the housing's top part 147.

The rings 214, 215 are mobile in the channel 216. A rod 217, here realized as a screw, crosses each of these rings 214, 216. As shown, those rods 217 provide support for the spring 212. The wall defining the channel 216 comprises a shoulder 218 centered along the length of the channel 216. A central portion 219 of the channel 216, formed by said shoulder 218, thus presents a smaller diameter than external portions 310 of such channel 216, those external portions 310 being arranged on both sides of the central portion 219.

We also note that the rings 214, 215 both present an external diameter R greater than an internal diameter C of channel's central portion 219, such external diameter R of the rings 214, 215 being smaller than an internal diameter C' of the channel's external portions 310. Consequently, each ring 214, 215 is adapted to move freely in one of the external portions 310 of the channel 216 and each ring 214, 215 is also adapted to abut the shoulder 218. The central portion 219 of the channel 216 is adapted to receive the tunnel 213 receiving the spring 212 and to constraint the movements of the rings 214, 215.

Finally, FIG. 7 also illustrates the second carriage 190' and one of the associated linear guiding devices 192'. According to the illustrated embodiment, the second security device 211 is arranged between the two linear guiding portions 194' and between the corresponding guided portions 193'.

The security devices 210, 211, and especially the elastic return means 212 of such security devices 210, 211, participate to ensure that the detected displacements are willingly applied on the handle 140 and, in this case, that such detected displacements do not result from an unwanted sliding of the carriages along the corresponding linear guiding devices. Indeed, it is understood from the foregoing that when one of the carriages is displaced, a first ring 214 abuts against the channel's shoulder 218 while a second ring 215 is displaced away from this shoulder 218. Due to its intrinsic features, the spring 212 tends to recover its original position, thus tending to bring back the second ring 215 against said shoulder 218. Obviously, the words "first ring" and "second ring" are here used for the sake of clarity but are arbitrarily given.

Moreover, the elastic return means 212 of at least one of the security devices 210, 211 can be preloaded at a force greater than a weight of the handle 140. The word "weight" here must be understood as referring to the force acting on the handle, due to gravity in any spatial orientation. This weight can thus be calculated by multiplying the mass of the handle 140 by the gravitational constant. The elastic return means 212 of both security devices 210, 211 can be pre-loaded at least at such a force, thus preventing that the movable part 141, and especially the carriages of such movable part 141, to be dragged away by said weight. These preloads permit to counter the gravitational force and thus permits to keep the carriages in their neutral positions in the absence of user-imposed displacement.

Therefore, if one of the carriages tends to slide along the corresponding linear guiding devices, on its own, for instance due to its own weight, the elastic return means of the corresponding security device, preloaded at neutral position, counters such sliding, thus preventing the corresponding displacement sensor to detect and measure a displacement unwillingly applied on said carriage. In contrast, if the displacement of the carriage is realized by the user of the system, he/she must apply a force sufficient to exceed to preload force of the spring. The detected displacements are therefore only those which are willingly applied on the handle.

Those security devices 210, 211, and especially the elastic return means 212 of such security devices 210, 211 also participate to the user-friendliness of the handle. Indeed, if the user wants to displace the first carriage 190 along the first direction D1, the second security device 211 associated with the second carriage 190' will resist against any displacement along the second direction D2 which could result from an imprecision of the displacement applied by the user. In a similar way, if the user wants to displace the second carriage 190' along the second direction D2, the first security device 210 associated with the first carriage 190 will resist against any displacement along the first direction D1 which could result from an imprecision of the displacement applied by the user. As previously mentioned, the user of the system must apply a force that exceeds the preload force of the spring.

Optionally, the elastic return means of the first security device and the elastic return means of the second security device can present different level of stiffnesses, thus providing a different sensation to the user depending on the axis along which he/she displaces the handle movable part. The different level of stiffnesses can for instance be chosen depending on the kind of treatment to be performed with the computer-assisted surgery system of the invention or on the kind of surgical tool used. For instance, if the surgical tool is an oscillating saw or respectively a drill bit, adapted to perform cutting only along one defined direction, for instance along the second direction D2, the elastic return means of the first security device 210 associated with the first carriage 190 can present a higher level of stiffness than the elastic return means of the second security device 211 associated with the second carriage 190'. The difference of stiffness of the elastic return means thus encourages the user to displace the handle along the plunging direction D2, by making such displacement easier than a displacement along the second direction D1.

Now referring to FIGS. 8 to 10, we are going to describe the second embodiment of the handle 140. FIG. 8 illustrates a cross-section view of the fixing part 144 realized according to a plan in which the main axis of extension of the handle extends.

According to this second embodiment, the movable part 141 comprises a unique carriage 290 mechanically connected to a plate 291 supported by a planar base 292, the plate 291 being adapted to slide in a plane, on such planar base 292. According to the illustrated embodiment, the mechanical connection is realized thanks to at least one screw 293, thanks to several screws. Obviously, this mechanical connection could be realized by any other known fixation means, or the plate could be formed as a single piece with the carriage without departing from the scope of the invention.

The planar base 292 is more particularly formed as an upper face of a hollow cylinder 294, the carriage 290 extending, at least partially, through the aperture formed through such hollow cylinder 294.

According to the illustrated second embodiment, the plate 291 associated with the carriage 290 is more particularly a perforated plate, a plurality of holes 295 being formed on this plate 291. Those holes 295 are through-holes and each of them receives a ball 296. The plate 291 thus presents an upper face 297 and a lower face 298, the lower face 298 facing the upper face of the planar base 292 and each ball 295 sticking out on both faces 297, 298 of the plate 291. It is thus understood that at least part of the balls 295 are adapted to roll on the planar base 292 and that their displacement causes a corresponding displacement of the plate 291. According to a non-illustrated embodiment, the plate can be provided with polytetrafluoroethylene dots formed on the lower face of the plate and adapted to slide on said planar base. This non-illustrated embodiment thus differs from the illustrated embodiment in that the plate is deprived of the balls. Any other known sliding means can of course be used to permit the sliding of the plate along the planar base, without departing from the scope of the invention.

FIG. 8 also shows one of the displacement sensors 299 associated with the plate 291. As represented on FIG. 9 which is a top view of the handle according to the second embodiment, this handle 140 encompasses three displacement sensors 299 arranged around the plate 291. According to this particular embodiment, each displacement sensor 299 is thus separated from the two others by a 120° angle. According to the second embodiment of the invention, the displacements of the carriage 290 are monitored through the monitoring of the displacements of at least three points of the plate 291. As illustrated on FIG. 10, the plate 291 is thus linked to three pivoting pieces 390 thanks to elastic return means 391 and each of these pivoting pieces 390, is mechanically connected to one of the displacement sensors. The pivoting pieces 390 are adapted to pivot around an axis. Especially, each of those pivoting pieces 390 present a triangular shape, the axis around which it is adapted to pivot passing through one of the angles of such triangular shape and the corresponding elastic return means 391 being attached to the two other angles of such triangular shape on one hand and to the plate 291 on the other hand.

When the carriage is displaced, consequently to a displacement applied by the user on the handle movable part, all three elastic return means 391 are also displaced and they drag with them the corresponding pivoting piece 390. The displacement sensors 299 associated with these pivoting pieces 390 are thus adapted to detect and measure the applied displacement and then are adapted to send a corresponding information to the control unit of the system. The control unit is thus adapted to separate said information into displacements related to each respective degree of freedom. In other words, the control unit is adapted to determine an intended direction based on the measured displacement. As detailed below, the handle according to the second embodiment can comprise more than three displacement sensors within the scope of the invention, thus providing a safer handle.

In a similar way to what have been described with reference to the first embodiment, at least one of the pivoting pieces 390 can be connected to two displacement sensors 299, 392. Such a variant of the second embodiment is for instance partially illustrated on FIG. 11 which represents a perspective view of one of the pivoting pieces 390 associated with two displacement sensors 299, 392. According to the illustrated embodiment, a first displacement sensor 299 is realized as a potentiometer while a second displacement sensor 392 is realized as a magnetic sensor. Obviously, this is only an example of the invention and both displacement sensors 299, 392 could be of the same kind within the scope of the invention. Alternately, at least one of those displacement sensors 299, 392 could be realized as an optical sensor without departing from the scope of the invention. As for the first embodiment, the use of these two displacement sensors thus permits to compare, in real-time, the displacements detected and measured by each displacement sensor. Such comparison permits to detect any dysfunction of said displacement sensors and to detect if one of them stops working. The additional displacement sensor thus forms a redundant displacement sensor. Obviously, each of the pivoting pieces 390 could be associated with two distinct displacement sensors.

FIG. 11 also illustrates the axis A around which the pivoting piece 390 is adapted to pivot and the two other angles 393 to which the elastic return means 391 is adapted to be attached.

Alternately, the redundance can be realized thanks to a fourth displacement sensor 390 adapted to detect and measure the displacement of a fourth point of the plate, distinct from the three other points monitored by the three other displacement sensors 390. Such a configuration is for instance represented on FIG. 12. FIG. 12 thus represents another variant of the second embodiment of the invention.

According to the examples illustrated on FIGS. 10 and 12, the elastic return means 391 can be preloaded at a force greater than a weight of the handle 140. As previously mentioned, the word "weight" here must be understood as referring to the force acting on the handle, due to gravity. The elastic return means 391 can be preloaded at such a force, when the carriage is in its neutral position, thus preventing the movable part, and especially the carriage of such movable part, to be dragged away by said weight. Those preloads permit to counter the gravitational force. Those elastic return means 391 thus form a security device adapted to urge the carriage to its neutral position and consequently, to prevent unwanted displacements of the carriage, from its neutral position.

According to the variant of the second embodiment illustrated on FIG. 12, the elastic return means 391 can present different levels of stiffnesses, thus providing the user different sensations depending on the direction of the displacement he/she applies on the handle. For instance, a first elastic return means 394 and a second elastic return means 395 arranged along the second direction D2 can present a lower level of stiffness than a third elastic return means 396 and than a fourth elastic return means 397 arranged along the first direction D1. In this configuration, the movements along the second direction D2 are easier than the movements along the first direction D1. According to the illustrated embodiment, the elastic return means 391 are realized as spring but they could be realized as elastic bands within the scope of the invention. Any other known elastic return means could also be used without departing from the scope of the invention.

FIG. 13 finally illustrates a perspective view of a third embodiment of the invention. According to this third embodiment of the invention, the handle movable part 141 comprises one carriage 490 connected to three displacement sensors 491—one of them being hidden on FIG. 13—each displacement sensor 491 being adapted to monitor at least two degrees of freedom. As such, the handle movable part 141 according to the third embodiment of the invention presents six degrees of freedom, upon which three translational degrees of freedom and three rotational degrees of freedom. As shown, the carriage 490 is especially connected to the displacement sensors 491 thanks to shafts 492 with a rounded end 493. One of the displacement sensors is hidden to show such rounded end 493. According to the illustrated embodiment, each displacement sensor 491 is adapted to detect and measure the displacements of the movable part 141 and to send a corresponding information to the control unit which is then adapted to transform such information into separated information related to each respective degree of freedom. In other words, the control unit is adapted to determine an intended direction based on the measured displacement transmitted by the displacement sensors.

The handle according to this third embodiment also encompasses at least one elastic return means 494. According to the illustrated embodiment, the handle especially encompasses six of those elastic return means 494, four of them being visible on FIG. 13. In a similar way to what has been described with reference to the first and second embodiments, those elastic return means 494 aim to prevent unwanted displacements of the carriage 490. They also are adapted to urge the carriage 490 to its neutral position as soon as the user stops applying displacement of the handle. Those elastic return means 494 can be preloaded at a force greater than the weight of the handle. According to the illustrated embodiment, those elastic return means 494 are preferably realized as springs. Alternately, those elastic return means could be realized as elastic bands within the scope of the invention.

According to a variant of this third embodiment, the handle can be provided with four displacement sensors, for instance evenly distributed around the carriage, and with the corresponding eight elastic return means. When four displacement sensors are used, these elastic return means can be provided with different level of stiffnesses, in order to provide the user different sensations depending on the requested displacement, as previously described.

The fourth displacement sensor added in such variant of the third embodiment also forms a redundant displacement sensor which provides a second detection and measure of each of the monitored degrees of freedom. Consequently, the detected and measured displacements can be compared in real-time, thus permitting to detect any dysfunction of said displacement sensors and to detect if one of them stops working.

According to another variant of the third embodiment, the handle can be provided with three displacement sensors as described above and with at least one fourth displacement sensor arranged on an internal face of the fixing part, that is to say a face of such fixing part facing the carriage. This fourth displacement sensor is arranged so as to face one of the three other displacement sensors. Such fourth displacement sensor thus forms a redundant displacement sensor, as described above.

The computer-assisted surgery system 100 is likely in continuous motion, unlike a system using a force/torque sensor, the large stroke and compliant elastic return of the handle 140 to its neutral position thus creating intuitive and explicit hand-eye coordination with respect to an intended direction of displacement. Such hand-eye coordination can be realized, whether in direct sight of the anatomical structure or thanks to displaying localization information provided by the localization unit. It results in easing the control of precise displacements of the surgical tool, even in the presence displacement(s) which can for instance result of an anatomical structure motion, tracked by the localization unit of the system. Additionally, handle displacements are decorrelated from actual force and miscellaneous torque usually needed at hand-held tool grip. As the system absorbs the surgical tool mass, tool surgery generated forces and forces variations, while maintaining the surgical tool position in a reference frame attached to the anatomical structure, the user can focus on tool positioning, dimensional accuracy and workflow optimization without muscle fatigue, thus resulting in reliable results, better patient outcome and shorter surgery time. The forces required to displace the handle movable part against the preloaded elastic return means can thus be made quite small, which limits the additional force or torque needed at the motorized joints for compensation of the such. Handle displacement to tool acceleration, speed of displacement and other parameters can be customized to the user's preference, practice and many other parameters as detailed in the present document.

According to any of the described embodiments, the movable part 141 of the handle 140 can comprise at least one degree of freedom imperceptible for the control unit 300. This imperceptible degree of freedom forms a translational direction or a rotational direction along which the user can move the handle's movable part 141 but along which the control unit 300 does not instruct any movement to the motorized joints, nor to the surgical tool.

The imperceptible degree of freedom can be imperceptible thanks to a deactivation of one of the displacement sensors and/or thanks to a mechanical apparatus. According to the illustrated embodiments, the handle 140 comprises such a mechanical apparatus 220. As shown on FIG. 14, which represents the lower part of the gripping part 143 without the housing's right part, this mechanical apparatus 220 is housed in the handle's gripping part 143.

This mechanical apparatus 220 comprises at least one straight bar 221 which extends between the casing 198 which receives the third displacement sensor and a plate 222 fixed to the handle's housing 142. At least one suspension device 223 is arranged around the straight bar 221. According to the illustrated embodiment, the mechanical apparatus 220 comprises two straight bars 221 extending between the casing 198 and the plate 222. The mechanical apparatus 220 further comprises a support plate 224 in which two holes are arranged, each of the straight bars 221 extending through one of those holes. Two absorbing devices are arranged around each straight bar 221, a first suspension device 223 extending between the casing 198 and the support plate 224 and a second suspension device 225 extending between the support plate 224 and the plate 222. As illustrated, the plate 222 is fixed to the handle's housing 142 through the fixation of the support plate 224 to said housing 142. Especially, at least one fixation means 226, such as a screw, permits to attach the support plate 224 to the housing's left part 146. According to an example of the invention, the suspension devices are realized as springs, but this is only an example which does not restrict the invention.

This mechanical apparatus 220 thus forms a suspension or a damping mechanism thanks to which a displacement applied by the user along a direction parallel to the main axis of extension X of the handle 140 will not be detected by the displacement sensors, and, consequently, will not be considered by the control unit 300. This mechanical apparatus 220 therefore aims to lessen the interfering efforts that the user may pass to the computer-assisted surgery system and, consequently, this mechanical apparatus 220 permits to improve the accuracy of such system.

According to a non-illustrated embodiment, the damping mechanism can comprise a sleeve arranged around the handle's housing and coupled to said housing thanks to a frictionless axial slide. An example of such frictionless axial slide is for instance a ball bearing device. Such a mechanical apparatus thus makes imperceptible a vertical movement. The user can indeed move said sleeve but as this sleeve is not connected to any displacement sensor, no corresponding information is generated and therefore no information is sent to the control unit. Obviously, those are only examples and any other known decoupling mechanical apparatus can be implemented on the handle without departing from the scope of the invention.

As previously mentioned, the system 100 of the invention can comprise a manually activated device 247. According to the invention, this manually activated device 247 can be adapted to modify a set of operative degrees of freedom to be considered by the control unit. For instance, the manually activated device can be adapted to activate and deactivate one or more of the degrees of freedom. For instance, the deactivation of one degree of freedom can be digital, the control unit thus being adapted to not consider the corresponding degree of freedom in the computing of the instructions. Deactivating one or more of the degrees of freedom results in the fact that the corresponding displacement is no longer considered by the control unit which, thus, does not include such displacement in the calculation of the instructions to be sent to the motorized joint(s). According to different embodiments of the invention, the manually activated device can be adapted to allow the user to directly modify the set of operative degrees of freedom or it can be adapted to allow the user to indicate that a phase of the planned treatment is completed and that he/she is ready to move to the next phase, such indication resulting in the modification of the set of operative degrees of freedom. Alternately, the deactivation of one of the degrees of freedom can be a mechanical deactivation, thus preventing any displacement of the handle movable part along the concerned degree of freedom.

As mentioned above, with respect to the third embodiment, the movable part 141 of the handle 140 can present up to six degrees of freedom. Advantageously, a chosen number of them can be deactivated. This manually activated device 247 thus permits to use a single system 100 to perform several distinct treatments. This manually activated device 247 also permits to adapt the system 100 to the ongoing treatment's phase. For instance, if the system 100 is used to perform a bone-cut within a predetermined plane, the system 100 can be used with six degrees of freedom during a first phase wherein the user needs to position the surgical tool 130 within the predetermined plane and the manually activated device can be used to reduce the number of degrees of freedom from six to three during a second phase of the treatment wherein the user needs to remain within such predetermined plane to perform the planned cut. The six degrees of freedom thus permit the user to displace the robotic arm, through the handle, during the first phase and then to use the same handle, with a fewer number of degrees of freedom to perform the planned treatment.

During the second phase, three of the six degrees of freedom are thus deactivated, therefore three of the six degrees of freedom are not considered by the control unit 300. Of course, it is only an example of application of the invention and the manually activated device is adapted to activate and deactivate, independently, each of the six degrees of freedom.

Figure 15:
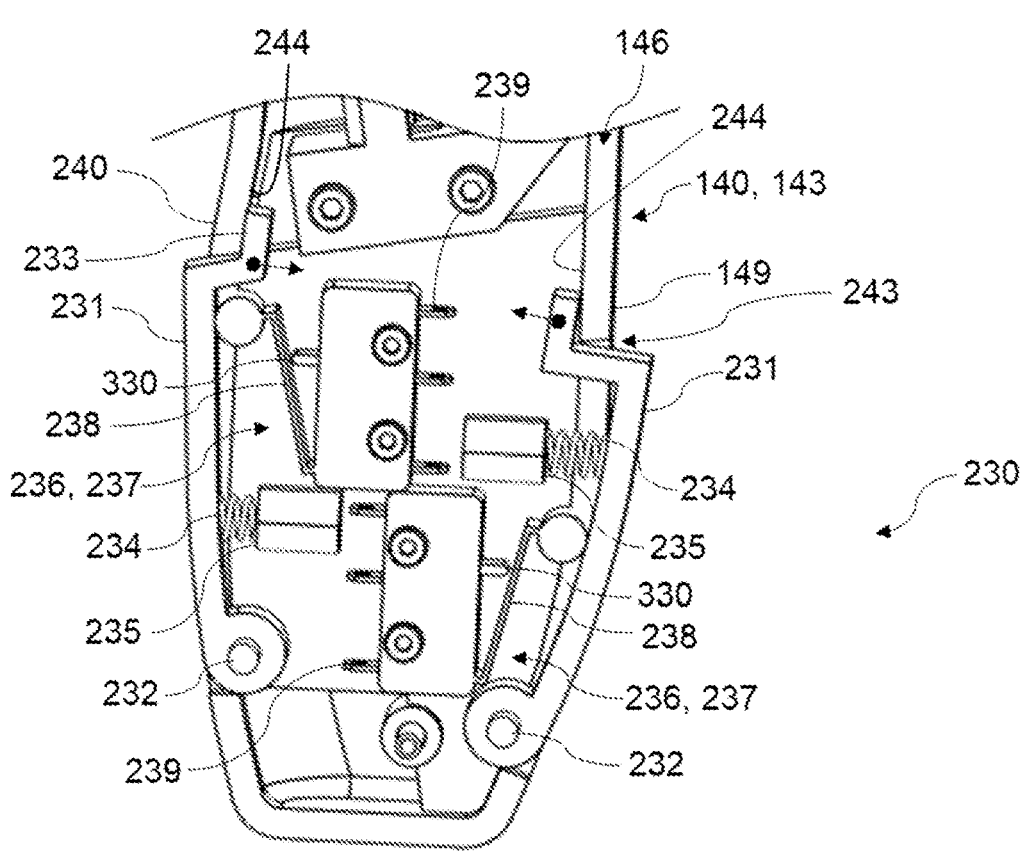
FIGS. 15 and 16 illustrate a first embodiment of a detecting device housed in the housing's gripping part, FIGS. 15 and 16 representing a partial view of such gripping part, without some part of the handle's housing so as to make visible said detecting device.
Figure 16:
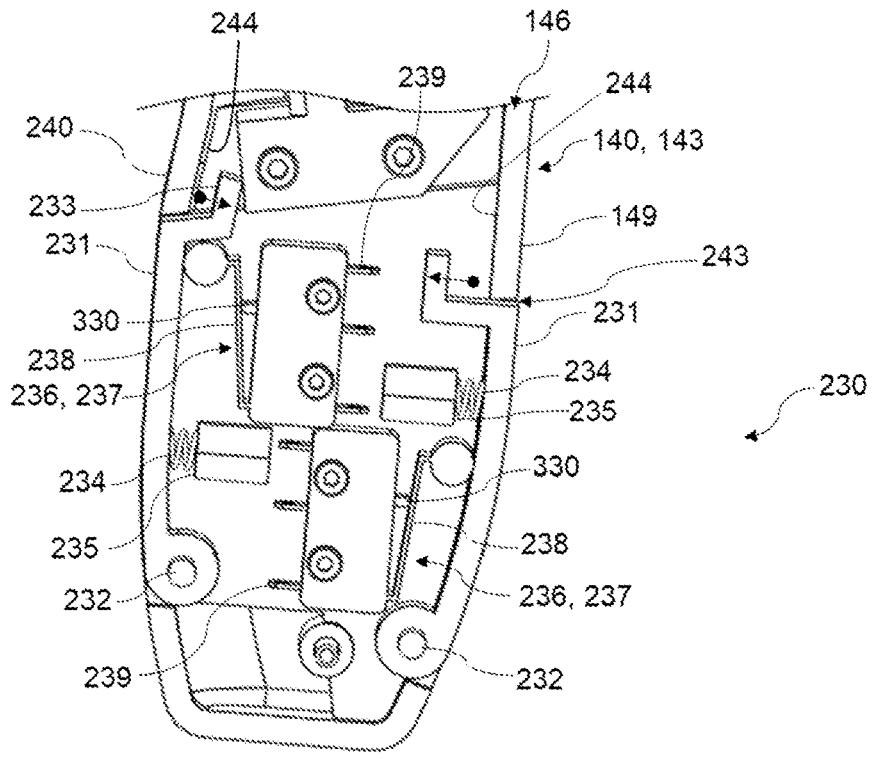
Figure 17:
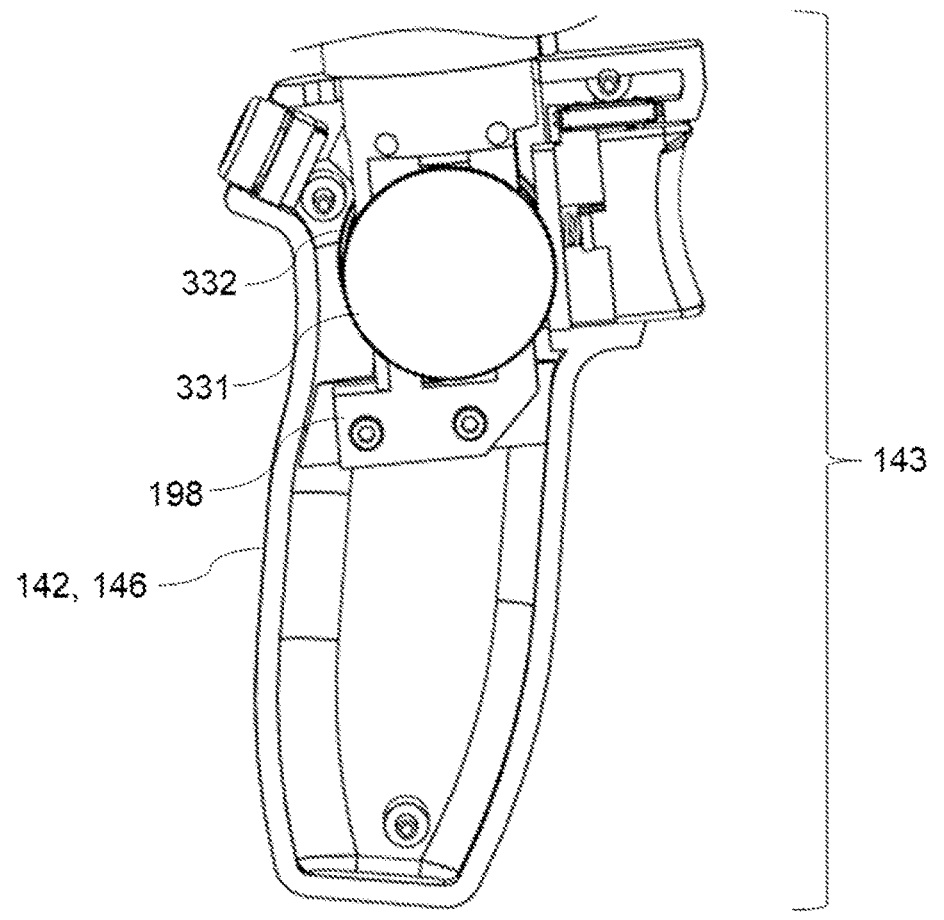
FIG. 17 illustrate a second embodiment of the detecting device housed in the housing's gripping part, FIG. 16 representing a partial view of such gripping part, without some part of the handle's housing so as to make visible said detecting device.

According to the invention, the handle 140 can comprise a detecting device 230 adapted to detect that the user is holding the handle 140 with his/her full hand. FIGS. 15 and 16 illustrate this detecting device 230 according to a first embodiment while FIG. 17 illustrates this detecting device 230 according to a second embodiment. FIGS. 15 to 17 are more particularly partial views of the handle's gripping part represented without the housing's right part.

According to the examples illustrated on FIGS. 15 to 17, this detecting device 230 is arranged on the handle 140, and can be housed, at least partially, in the handle's gripping part 143. This detecting device 230 is not only adapted to detect that the user holds the handle with his/her full hand, but also to generate a corresponding information and to send it to the control unit. As detailed below, the control unit is configured to compute and send instructions to the motorized joints of the robotic arm which holds the surgical tool of the system only when it has previously received the information that the user holds the handle with his/her full hand sent by such detecting device 230. The detecting device 230 thus aims to prevent a displacement unwillingly applied on the handle movable part from being transformed as an information and, consequently, as an instruction to be given to the motorized joints.

According to the first embodiment illustrated on FIGS. 15 and 16, the detecting device 230 comprises at least two pivoting levers 231, respectively arranged on the front part 149 and on the rear part 240 of the handle's housing. As illustrated, those pivoting levers 231 extends from a pivot 232 to a top part formed as a notch 233. As partially visible on the figures, the front part 149 and the rear part 240 of the handle's housing both present a cut 243 through which one of the pivoting levers 231 extends. As shown on FIGS. 15 and 16, the notches 233 of the pivoting levers 231 abut internal faces 244 of the housing's front part 149 and of the housing's rear part 240. The words "internal faces" here refer to faces of the concerned parts of the housing which face a volume defined by such housing's parts. The pivoting levers 231 are symmetrical and any reference indicated on one of them is directly transposable to the other one.

FIG. 15 illustrates a resting position of the detection device 230 wherein the pivoting levers 231 both abuts such internal faces 244 thanks to two elastic return devices 234. Each of these elastic return devices 234 are thus attached one of the pivoting levers 231 on one side and on a stop 235 on another side. The stop 235 and the housing's left part 146 can for instance form a single piece. At least, the stop 235 is firmly attached to the housing's left part 146, for instance thanks to any known fixation means or it can also be glued to said housing's left part 146.

The detection device 230 also comprises at least two activation devices 236, each of which being coupled to one of the pivoting levers 231. According to the illustrated embodiment, those activation devices 236 are formed as microswitches 237. As shown, each microswitch 237 comprises a swiveling bar 238 arranged to be in contact with one of the pivoting levers 231. Especially, each microswitch 237 presents a general rectangular shape. As illustrated, at least three terminals 239 are arranged on one of the faces of said rectangular shape—only one being referenced for each microswitch—and at least one button 330 is arranged on an opposed face of such rectangular shape. Obviously, this is only an example and other kind of activation devices could be used within the scope of the present invention.

When a pressure is applied on one of the pivoting levers 231, the corresponding swiveling bar 238 is displaced until it activates the button 330. When a sufficient pressure is applied on both buttons 330, an information is sent to the control unit 300, indicating that the user holds the handle 140 with his/her full hand. The words "sufficient pressure" here refers to a pressure greater than a predefined threshold. Such a position is for instance illustrated on FIG. 16. As shown on this FIG. 16, both swiveling bars 238 are in touch with the two buttons 330 and the elastic return devices 234 are compressed. Also, the pivoting levers 231 no longer abuts the internal faces 244 of the housing.

According to the second embodiment illustrated on FIG. 17, the detecting device 230 comprises at least one capacitive sensor 331, 332 housed in the handle gripping part 143. According to the illustrated embodiment, the detecting device 230 comprises two capacitive sensors 331, 332. As previously mentioned, this FIG. 17 illustrates the handle 140 represented without the housing's right part. As illustrated, a first capacitive sensor 331 faces the housing's right part—not shown—and a second capacitive sensor 332 faces the housing's left part 146. According to the illustrated embodiment, the first capacitive sensor 331 and the second capacitive sensor 332 are arranged at both sides of the casing 198 which receives the third displacement sensor. A recess can be arranged on the housing's right part and in the housing's left part 146, such recess being adapted to receive the capacitive sensors 331, 332. Those recesses are not illustrated here but it is understood that they present a shape complementary to the capacitive sensors' shape. According to the illustrated embodiment, the capacitive sensors are both shaped as circles and so are the corresponding recesses.

According to this second example, the detecting device 230 is thus adapted to send the information according to which the user hands the handle 140 with his/her full hand, only when the unique capacitive sensor, or both of these capacitive sensors 331, 332, depending on the embodiment realized, detect the presence of the user's hand. For instance, the capacitive sensors 331, 332 used can be adapted to detect the presence of the user's hand through a polycarbonate layer which can present a thickness of up to 4 mm.

Obviously, this detecting device 230 could take any other shape and it could be arranged on any other part of the system within the scope of the invention. For instance, the detecting device could be a mechanical switch, an optical switch, an infrared switch or any other known kind of switch. According to another example, this detecting device could be realized as a pedal on which the user has to apply a predetermined pressure with his/her foot in order for the control unit 300 to consider the user's input (i.e., the determined movement of the handle movable part and the information sent by the activation mechanism) into the computing of the instructions to be given to the motorized joints.

Figure 18:
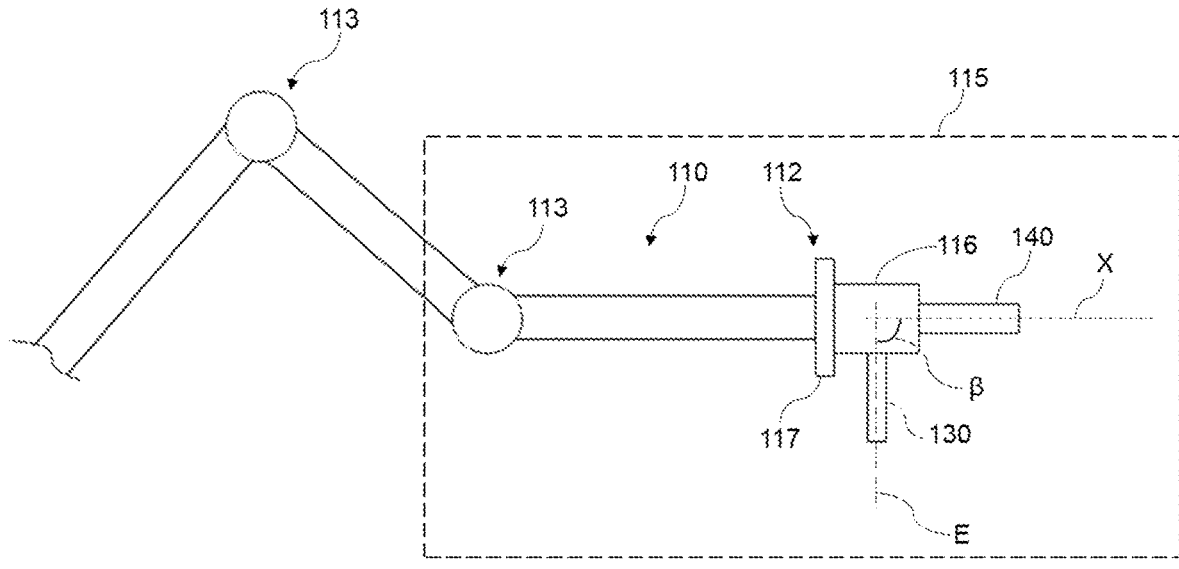
FIG. 18 illustrates, schematically, an end-effector of the computer-assisted surgery system illustrated on FIG. 1, the end-effector comprising at least one handle illustrated according to a first configuration of the invention.
Figure 19:
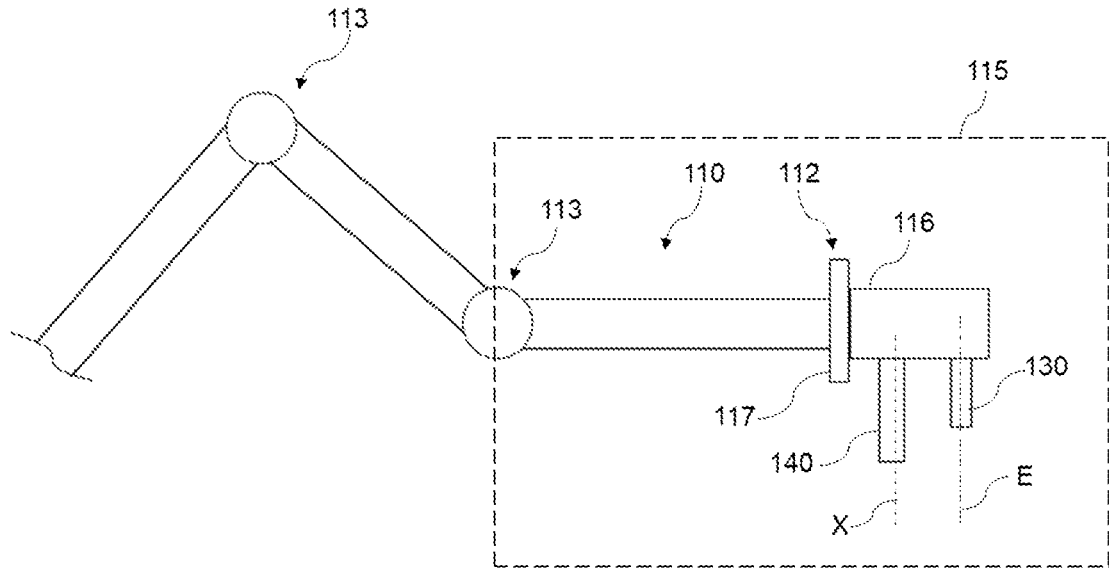
FIGS. 19 to 21 illustrate, schematically, the end-effector of the computer-assisted surgery system illustrated on FIG. 1, the end-effector comprising at least one handle illustrated according to a first variant, a second variant and a third variant of a second configuration the invention.

FIGS. 18 and 19 illustrate two different configurations of the present invention which differ from one another by the position of the handle 140 with respect to the position of the surgical tool 130, FIG. 18 illustrating a first configuration wherein the handle 140 is arranged according to a first position and FIG. 19 illustrating a second configuration wherein the handle 140 is arranged according to a second position. Also, according to the configurations illustrated on FIGS. 18 and 19, the surgical tool 130 and the handle 140 are fixed to a support 116 itself attached to the flange 117 formed by the second end 112 of the robotic arm 110. Again, this is only an example of the invention and the end-effector 115 could be realized without such support 116 without departing from the scope of the invention. On FIGS. 18 and 19, only the two last motorized joints 113 of the robotic arm 110 and the end-effector 115 are illustrated.

According to the first configuration illustrated on FIG. 18, the handle 140 presents a pistol grip shape, the main axis of extension X of the handle 140 and a main axis of extension E of the surgical tool 130 forming an angle β greater or equal to 30°. According to the illustrated embodiment, this angle β is a perpendicular angle. As a result, the main axis of extension E of the surgical tool 130 is secant with the main axis of extension X of the handle 140. Especially, according to the illustrated example, an assembly of the surgical tool 130 with the handle 140 presents an L-shape. This first configuration is close to the configuration of surgical tool traditionally used in surgeries, and especially in orthopedic surgeries. As such, this first configuration allows the user to be quickly comfortable using the system of the invention instead of such traditional surgical tool. This feature thus helps the user in having the sensation that he/she holds a traditional surgical tool intuitively, such that the user has the feeling, or the illusion, that he or she manipulates a traditional surgical tool directly. Moreover, this first configuration is also adapted to permit the user to perform a wide range of different movements without needing to move the entire robotic arm 110. If the surgical tool is attached to the robotic arm thanks to a shaft, as mentioned above, the main axis of extension of the surgical tool is aligned with a main axis of extension of such shaft.

According to the second configuration illustrated on FIG. 19, the main axis of extension X of the handle 140 is parallel to the main axis of extension E of the surgical tool 130. FIG. 19 illustrates a first variant of this second configuration wherein the handle 140 is arranged near the surgical tool 140 but at a non-null distance of it. As shown, the handle 140 and the surgical tool 130 both extends from the same side of the support 116. Two other variants of this second configuration are described hereunder with reference to FIGS. 20 and 21.

Figure 20:
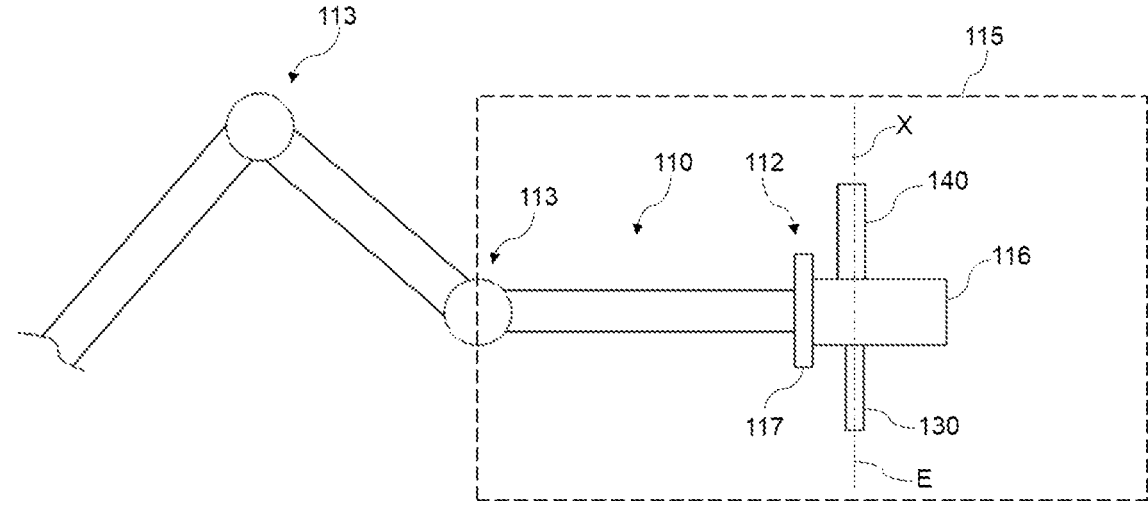
Figure 21:
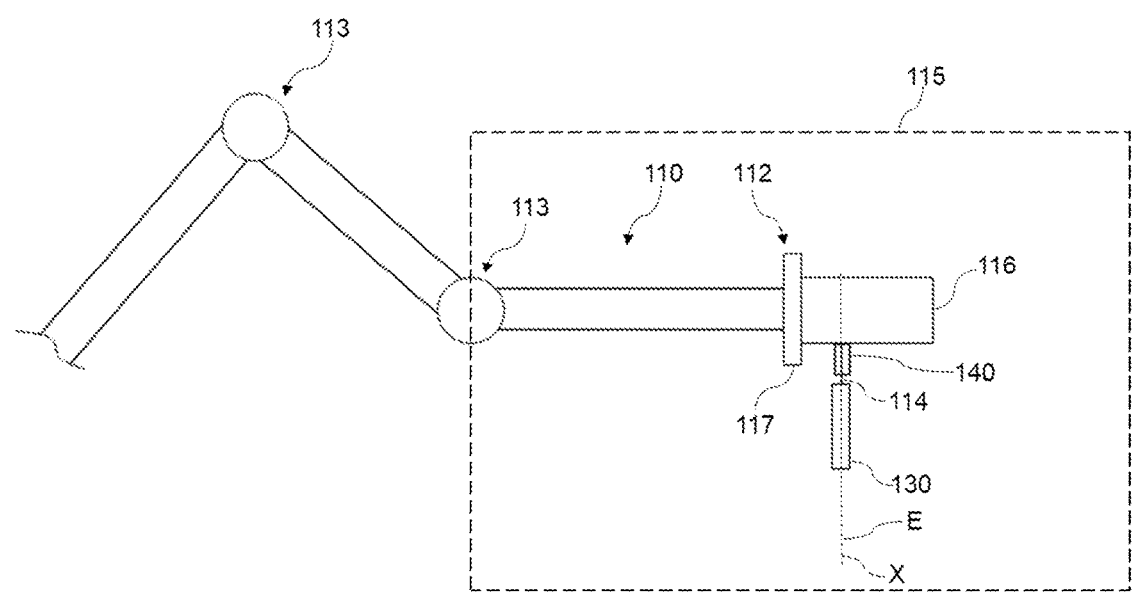

FIGS. 20 and 21 are representations of the computer-assisted surgery system 100 according, respectively, to a second variant of the second configuration illustrated on FIG. 19, and to a third variant of the second configuration illustrated on FIG. 19.

According to the second variant illustrated on FIG. 20, the handle 140 is aligned with the surgical tool 130. The main axis of extension E of the surgical tool 130 therefore extends the main axis of extension X of the handle 140. According to this second variant, the handle 140 is mounted at the rear of the surgical tool 130, the handle 140 and the surgical tool 130 being fixed on two opposite sides of the support 116.

According to the third variant illustrated on FIG. 21, the main axis of extension X of the handle 140 coincide with the main axis of extension E of the surgical tool 130. This third variant mainly differs from the second variant illustrated on FIG. 19 in the related position of the surgical tool 130 and the handle 140. As shown, the handle 140 and the surgical tool 130 are arranged on a same side of the support 116, the surgical tool 130 being attached to such support thanks to its shaft 114. Especially, the handle 140 here surrounds the surgical tool's shaft 114, thus providing an enlarged surgical tool's shaft 114. The handle 140 is, according to this variant of the second configuration, mounted as a grip zone which includes the surgical tool's shaft 114. This third variant gives the user a very precise sensation when he/she performs the planned treatment as he/she directly grabs the surgical tool's shaft through the handle 140.

Referring back to FIG. 1, the computer-assisted surgery system 100 comprises at least one localization unit 250 which comprises at least one first tracker 150 coupled to the surgical tool 130, at least one second tracker 151 coupled to the anatomical structure 200, and at least one locating device 163. The verb "coupled" here means that the concerned tracker 150, 151 is associated with the corresponding object, either by being directly attached to it or by being attached to another object, fixed with respect to the object of interest. Consequently, the first tracker can be attached directly on part of the surgical tool, for instance on the power tool of such surgical tool, on the base of the computer-assisted surgery system which encompasses the robotic arm carrying the surgical tool or on any other part of such computer-assisted surgery system. The second tracker 151 can be attached directly to the anatomical structure or it can be attached to a support rigidly connected to said anatomical structure.

As illustrated, the first tracker 150 is preferably fixed to the robotic arm 110, in close vicinity of the surgical tool 130, and the second tracker 151 is more particularly attached to the anatomical structure 200. The first tracker 150 could be fixed to the end-effector of the robotic arm. According to the illustrated embodiment, the second tracker 151 and the first tracker 150 are made of optical markers and are thus detectable thanks to the locating device 163 which comprises at least one camera 160, 161 and a control device 162. As detailed below, the at least one camera 160, 161 is adapted to acquire images and the control device 162 is adapted to treat this acquired images in order to determine relative position and orientation of the objects on which said first tracker 150 and said second tracker 151 are attached. According to the illustrated embodiment, the locating device 163 comprises two cameras 160, 161. The camera(s) 160, 161, and more particularly the control device 162 associated with such camera(s) 160, 161 is configured to send the determined relative position and orientation of the surgical tool 130 with respect to the anatomical structure 200 to the control unit 300. The communication between the control device 162 and the control unit 300 can be realized thanks to a wire, or an optical fiber, or it can be wireless, as illustrated on FIG. 1. According to another embodiment, not illustrated here, the control unit 300 and the control device 162 can be formed as a unique control apparatus.

In order to determine the positions and orientations of the first tracker 150 and of the second tracker 151, a distance between the two cameras 160, 161 should preferably be known. To make the calculation easier and to improve the accuracy of the determination of the positions and orientations of the first tracker 150 and of the second tracker 151, the cameras 160, 161 can be arranged on a same prop 164. According to the illustrated embodiment, the control device 162 is also supported by such prop 164. Alternately, the cameras could each have their own support, such supports thus having to be arranged at a predefined or determinable position.

The control unit 300 is configured to calculate and/or send instructions to at least one motorized joint 113 to move the robotic arm 110. For instance, the control unit 300 is configured to send instructions to the motorized joint 113 to the robotic arm 110 to permits matching the position and orientation of the robotic arm 110, and especially of the surgical tool 130 attached to said robotic arm 110, with the position and orientation of the anatomical structure 200. More particularly, as described below, the instructions sent by the control unit 300 to the motorized joint 113 aim to maintain the surgical tool 130 within a region of interest and outside of a region to avoid. Such region of interest is fixed in position with respect to the anatomical structure 200. The control unit 300 can, for instance, comprise one or more microprocessor, one or more random access memory (RAM) and/or one or more read-only memory (ROM), one or more calculators, one or more computers and/or one or more computer programs. In addition, the control unit 300 may include other devices and circuitry for performing the functions described herein such as, for example, a hard drive, input/output circuitry, and the like. According to the illustrated embodiment, the first tracker 150 and the second tracker 151 can encompass passive or active markers. The first tracker 150 and the second tracker 151 both comprise active or both passive markers. Alternately, one of the first tracker 150 or the second tracker 151 could encompass an active marker while the other one could encompass a passive marker. For instance, those markers, whether they are active or passive ones, can be shaped as spheres, disks, flat surfaces or patterns such as QR codes. Any other shape compatible with the present invention can also be used. A passive marker is for instance any light-reflective surface while an active marker is a light-emitting object, such as a Light Emitting Diode (LED).

The illustrated embodiment shows a localization unit which comprises two trackers, but it is understood that it could comprise as much trackers as needed by the control unit to compute the mentioned instruction. For instance, if the planned treatment consists in a total knee replacement, it could be useful to have a first tracker coupled to the patient's tibia, a second tracker coupled to the patient's femur and a third tracker coupled to the surgical tool, so that the control unit knows, at any time, the relative positions and orientations of those three objects with respect to each other.

The localization unit described is an optical localizer, but it could be different within the scope of the invention. For instance, the localization unit could be an electro-magnetic localizer, a radar localizer, an ultrasound localizer or an accelerometer or any hybridization of the such. Of course, other known localization unit could be used within the scope of the invention. For minimally invasive procedures, the localization unit is preferably an electromagnetic system using small coils or magnetic sensors attached to the anatomical structure and small coils or magnetic sensors attached close to an extremity of a surgical tool, for instance, miniature coils or magnetic sensors can be inserted in endoscopic instruments for endoscopic spine surgery. In a preferred embodiment, an electromagnetic emitter can be fixed to the computer-assisted surgery system, an electromagnetic tracking sensor can be attached to the anatomical structure in a minimally invasive way and another electromagnetic tracking sensor can be inserted as close as possible to the extremity of surgical tool to measure and compensate its deflections. In the present document, the words "extremity of surgical tool" and "surgical tool tip" are used without any distinction.

In order to determine the relative positions and orientations of the surgical tool with respect to the anatomical structure, the locating device can for instance use a known geometric model of the robotic arm if the first tracker is attached to the base of the computer-assisted surgery system and not to the surgical tool itself. Using well established techniques ensures that the position and orientation of the surgical tool extremity is known with respect to the anatomical structure to be operated, in real-time, typically at a frame rate of one hundred hertz or more, and with very low latency (less than ten milliseconds).

The control unit is adapted to compute instructions to be sent to the motorized joints, based on, among others, the respective position and orientation of the surgical tool with respect to the anatomical structure. Especially, the control unit is adapted to compute instruction(s) which, when executed, permit to match the relative position and the orientation of the surgical tool with respect to the anatomical structure with a planned relative position and orientation of the surgical tool with respect to the anatomical structure. Such planned relative position and orientation of the surgical tool with respect to the anatomical structure forms part of the surgical plan and can for instance be recorded before the beginning of the treatment.

Optionally, the relative position and orientation of the surgical tool with respect to the anatomical structure as well as part of the surgical plan can be displayed on the human-machine interface 102, thus giving the user a visual feedback of the displacements of the surgical tool and/or robotic arm, in real-time, regardless the relative position and orientation if the surgical tool within the anatomical structure. Displaying such information thus permits the user to verify, in real-time, that the requested displacement that he/she transmitted through the displacement of the handle movable part corresponds to the displacement induced by the execution of the instruction(s) computed based on said requested displacement. Obviously, visual feedback can be direct, as long as the user has direct sight toward said region of interest. In other words, the human-machine interface here comes as a help to the user whose sight can be hindered, by the anatomical structure to be treated itself or by its surroundings.

As mentioned above, the base 120 of the computer-assisted surgery system 100, attached to a reference frame BR, is fixed for the duration of the treatment. As the robotic arm 110 is attached to such base 120, a reference frame FI of the flange of the robotic arm 110 can be calculated by determining a first transfer matrix [BR_to_FI]. This first transfer matrix [BR_to_FI] is typically known, in real time, by the robot control system through internal servoing and joint sensors. A second transfer matrix [FI_to_RT] permits to determine the reference frame FI of the flange with respect to a reference frame RT attached to the first tracker 150. The second transfer matrix [FI_to_RT] is typically fixed during the course of the operation, well know by design and/or calibration. By "determining the reference frame", we here mean that the system, and especially the control unit 300, is adapted to determine the position and orientation of the concerned reference frame. From the position and orientation of the concerned reference frame, the control unit 300 is adapted to determine the position and orientation to the object to which such reference frame is attached. As the surgical tool 130 is coupled to the first tracker 150 and as the anatomical structure 200 is coupled to the second tracker 151 attached to a reference frame Ref, the reference frame RT can be determined with respect to the anatomical structure thanks to a third transfer matrix [RT_to_Ref]. This third transfer matrix [RT_to_Ref] thus varies depending on the motions of the reference frame Ref attached to the anatomical structure. This third transfer matrix [RT_to_Ref] is typically measured during the course of the treatment by a localization system monitoring both trackers 150, 151. As the anatomical structure is coupled to the second tracker 151, a targeted reference frame Ta of the surgical tool can be determined with respect to the reference frame Ref, thanks to a fourth transfer matrix [Ref_to_Ta], such targeted reference frame Ta being defined by the surgical plan, before the beginning of the treatment. As known in the art these transfer matrix are easily reversible.

As known in the art, a complex transfer matrix can thus be used by the control unit 300 to compute the instructions to be sent to the motorized joint 113 so as to ensure that the actual position and orientation of the surgical tool 130 with respect to the anatomical structure 200 matches the planned position and orientation of the surgical tool with respect to the anatomical structure. Such complex transfer matrix can be expressed as follow: [BR_to_FI] x [FI_to_RT]×[RT_to_Ref]×[Ref_to_Ta]. The surgical tool comprises a tool center point attached to a reference frame To, the execution of the instruction computed based on said complex transfer matrix aiming to match the reference frames To with the reference frame Ta. As known in the art, this process permits to perform real-time servoing, such as visual servoing when optical means are used for localization. Other technologies of localization allow similar servoing.

The computer-assisted surgery system 100 can comprise other sensors—not illustrated on the figures. For instance, at least one accelerometer can be implemented in the handle so as to detect a shakiness of the user. As explained below, the control unit 300 is adapted to consider such shakiness of the user and to remove it from the computing of the instructions to be sent to the motorized joints. Optionally, this accelerometer can also be used to detect and filter the vibrations generated by the surgical tool. Alternately or cumulatively, the shakiness and vibrations can be detected through a spectral analysis of the measured displacements, the measured displacements presenting a frequency above a predefined threshold being ignored by the control unit when computing the instruction(s).

If so, the power tool surgical tool of the surgical tool can also be adapted to send an information to the control unit related to a value of the current its motor uses. If this value exceeds a predetermined threshold, it can indicate that the user is trying to perform a forbidden movement for instance, and the control unit can thus be adapted to warn said user that he/she might be committing a mistake.

According to the invention, at least one sterile drape can be positioned on the computer-assisted surgery system, so as to cover all of such computer-assisted surgery system. Obviously, if needed, several sterile drapes can be used to cover the respective parts of said computer-assisted surgery system.

Figure 22:
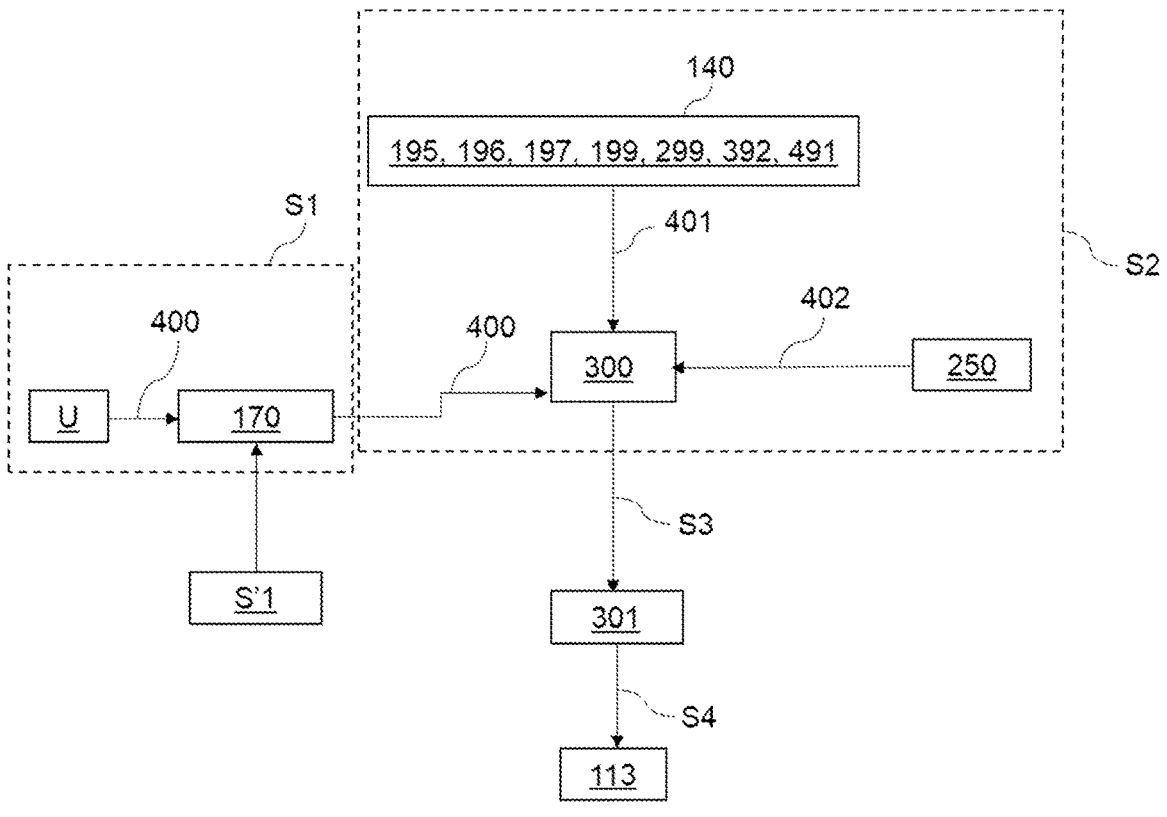
FIG. 22 is a schematical representation of a method for guiding the movements of a surgical tool held by a robotic arm of a computer-assisted surgery system illustrated on FIG. 1.

Referring to FIG. 22, we are now going to describe a method for guiding the movements of the robotic arm and/or of the surgical tool of the computer-assisted surgery system of the invention. As previously mentioned, the control unit 300 is adapted to compute instruction(s) to be sent to at least one of the motorized joints 113 based on at least one user input provided through the displacement of the handle movable part, and/or on a surgical plan, and/or on the relative position and orientation of the surgical tool with respect to the anatomical structure.

The system of the invention is operable in, at least:
a pre-operative mode allowing the control unit to control movements of the robotic arm based, only, on the surgical plan and on the relative position and orientation of the surgical tool with respect to the anatomical structure, while the surgical tool is deactivated,
an operative mode allowing the user to control movements of the surgical tool, based on the surgical plan, on the relative position and orientation of the surgical tool with respect to the anatomical structure and one a user input provided to the control unit in the form of measured displacements applied by the user to the movable part of the handle, while treating the region of interest with the surgical tool,
a collaborative mode allowing the user to control movement of the robotic arm by providing to the control unit inputs in the form of measured displacements applied to the movable part of the handle while the surgical tool is deactivated.

Regardless which mode is enabled, the method comprises a first step S1 wherein the user U records a surgical plan 400 in a storage medium 170 connected, thanks to a wire or wirelessly, to the control unit 300. Alternately, the storage medium 170 can be included in the control unit 300. Such surgical plan 400 comprises at least a region of interest of the anatomical structure wherein the treatment has to be performed. The surgical plan 400 can additionally comprise at least one constraint related to:
the kind of treatment to be performed on the anatomical structure, for instance whether it is a cutting, a screwing or a guiding as earlier mentioned,
the type of surgical tool used to perform said treatment, for instance whether it is a cutting tool, such as a saw, a drill, a reamer or a burr, a guiding tool, or a femoral head impactor,
a surgical tool access path within the anatomical structure.

Obviously, those cited constraints are only some key constraints to be considered by the control unit 300 to compute the instruction(s) to be sent to the motorized joint(s) 113, but this list of constraints is not exhaustive and other constraints could be considered without departing from the scope of the invention.

As schematically illustrated, the method of the invention comprises at least a second step S2 during which the control unit 300 is adapted to receive one or several of the following inputs:
a measured displacement 401 of the handle movable part sent by the displacement sensors 195, 196, 197, 199, 299, 392, 491,
the relative position and orientation 402 of the surgical tool with respect to the anatomical structure sent by the localization unit 250,
the surgical plan 400, recorded in the storage medium 170.

Then, during a third step S3, the control unit 300 is adapted to compute at least one instruction 301 to be sent to at least of the motorized joints 113, based on, depending on the selected mode, the surgical plan 400, the relative position and orientation 402 of the surgical tool with respect to the anatomical structure and/or the measured displacement 401 of the handle movable part. Finally, the control unit 300 is adapted, during a fourth step S4 to send the computed instruction(s) 301 to at least one of the motorized joints 113.

Especially, when the operative mode is enabled, the control unit 300 is adapted to compute instruction(s) 301 based on the measured displacement 401 of the movable part, on the surgical plan 400 and on the relative position and orientation 402 of the surgical tool with respect to the anatomical structure, to move the robotic arm to operate the surgical tool according to an optimal trajectory.

According to the invention, the optimal trajectory is defined as a trajectory permitting to perform the entire treatment of the region of interest as fast as possible and with as more accuracy as possible. As detailed below, the control unit is thus adapted to ensure, for instance, that the surgical tool does not treat the same part of the region of interest more than twice. The control unit is also adapted to ensure that the execution of the instruction actually permits the surgical tool to treat the region of interest, that is to say that the control unit is adapted to ensure that the computed instruction(s) are coherent with an attainability of the surgical tool. Moreover, the control unit is adapted to ensure that the movements of the robotic arm are consistent with the surgical plan, both when the surgical tool is within the region of interest, and also when the surgical tool is approaching such region of interest.

The control unit 300 is also adapted to compute, based on the measured displacement 401, on the surgical plan 400 and on the relative position and orientation 402 of the surgical tool with respect to the anatomical structure, a working range and to limit the working parameter of the surgical tool within such computed working range.

This computed working range is defined by one or several of the following parameters:

a maximal working speed of the surgical tool, a minimum working speed of the surgical tool, a maximum displacement speed of the surgical tool, a minimum displacement speed of the surgical tool.

According to the invention, the words "working speed of the surgical tool" refer to a speed at which the surgical tool performs the planned treatment. For instance, if the surgical tool is a drill, the working speed of the surgical tool corresponds to a speed of rotation of such drill.

The maximum displacement speed can be varied depending on the surroundings of the anatomical structure to be treated, thus aiming to prevent damages on said surroundings of the anatomical structure.

According to the invention, the working parameters can be defined before the beginning of the treatment and/or they can be modified during the course of the treatment. For instance, the minimum speed of the surgical tool can be high at the beginning of the treatment and decreased as the user performs such treatment. Conversely, some of these parameters cannot be modified.

According to the invention several of these working parameters can be coupled to one another, and such coupling or interaction can vary over the planned treatment. For instance, the maximum working speed of the surgical tool and the maximum displacement speed of such surgical tool may be coupled to a certain degree by the control unit, meaning that a modification of the maximum displacement speed of the surgical tool results in a modification of the maximum working speed of such surgical tool. The maximum working speed of the surgical tool and/or the maximum displacement speed of such surgical tool may be limited based on the nature of the anatomical structure and on a dissipated power of the surgical tool to progress, to avoid thermal damage which could for example result in necrosis of remanent structures, poor healing, inflammation of tissues, longer recovery timelines. The maximum working speed can also be coupled to the geometry of the surgical tool access path constraint within the anatomical structure and to the provided positions of environmental obstacles. The interaction between these working parameters and constraints can be defined before the beginning of the planned treatment and/or they can be varied during such planned treatment. The words "environmental obstacles" here refers to any obstacle present in the vicinity of the system of the invention and which must be avoided by the robotic arm and by the surgical tool.

As a result, even from identical input from the user, i.e. from an identical measured displacement of the handle movable part, the maximum displacement speed of the surgical tool can be computed as a function depending of several independent or coupled working parameters and be varied in different zones in vicinity or in the anatomical structure. For instance, the maximum displacement speed of the surgical tool can be limited, during a first phase of the planned treatment, to an initial landing and penetration speed when such surgical tool is displaced so as to reach the region of interest, such limitation being based on one or several of the following:

a displacement speed of the surgical tool requested by the user, through the displacement of the handle movable part, an intended direction of displacement of the surgical tool as requested by the user, through the displacement of the handle movable part, the relative position of the surgical tool within the region of interest, a targeted accuracy, the surgical tool nature and machining capacity in the intended direction, anatomical structure hardness or strength at the surface of such anatomical structure, an angle formed between a main axis of extension of the surgical tool and the surface of the anatomical structure, for instance to avoid skiving on the periosteum or on cortical bone, the surgical tool access path constraint, overall anatomical structure macroscopic stiffness laying on the surgical table, such stiffness defined as a response to surgical tool exerted force ratio to anatomical structure displacement.

Then, during a second phase of the planned treatment wherein the surgical tool is inside the region of interest, the maximum displacement speed of the surgical tool can be limited depending on general treatment setup and execution which can be based on one or several of the following:

the requested displacement speed of the surgical tool, through the user input, the intended direction of displacement of the surgical tool requested by the user, through the user input, the surgical tool nature and machining capacity in the intended direction, a distance measured between the surgical tool and a predetermined point of the region of interest of the anatomical structure;

Then, during a third phase of the planned treatment wherein the surgical tool is still in the region of interest, the maximum displacement speed of the surgical tool can be allowed to increase, so as for an equilibrium of forces of tool to anatomical structure to be established. The surgical tool may then, during a fourth phase of the planned treatment, face a softer bone such as trabecular structure, the control unit being adapted to re-calculate the maximum displacement speed of the surgical tool based on the mentioned coupled working parameters.

Finally, the maximum displacement speed can be limited down to zero as the surgical tool comes in close vicinity of a boundary of the region of interest which can be hidden from direct sight from the user, so as not to overshoot such boundary for safety reasons. More details are given about this boundary below. These parameters are only examples and different parameters than those described above can be implemented without departing from the invention. As such, even from an identical user input concerning the direction of displacement, the displacement speed of the surgical tool and the surgical tool working speed requested, the actual surgical tool displacement speed may be computed as a complex function of several independent or coupled parameters (as cited above), to result in the actual surgical tool displacement limited speed along its trajectory. Such parametric function would limit the maximum displacement speed, but the user would be free to request a lower speed from its input transmitted through the measured displacement of the handle movable part. Obviously, the complex function is also varied from varied user input, so as to provide an inter-active and safe robotic control.

Obviously, other parameter(s) can be implemented, and the control unit can be adapted to consider one or more of these parameters to define the working range.

Based on the measured displacement 401, the control unit 300 is adapted to determine an intended direction of displacement, that is to say a direction along which the user wishes to move the surgical tool. Such intended direction can comprise displacement(s) along one or several degrees of freedom of the handle movable part.

The control unit 300 is also adapted to determine a requested displacement speed of the surgical tool based on such measured displacement 401. For instance, the requested displacement speed can be related to the direction of the measured displacement and to a length of the measured displacement. For instance, if the user wants to accelerate the displacement speed, he/she needs to displace the handle movable part further away from its neutral position, and if the user wants to slow such displacement speed, he/she needs to displace the handle movable part to get it closer to said neutral position. Additionally, such requested speed can depend on the length of the measured displacement, such length being measured between the neutral position of the movable part and the current position of said movable part, the longer the displacement is, the faster, or the slower depending on the direction of the measured displacement, the user whishes the surgical tool to be displaced. When such requested speed is considered by the control unit 300, the at least one instruction 301 is computed to move the robotic arm to operate the surgical tool according to an optimal speed. The optimal speed here corresponds to a speed at which the planned treatment can be efficiently performed, whilst protecting the surroundings of the treated anatomical structure.

Obviously, the intended direction of displacement and the requested displacement speed are considered by the control unit in the computing of the at least one instruction. The words "displacement speed of the surgical tool" here refer to a speed at which the surgical tool progresses.

Optionally, the intended direction of displacement can be interpreted differently, depending on the setting of the system. Especially, the interpretation of the measured displacement and, consequently, of the intended direction of displacement, can be realized according to specific control laws, which can be customized for each degree of freedom.

The intended direction of displacement can be determined thanks to two steps which can be realized successively or independently by the control unit 300, a first step resulting in determining along which degree(s) of freedom the measured displacement has been applied and a second step resulting in determining in which proportion the measured displacement has been applied. For instance, if the handle movable part is displaced along the translational degree of freedom parallel to the plunging direction mentioned above, the intended direction of displacement comprises at least two information: a first information indicating that the user wants to displace the surgical tool along the plunging direction and a second information indicating if the user wants to displace the surgical tool forward, for instance to go deeper into the anatomical structure, or if he/she wants to displace such surgical tool backward, for instance to pull said surgical tool away from said anatomical structure. In order to provide a safe and ergonomic system, that is to say a system the most intuitive possible for the user, a specific control law used to interpret time series of measured displacements of the handle can be defined to compute the instruction(s) when a radical change of the intended direction is detected, for instance when the user is going forward and suddenly needs to go backward.

According to an aspect of the invention, the user might be forced to bring the handle movable part back to its neutral position for the change of direction to be considered. In such scenario, the user might feel an incoherence between the requested displacement and the displacement resulting of the execution of the computed instruction, as the surgical tool keeps moving forward as long as the handle movable part has not yet returned to its neutral position.

To reduce such feeling and improve the user-friendliness of the system, the control unit can be adapted to stop the displacements of the robotic arm when such a sudden change is detected, before actually instructing such robotic arm to go backward. For instance, the control unit can be adapted to stop the movement of the robotic arm, and consequently of the surgical tool, as soon as the measured displacement exceeds the previous measured displacement, beyond a predetermined threshold. The detection of a sudden reverse displacement applied on the movable part can for instance result in such stopping of the robotic arm. Such a control law gives the user the feedback that his/her requested change of direction has been detected and is considered by the control unit.

As mentioned above, the control unit is adapted to determine a requested displacement speed of the surgical tool based on the direction and the length of the measured displacement. The control law on which depends the determination of the requested displacement speed is not linear. For example, from an identical measured displacement, the requested displacement speed of the surgical tool can be detected as being slower when the handle movable part is close to its neutral position than when it's away from it. Moreover, the control unit can be adapted to exponentially increase, or decrease depending on the direction of the displacement applied on the handle movable part, the displacement speed resulting from the execution of the instruction(s) as the handle movable part is displaced away from its neutral position. As such, a modification of the intended direction of displacement, for instance to go backward whereas the previously intended direction of displacement was to go forward, has a minor impact as the displacement speed is rapidly decreased as the handle movable part gets closer to its neutral position and as the displacement speed is limited around the neutral position. As mentioned above, such neutral position corresponds to a position of the movable part wherein no displacement is detected by the displacement sensor(s) or a position wherein the displacement detected is below a defined value. Alternately, the control law applied to the requested speed while computing the instruction(s) to be sent to the motorized joint(s) could be a linear law, an exponential law, a customized law with predefined thresholds and so on, without departing from the scope of the invention. When the neutral position of the handle movable part is set as a position wherein some displacements are authorized but not detected by the control unit as long as they are below a defined value, such undetectable displacements form a dead zone, that is to say a zone wherein the user is able to displace the handle movable part, but wherein no displacement is measured by the displacement sensor(s).

As mentioned above, the control unit is adapted to compute instruction(s) to be sent to the motorized joint(s), based on, among others, the measured displacements of the handle movable part, from which the control unit is adapted to determine the intended direction of displacement and the requested displacement speed. If no other constraint is considered, the control unit is adapted to compute instruction(s) which, when executed, permit to move the robotic arm, and the surgical tool attached to such robotic arm, in the intended direction of displacement and according to the requested displacement speed. We are now going to describe the transform matrix used by the control unit to compute such instructions.

Figure 23A:
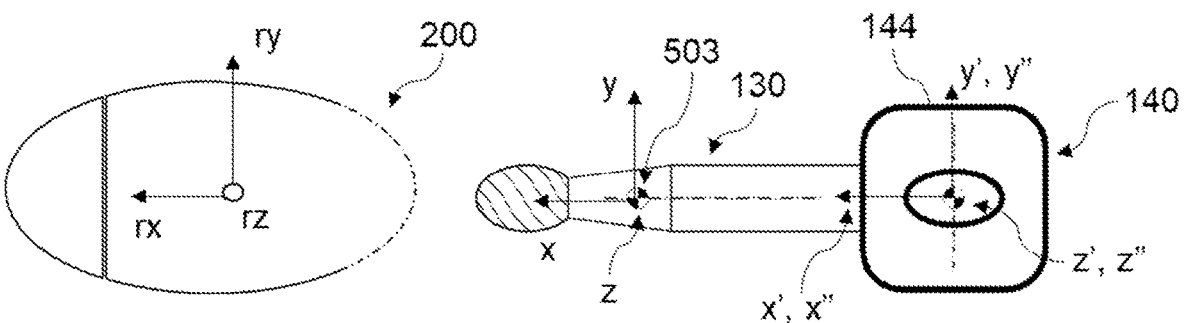
FIGS. 23a to 23g represent, schematically, a transformation of a displacement applied on the handle into a displacement of the surgical tool when such displacement is the sole input considered by a control unit of the computer-assisted surgery system to compute instruction to move such surgical tool.

As illustrated on FIG. 23a, the reference frame To is attached to the surgical tool 130 and presents an origin formed as a tool center point 503. A reference frame BJ is attached to the handle fixing part 144, the references frames To and BJ being related to each other thanks to a first transform matrix [BJ_to_To]. As the fixing part 144 is fixed in position with respect to the surgical tool 130, the reference frame To and the reference frame BJ are also fixed with respect to each other and the first transform matrix [BJ_to_To] is consistent and is determined or can be determined by the control unit. A reference frame Jo is associated with the handle movable part and the displacements of such movable part are measured with respect to the reference frame BJ. A second transform matrix [Jo_to_BJ], thus permits to express the displacements of the handle movable part with respect to the fixing part of the handle. This second transform matrix [Jo_to_BJ] is thus determined by the displacement sensors of the handle.

To compute the instruction(s) to be sent to the motorized joint(s), the control unit must define the transform matrix [Ta_to_Ta+1], wherein Ta expresses the position and orientation of the tool center point 503 attached to the reference frame To, at a given time and wherein Ta+1 expresses the requested position and orientation of the surgical tool to attain through actuation of the robotic joints. To do so, the control unit applies the following complex transform matrix:

[Jo_to_BJ]×[BJ_to_To]×[To_to_Ta+1], wherein a third transform matrix [To_to_Ta+1] permits to express the reference frame To attached to the tool center point 503 with respect to the requested position and orientation Ta+1 of the tool center point 503. We can then distinguish three different functioning of the system, a first functioning wherein the third transform matrix [To_to_Ta+1] is equal to 1, that is to say that the control unit only consider the intended direction of displacement in the computing of the instructions, a second functioning wherein the third transform matrix [To_to_Ta+1] is an homothety, meaning that the control unit consider both the intended direction of displacement and the requested displacement speed for computing the instructions, and a third functioning wherein the third transform matrix [To_to_Ta+1] is itself a complex transform matrix, meaning that the control unit considers the intended direction of displacement, the requested displacement speed and other inputs and parameters such as the position of the region of interest for instance, for computing the instructions.

Additionally, as previously explained, the control unit can consider the relative position and orientation of the surgical tool with respect to the anatomical structure when computing the instruction. When the control unit consider all these inputs, the transform matrix [BR_to_Ta+1] permitting to compute the instruction(s) can be expressed as follows:

$$[BR\_to\_Ta+1]=[BR\_to\_FI]\times[FI\_to\_RT]\times[RT\_to\_Ref]\times[Ref\_to\_Ta]\times[Ta\_to\_Ta+1].$$

This transform matrix allows the system to follow the movements of reference frame Ref attached to the anatomical structure, while considering the movements of reference frame Jo attached to the handle movable part and other displacements requested by the system and/or by the user.

FIGS. 23a to 23g illustrate, schematically, the reference frames To, BJ, Jo and Ref respectively attached to the surgical tool 130, to the handle fixing part 144, to the handle movable part and to the anatomical structure 200 to be treated. According to the illustrated embodiment, the handle movable part here comprises three degrees of freedom upon which two translational degrees of freedom and one rotational degree of freedom. The reference frame To is defined by a first axis x, a second axis y and a third axis z, the reference frame BJ is defined by a first axis x', a second axis y' and a third axis z', the reference frame Jo is defined by a first axis x", a second axis y" and a third axis z" reference frame Ref is defined by a first axis rx, a second axis ry and a third axis rz. For the sake of clarity, these reference frames are referenced only on FIG. 23a, FIGS. 23b to 23g illustrating only the origins of such reference frames. According to the illustrated embodiment, the first transform matrix [BJ_to_To] is such that reference frame BJ and the reference frame To are aligned with each other. Especially, the first axis x of the reference frame To is parallel to a first axis x' of the reference frame BJ, a second axis y of the reference frame To is parallel to a second axis y' of the reference frame BJ and a third axis z of the reference frame To is parallel to a third axis z' of the reference frame BJ. According to the example illustrated, the first axis x of the reference frame To is aligned with the first axis x' of the reference frame BJ. Such configuration aims to make the system transparent for the user. According to the invention, the position of the handle and the type of surgical tool used can be modified between two successive phases of the planned treatment. Consequently, the first transform matrix [BJ_to_To] is consistent as long as the position of the handle is not modified and as long as the type of surgical tool is not modified either. Obviously, if such modification is done between two phases of the planned treatment, the first transform matrix [BJ_to_To] is re-calculated accordingly.

Figure 23B:
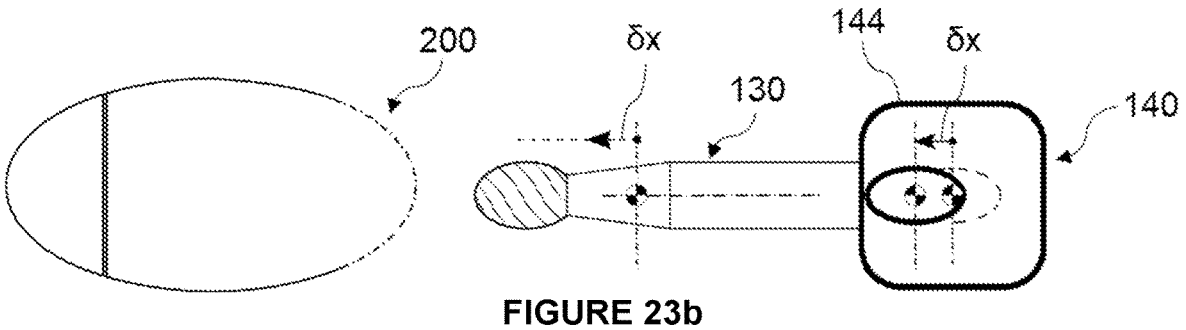

FIG. 23a especially illustrates a situation wherein the handle movable part is in its neutral position. In such neutral position, the reference frame BJ and the reference frame Jo are superimposed. FIG. 23b illustrates a situation wherein the user displaces the handle movable part. During such phase, the displacement sensors are adapted to measure such displacement δx of the handle movable part, with respect to the reference frame BJ. This displacement δx can also be expressed as the second transform matrix [Jo_to_BJ].

FIGS. 23a to 23g illustrate a situation wherein the anatomical structure does not move at all. In this situation, the control unit is thus adapted to compute instruction(s) to be sent to the motorized joint(s) so as for the measured displacement δx to be applied in the reference frame To associated with the surgical tool 130. In the situation illustrated on FIG. 23c, the displacement δx has been applied in the reference frame To and the user keeps applying the same displacement δx on the handle movable part. As schematically shown, the handle fixing part 144 is displaced simultaneously to the surgical tool 130 as such fixing part 144 and such surgical tool 130 are fixed in position with respect to each other. Consequently, the user must follow such displacements of the handle fixing part 144. As long as the displacement δx is applied on the handle movable part, the control unit is adapted to compute instructions, iteratively, so as to apply the measured displacement to the surgical tool 130, as illustrated by the arrow δ'x on FIG. 23c.

Figure 23C:
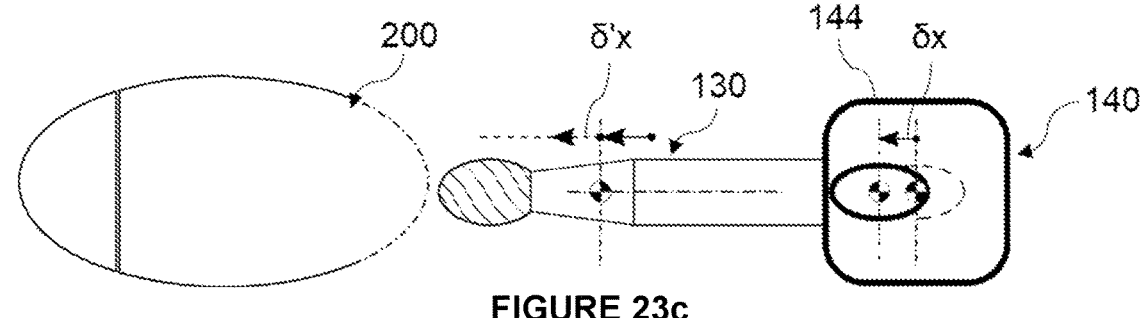
Figure 23D:
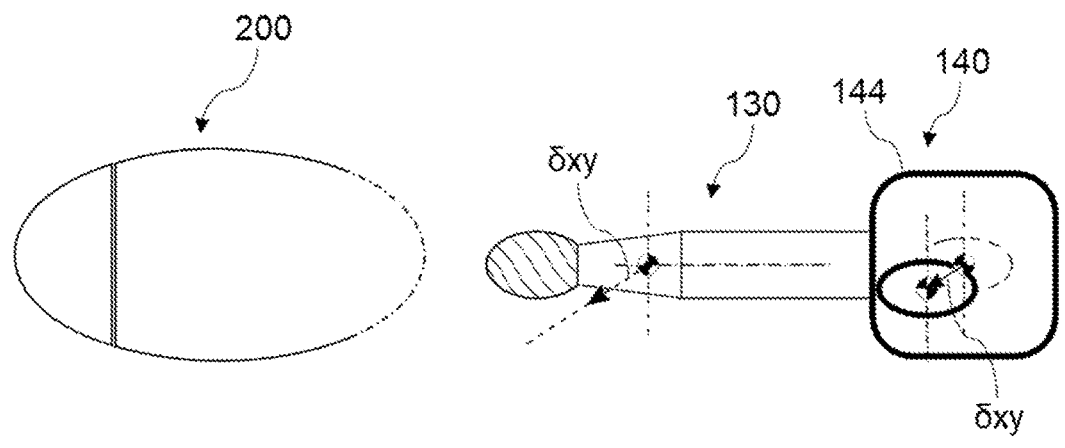
Figure 23E:
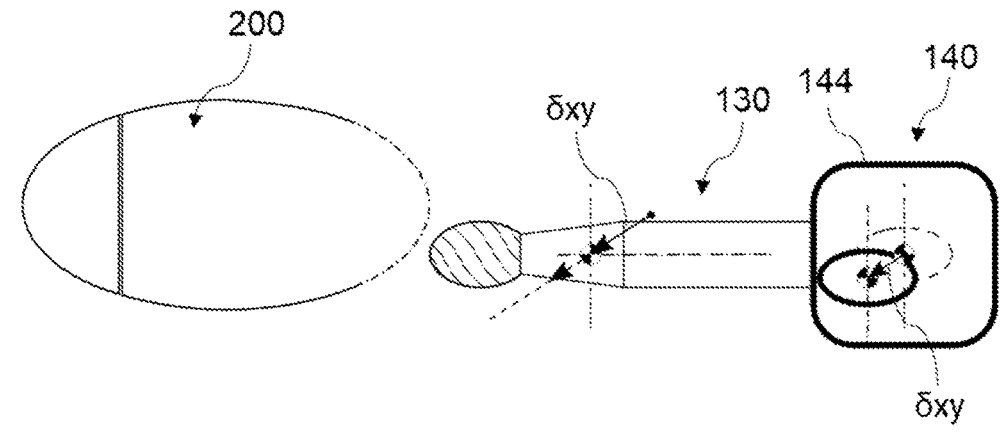

FIGS. 23d and 23e illustrate a situation which differs from the situation illustrated on FIGS. 23a to 23c in that the displacement Oxy applied on the handle movable part comprises at least one component along the first axis x' and at least one component along the second axis y' of the reference frame BJ. In a similar way to what has just been described, the control unit is adapted to, as long as the displacement Oxy is applied on the handle movable part, compute instructions to be sent to the motorized joint so as to apply the measured displacement Oxy to the reference frame To.

Figure 23F:
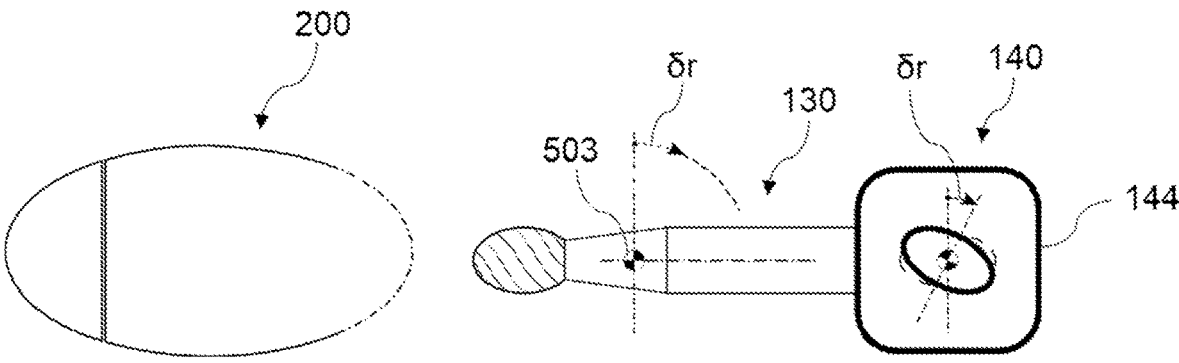
Figure 23G:
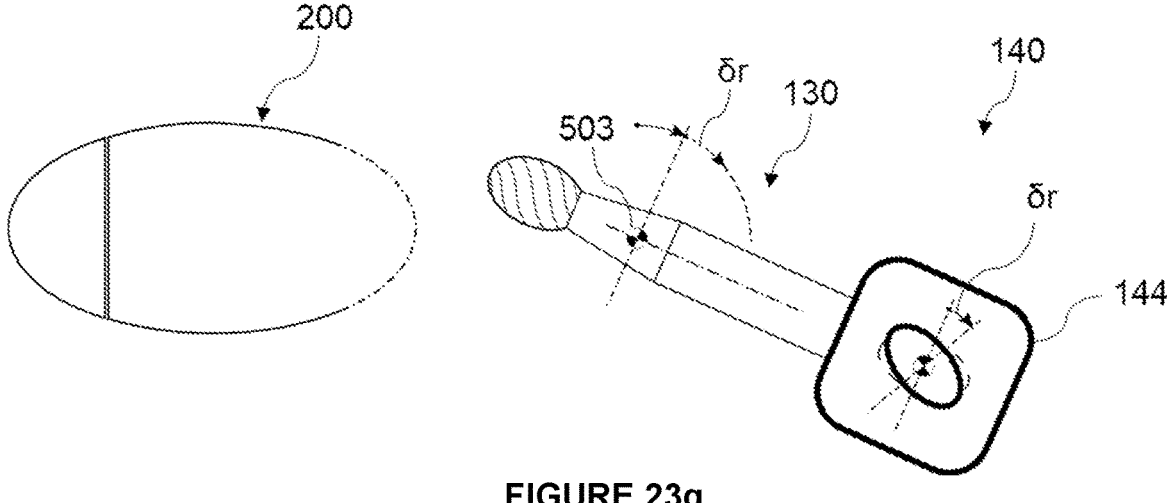

Finally, FIGS. 23f and 23g, illustrate another situation wherein the displacement Or applied on the handle movable part is a rotation. Especially, according to the illustrated embodiment, this rotation δr is applied around the third axis z' of the reference frame BJ. The control unit is thus adapted to compute at least one instruction which permits to obtain a rotation Or applied around the third axis z of the reference frame To associated with the surgical tool 130.

Additionally, the control unit is adapted to define, based at least on the region of interest, at least one static boundary 201 and at least one dynamic boundary 202, the control unit being adapted to compute instruction(s) so as to prevent the surgical tool from crossing said boundaries. Such boundaries 201, 202 can be set by the control unit 300, before the beginning of the treatment and such boundaries are schematically represented on FIGS. 24a to 24e and on FIGS. 25a to 25h. According to the invention, the region of interest is fixed with respect to the anatomical structure for the entire course of the planned treatment.

Figure 24A:
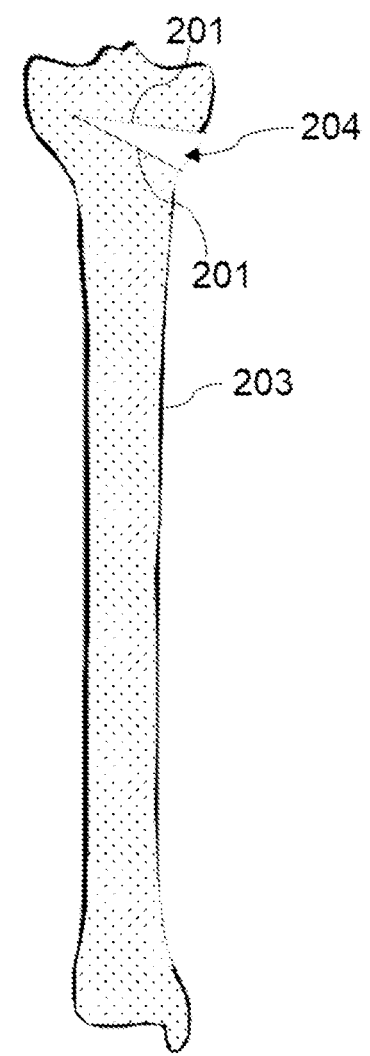
FIGS. 24a to 24e illustrate, schematically, several phases of a planned treatment which can be performed thanks to the computer-assisted surgery system of the invention, such planned treatment being realized thanks to a burr mounted on a drill.

FIGS. 24a to 24e and 25a to 25h illustrate an example of the design of a region of interest in a tibial osteotomy. A tibial osteotomy requires to perform a partial planar cut or a wedge on the tibial bone, leaving a hinge. Especially, FIG. 24a is a front view of the anatomical structure 200, here a tibial bone, after the completion of the planned treatment, while FIGS. 24b to 24e and 25a to 25h represent cross-sectional views of such anatomical structure 200, thus making visible the region of interest 204, here corresponding to the parts of the anatomical structure 200 to be removed, when the planned treatment is a tibial osteotomy. Such osteotomy can be used for many applications, such as high tibial osteotomies, femur and tibia bone cuts to position a knee prosthesis, femur cuts to initiate the placement of a hip prosthesis, osteotomies on a vertebra for correcting spine deformities, osteotomies on a mandible, complex osteotomies on the skull.

According to the example illustrated on FIGS. 24b to 24e, the surgical tool 130 is a surgical burr 131 mounted on a drill, the burr 131 forming the part of the surgical tool 130 which permit to cut the concerned parts of the tibial bone.

According to the example illustrated on FIGS. 24b to 24e, the at least one static boundary 201 here corresponds to a contour of the part of the anatomical structure 200, which has to be removed. This static boundary 201 is represented with solid lines on the figures. This static boundary 201 is fixed for the entire treatment, meaning that it cannot be modified by the user, nor by the control unit. By definition, this static boundary 201 forms a limit between the region of interest 204 and at least part of a region to avoid, the control unit thus being adapted to ensure, in the computing of the instructions to be sent to the motorized joint(s), that the surgical tool will not enter such region to avoid. As described below, the surgical tool can only be authorized to override said static boundary so as to be operated an enlarged region of interest under very specific conditions.

As illustrated on FIGS. 24b to 24e, the dynamic boundary 202a, 202b, 202c, 202d, which is represented with dotted lines, can be modified during the course of the treatment. The burr 131 illustrated has a cutting portion 131a and a non-cutting portion such as shank or shaft 131b. As shown, the burr extremity 131a forms the cutting portion of the surgical tool 130 in the example illustrated on FIGS. 24b to 24e and represents only a small part of the surgical tool 130. The illustrated burr 131 can cut either when displaced in the plunging direction, or when displaced sideways but limited in depth by the length of the cutting portion, such length being defined as the longest distance measured along the main axis of extension E of the surgical tool 130. The dynamic boundary 202a, 202b, 202c, 202d is, at each phase of the tibial osteotomy, computed, by the control unit, to ensure that only this burr extremity 131a, that is to say the cutting portion of the surgical tool 130, enters the region of interest 204 that is not yet milled out, so as to avoid that the non-cutting portion 131b of the burr 131 abuts a remaining portion of the region of interest 204, thus preventing to damage the surrounding of the region of interest 204, or the surgical tool 130. On FIGS. 24b, 24b' and 24d, the arrows illustrate the displacements of the surgical tool 130. Additionally, the region of interest 204 can be defined by at least one entry boundary 206, such entry boundary 206 forming the very first part of the anatomical structure to be cut by the surgical tool 130. In other words, the entry boundary 206 defines an access zone that the surgical tool must cross to reach the region of interest.

Figure 24B:
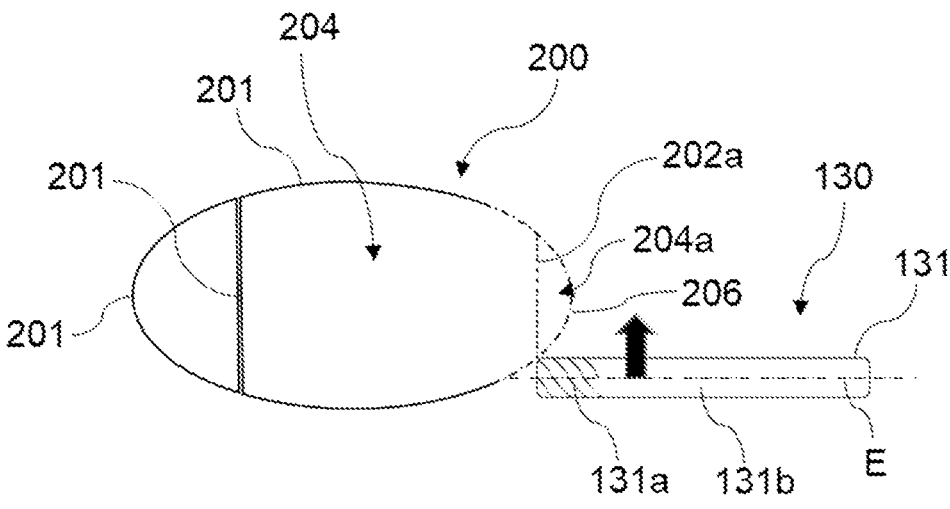
Figure 24B:
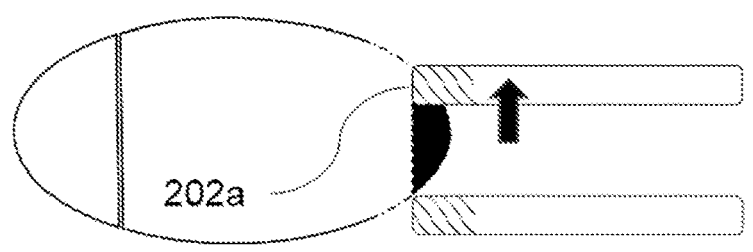

During a first phase of the tibial osteotomy illustrated on FIGS. 24b and 24b', a first dynamic boundary 202a is set to permit the cutting of a first part 204a of the tibial bone. Once the first part 204a of the bone is removed, as illustrated on FIG. 24b', the control unit is adapted to modify the first dynamic boundary 202a, to permit the user to keep removing bones.

Figure 24C:
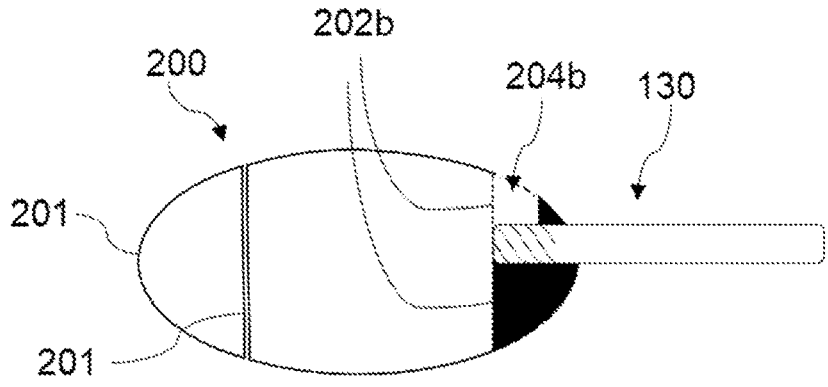
Figure 24D:
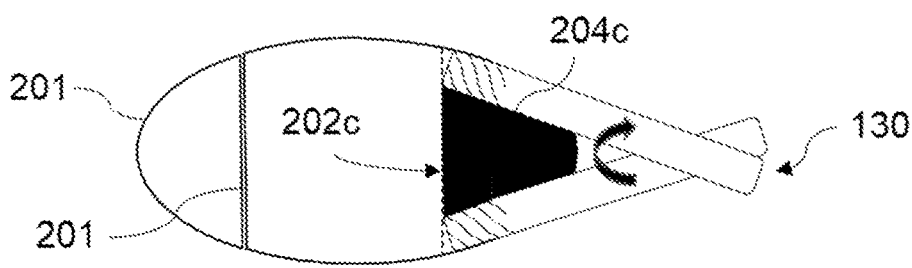
Figure 24E:
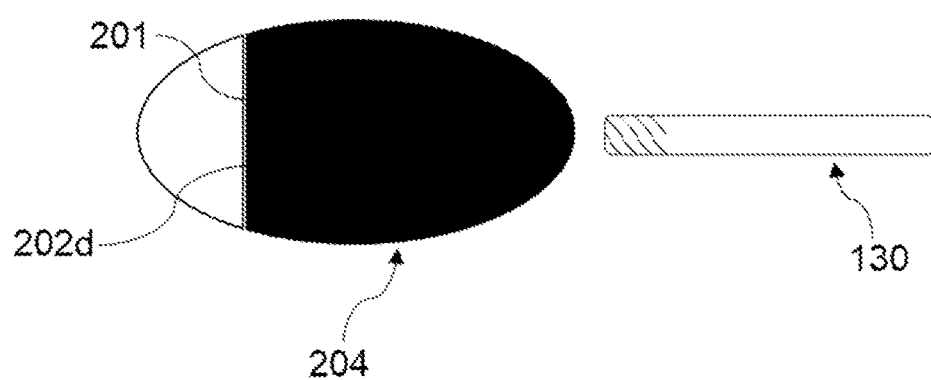

FIG. 24c illustrates a second phase of the tibial osteotomy, wherein a second dynamic boundary 202b is set to permit the cutting of a second part 204b of the tibial bone. Once the second part 204b of the tibial bone has been removed, the control unit is adapted to modify the second dynamic boundary 202b into a third dynamic boundary 202c as represented on FIG. 24d which illustrates a third phase of the tibial osteotomy. It is understood from this FIG. 24d, that the size of the removed parts 204a, 204b of the tibial bone here permit the user to apply an angulation in the displacement of the surgical tool 130, as represented by the arrow on FIG. 24d, thus permitting to remove a third part 204c of the tibial bone. Again, once the third part 204c of the tibial bone has been removed, the control unit is adapted to calculate subsequent dynamic boundaries up to last dynamic boundary 202d, for instance shown on FIG. 24e. Especially, FIG. 24e illustrated bone cut at the end of the retraction of the burr which is also a final phase of such tibial osteotomy cut. We note that during this final phase, the dynamic boundary has reached the static boundary 201, that is to say that the last dynamic boundary 202d matches said static boundary 201.

It is understood from these FIGS. 24a to 24e, that the user is thus more and more free in his/her movements as the planned treatment is performed. According to this particular example, the dynamic boundary 202 is modified step by step. The use of such dynamic boundaries thus permits to compute an optimize d trajectory.

Another example is illustrated on FIGS. 25*a* to 25*h*, wherein the at least one dynamic boundary 202 is used to forbid some displacements of the surgical tool 130. According to this other example, the at least one dynamic boundary 202 is thus set to be coherent with the attainability of the surgical tool, the dynamic boundary 202 being updated dynamically as the surgical tool progresses in the region of interest 204. The "attainability" of the surgical tool is defined as the parts of the concerned anatomical structure on which the surgical tool can perform the planned treatment, considering its current position and orientation relative to the position and orientation of the anatomical structure. FIGS. 25*a* to 25*h* illustrate an example of how the dynamic boundaries can be set so as for the displacement of the robotic arm resulting from the execution of the computed instruction(s), to be coherent with the attainability of the surgical tool.

FIGS. 25*a* to 25*h* also illustrate, in cross-section views, different phases of a tibial osteotomy. The example illustrated on FIGS. 25*a* to 25*h* differs from the example illustrated on FIGS. 24*a* to 24*e* in the kind of surgical tool 130 used, as FIGS. 25*a* to 25*h* illustrate a tibial osteotomy performed thanks to a reciprocal rotating oscillating saw 133. Such an oscillating saw 133 is adapted to perform a cut only along one authorized direction Da parallel to its main axis of extension E, since only an extremity 134 of such oscillating saw 133 is equipped with sharp tooth, such extremity 134 thus forming a cutting portion of said oscillating saw. Due to the oscillating movement of the illustrated saw blade around a rotating axis, the width of the cut is larger than the width of the saw blade tip itself. Consequently, the planar section swept by the oscillating saw blade is larger than the saw blade. According to this example, at least one dynamic boundary 202 can be calculated by the control unit, to prevent displacements of such saw blade along the other directions, and especially along lateral directions so as to avoid the lateral boundary of the sweeping of the saw blade to come abut with an uncut section of the region of interest 204. On FIGS. 25*a* to 25*h*, reference 201 still designates the static boundary while references 202*e*, 202*e'*, 202*f* designate the successive dynamic boundaries. As previously described, the static boundary 201 defines the part of the anatomical structure 200 to be removed and cannot be modified, while the dynamic boundary is permanently re-calculated by the control unit as the treatment is performed. In a similar way to what have been described with reference to FIGS. 24, at least one entry boundary 206 can also be defined at the surface of the anatomical structure 200.

Figure 25A:
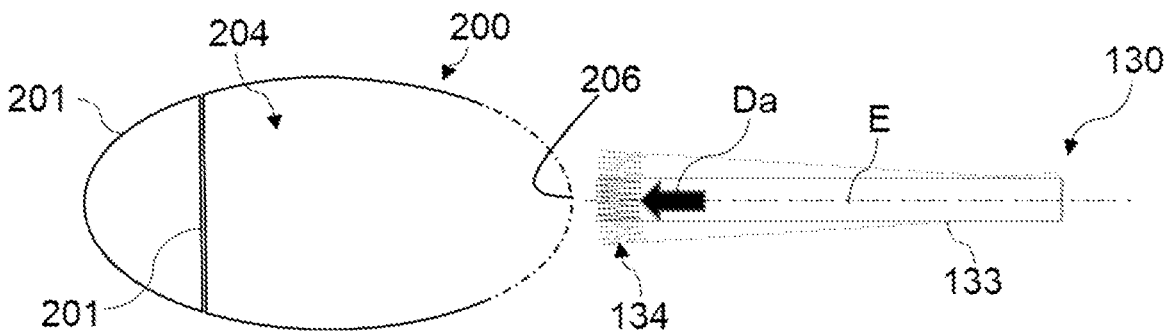
FIGS. 25a to 25h illustrate, schematically, several phases of the planned treatment illustrated on FIGS. 24a to 24e, such planned treatment being realized thanks to an oscillating saw on FIGS. 25a to 25h.
Figure 25B:
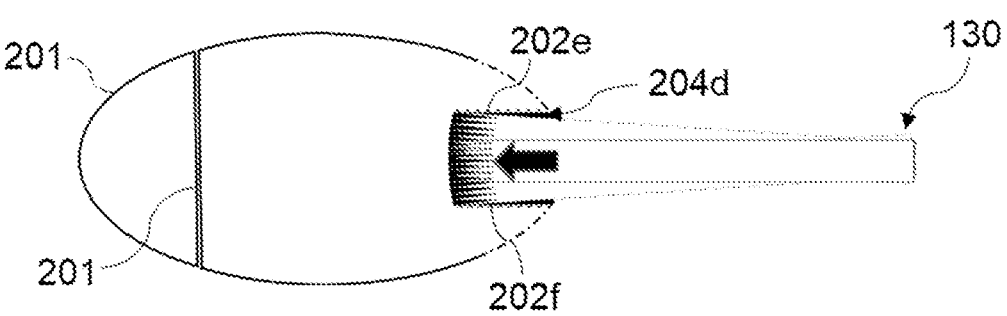
Figure 25C:
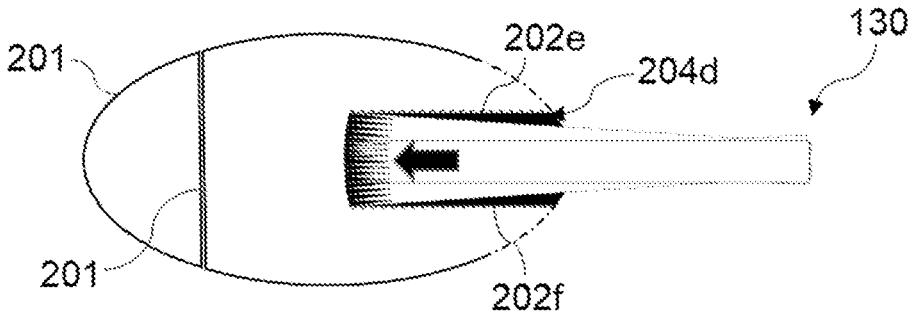
Figure 25D:
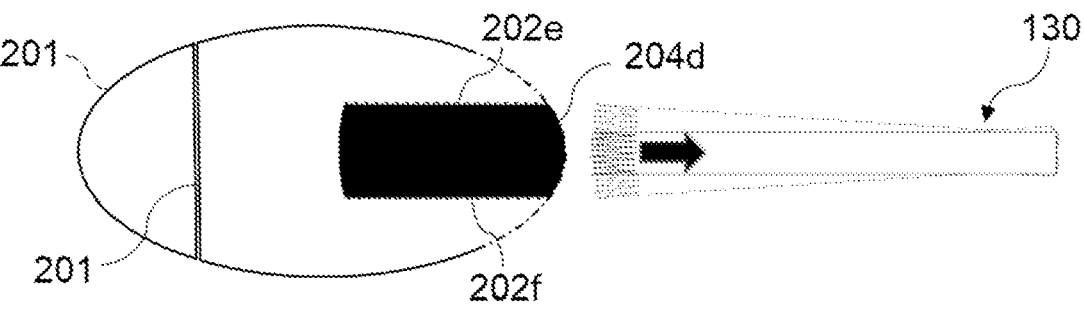
Figure 25E:
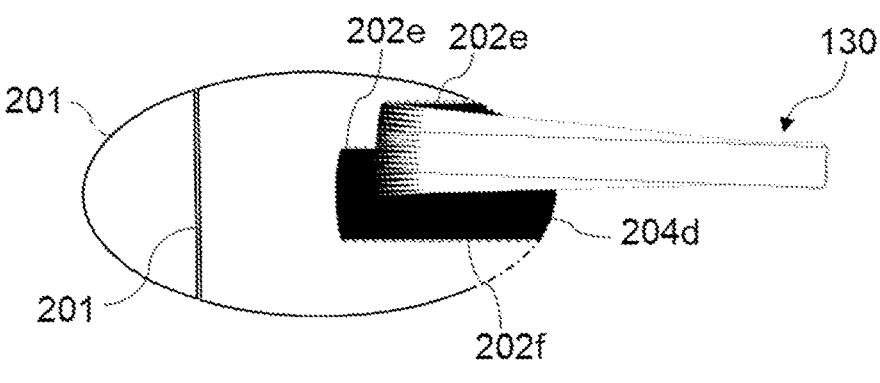
Figure 25F:
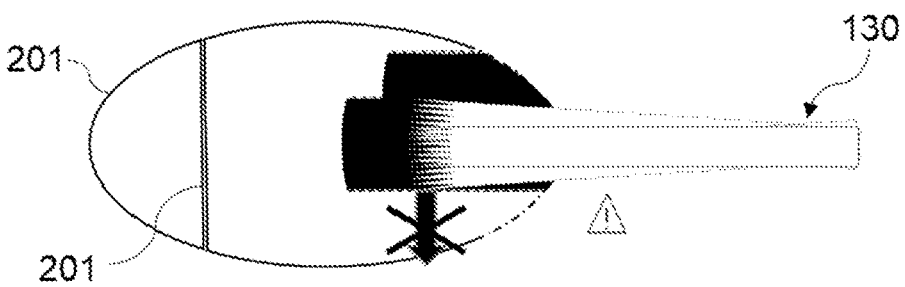
Figure 25G:
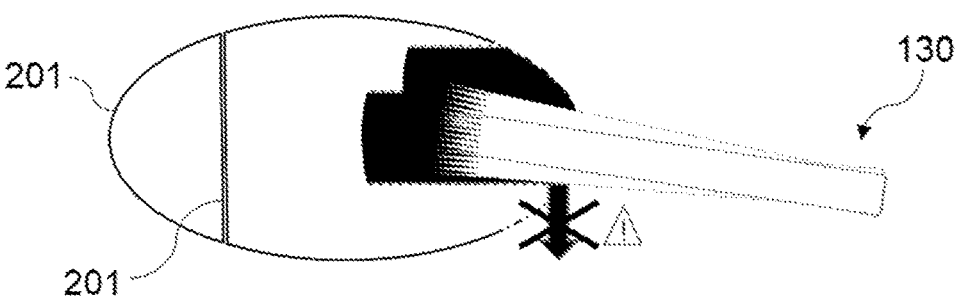
Figure 25H:
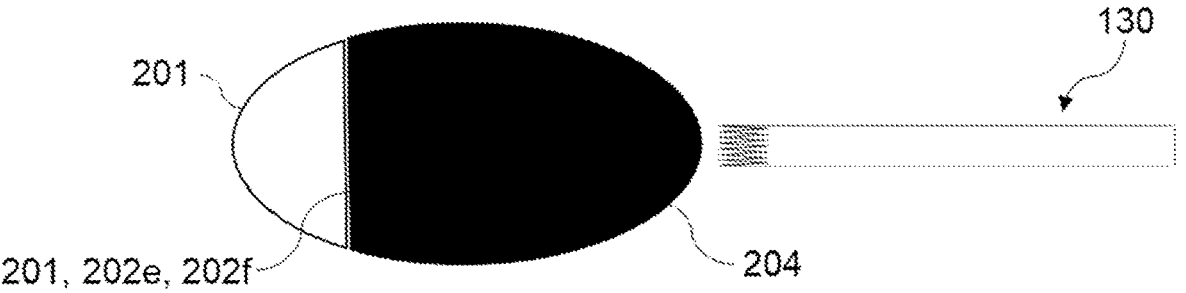

The user thus has to displace the oscillating saw 133 along the preferred authorized direction Da. During a first phase of the illustrated treatment, the removal of the parts of the anatomical structure thus forms a tunnel 204*d* within said anatomical structure. In order to constraint the user to displace the oscillating saw 133 only along the authorized direction Da, at least two dynamic boundaries 202*e*, 202*f* are set along the tunnel 204*d* formed, as shown on FIGS. 25*b* and 25*c*. In order to cut laterally, the user thus needs to retract the oscillating saw 133 from the anatomical structure—as shown on FIG. 25*d*—and to perform another cut, parallel, or sensibly parallel, to the tunnel 204*d* formed during the first phase, as shown on FIG. 25*e*. The other cut is realized so as to overlay the tunnel 204*d* formed during the first phase of the planned treatment and result in the removal of another part of the anatomical structure, thus enlarging the tunnel 204*d*. The control unit is thus adapted to re-calculate, in real-time, the new position and/or extensions of the dynamic boundaries 202*e*, 202*e'*, 202*f*. Such dynamic boundaries are thus set depending on the surgical plan and on the relative position and orientation of the surgical tool 130 with respect to the anatomical structure 200. The user thus gains more and more freedom in his/her displacements, while the angular or lateral displacements of the oscillating saw 133 are forbidden when such swept section of the oscillating saw 133 is close to the defined dynamic boundaries 202*e*, 202*f*, as illustrated by the crossed-out arrows represented on FIGS. 25*f* and 25*g* as non-cutting sections of the sweeping blade come into contact with said dynamic boundaries. FIG. 25*h* finally shows the last phase of the tibial osteotomy, wherein all the bone forming the region of interest 204 has been removed, and wherein the dynamic boundaries 202*e*, 202*f* have reached the static boundary 201.

The present invention thus imposes to the user who wants to perform an osteotomy with an oscillating saw blade as described above, to pump such saw blade forwards and backwards. When the user pushes forward the oscillating saw in an area of a bone defined by the dynamic boundaries. The control unit thus prevents the user from going laterally and does filter such lateral or angular displacements of the handle movable part when the oscillating saw is deep in the bone, thanks to the dynamic boundaries successively set. The user will understand that he/she needs to go backwards and then displace the oscillating saw by a lateral translation and/or a rotation before pushing forward again. Such dynamic boundaries can thus be adapted to ensure that the execution of the computed instruction(s) results in movement of the surgical tool which comply with the attainability of such surgical tool.

Obviously, if the oscillating saw used is adapted to perform cuts along the lateral directions, the dynamic boundaries preventing the corresponding lateral displacements are not set in the same fashion by the control unit. In other words, it is understood that the dynamic boundaries ensuring that the execution of the instruction(s) complies with the attainability of the surgical tool are computed differently, depending on the kind of surgical tool used. Orbital or circular motion saw with saw blades having cutting teeth along all sides is an example of such blade capable of frontal tip and lateral cuts. Linear reciprocating blade saw is another such example. It can be easily understood from those examples with a burr and saw blade, that the calculation of the dynamic boundaries related to the surgical tool thus depends on, at least, the kind of surgical tool used, cutting surfaces and directions, the kind of treatment to be performed and selectable parameters so as to compute them dynamically of step-by step or a combination thereof.

As the dynamic boundaries participate to prevent the user to perform forbidden movements, such dynamic boundaries thus participate to defined the optimal trajectory.

According to a non-illustrated example the control unit can be adapted to set and modify the dynamic boundaries so as to prevent the surgical tool to enter more than twice at a same location of the region of interest. According to this alternative, the control unit is thus adapted to position the dynamic boundaries around the already treated parts of the anatomical structure. These dynamic boundaries can thus permit, according to this alternative, to optimize the displacements of the surgical tool so as to perform the planned treatment as fast as possible, as it is providing a sensorial feedback to the user separated from navigation information visual feedback. Such dynamic boundaries thus permit the surgical tool to overlay some already treated parts of the anatomical structure, thus ensuring that the wanted treatment—for instance the wanted cutting—is completed, while ensuring that the surgical tool is not unnecessarily re-operated in an already treated part of the region of interest.

Obviously, several types of static and dynamic boundaries, as described above, can be combined during the course of a single phase of a planned treatment. For instance, the control unit can set a first dynamic boundary adapted to prevent forbidden movement of the surgical tool and the control unit can set a second dynamic boundary adapted to ensure that the surgical tool does not return more than twice in a part of the anatomical structure wherein the treatment has already been performed. Any other combination of such static and/or dynamic boundaries can be set by the control unit, within the scope of the invention.

Figure 26A:
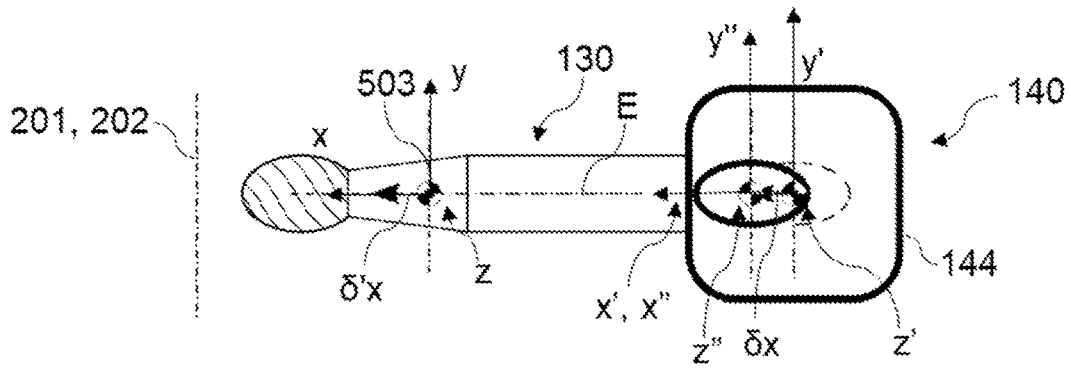
FIGS. 26a to 26f illustrate, schematically two different behaviors of the computer-assisted surgery system when the surgical tool reaches a defined boundary, FIGS. 26a to 26c illustrating a first behavior and FIGS. 26d to 26f illustrating a second behavior.
Figure 26B:
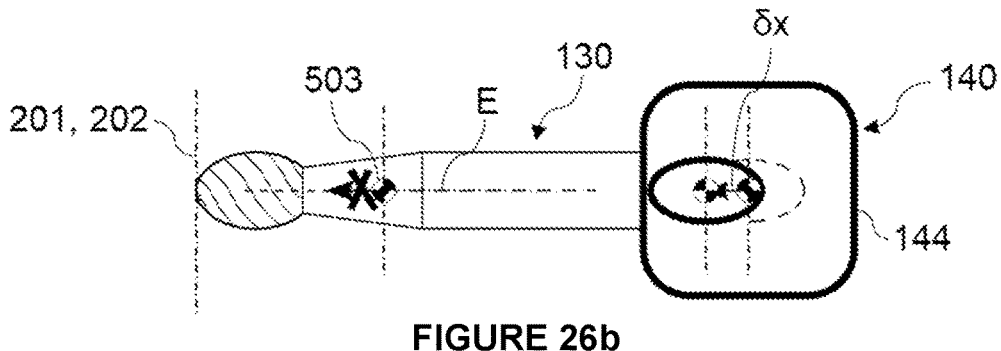
Figure 26C:
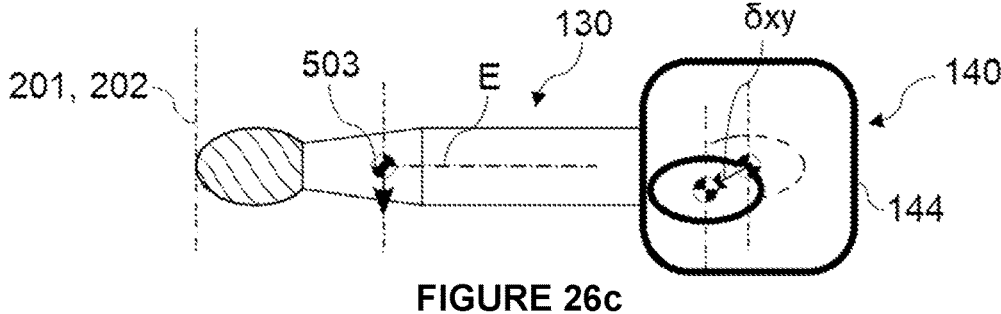
Figure 26D:
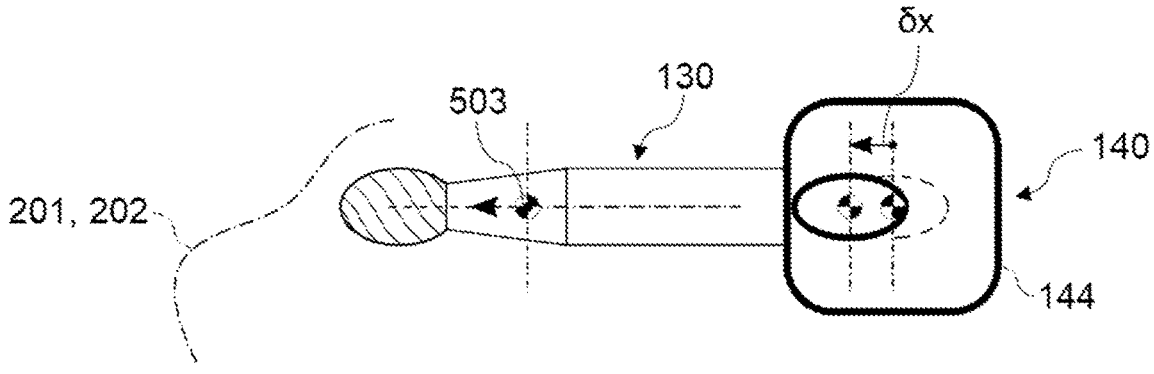
Figure 26E:
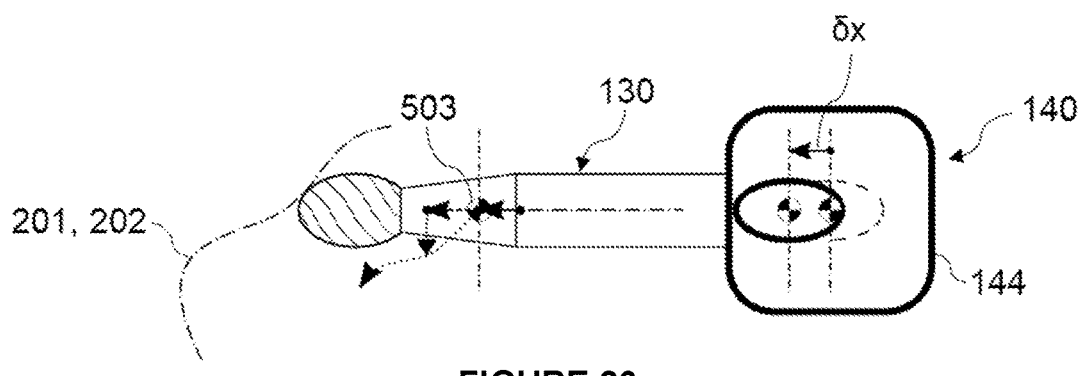
Figure 26F:
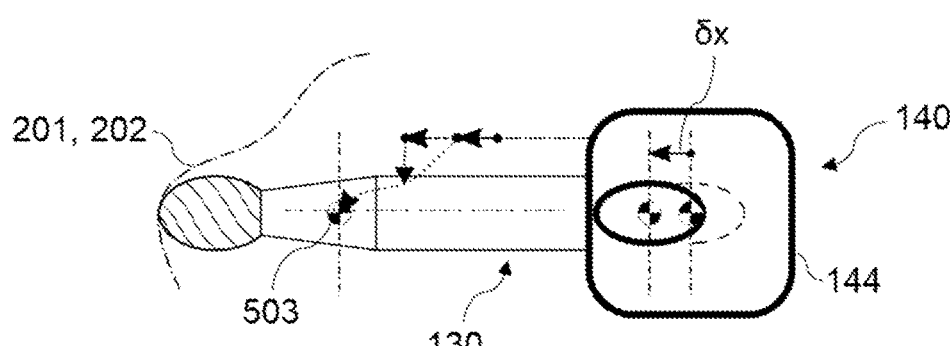

FIGS. 26a to 26f illustrate two different behaviors of the computer-assisted surgery system in altering the intended direction of displacement requested by the user, when the surgical tool reaches one of the static or the dynamic boundaries, FIGS. 26a to 26c illustrating a first behavior and FIGS. 26d to 26f illustrating a second behavior.

FIGS. 26a to 26c illustrate a situation where the boundary 201, 202, whether it is a static boundary or a dynamic one, reached by the surgical tool 130 is orthogonal to the intended direction of displacement requested through the displacement of the handle movable part. According to the first behavior of the robotic arm, the control unit is adapted to compute instruction(s) so as for the movement of the robotic arm to be stopped, in the direction orthogonal to the concerned boundary 201, 202, when the surgical tool 130 reaches said boundary 201, 202. FIG. 26a illustrates a situation wherein the user has displaced the handle movable part relative to the handle fixing part 144. As mentioned above, such displacement δx is determined thanks to the second transform matrix [Jo_to_BJ] so as to be computed into an instruction which, when executed, results in an application of the intended displacement δ'x, to the tool center point 503. As the execution of such instruction results in the fact that the surgical tool reaches the concerned boundary 201, 202, the control unit is adapted to stop the movement of the robotic arm along the concerned direction. As schematically illustrated on FIG. 26b, despite the displacement δx requested by the user along a direction parallel to the first axis x of the reference frame To attached to the surgical tool 130 the control unit is adapted to compute instruction so as to set the displacement speed of the surgical tool 130 to zero, along said first axis x of the reference frame To, in the forward direction. In other words, in such situation, the maximum displacement speed and the maximum working speed of the surgical tool which both participate to define the working range are set to zero. FIG. 26c illustrates a next step, wherein the displacement Oxy applied on the handle movable part comprises at least one component along the first axis x' and at least one component along the second axis y' of the reference frame BJ. As the displacement along the first axis x of the reference frame To with respect to the reference frame Ta is now forbidden, the control unit is adapted to only consider the displacement along the second axis y' of the reference frame BJ when computing the instruction(s). The execution of such instruction(s) thus results in a displacement of the tool center point 503 along the second axis y of the reference frame To, thus permitting the surgical tool 130 to be displaced along the concerned boundary 201, 202. For the sake of clarity of the figures, the axes of the cited reference frames are only illustrated on FIG. 26a but are directly transposable to the FIGS. 26b to 26f.

According to the second behavior illustrated on FIGS. 26d to 26f, when the surgical tool 130 reaches one of the static or dynamic boundary 201, 202, the optimal trajectory is defined so as for said surgical tool 130 to be displaced along the concerned static or dynamic boundary 201, 202. According to this second behavior, the control unit is adapted to compute at least one instruction which permits to, when executed, displace the surgical tool 130 along a modified trajectory with respect to the intended direction of displacement, to ensure that the surgical tool 130 does not cross the concerned boundary 201, 202. FIG. 26d thus illustrates a situation wherein the user requests a displacement Ox applied on the handle movable part along the first axis x' of the reference frame BJ attached to the fixing part 144. A corresponding instruction is thus computed, and the tool center point 503 is displaced by the execution of such instruction. FIGS. 26e and 26f illustrate situations wherein said instruction has been executed and wherein the surgical tool 130 has, consequently, reached one of the boundaries 201, 202, and wherein the user keeps requesting the same displacement. FIGS. 26e and 26f thus represent a situation wherein the intended direction of displacement is not modified by the user but wherein the surgical tool cannot be displaced along such intended direction of displacement anymore. According to the second behavior, the control unit is adapted, in such situation, to compute instruction(s) permitting to displace the surgical tool 130 along the concerned boundary 201, 202, even if the displacement applied on the handle movable part only contains a displacement along the first axis x' of the reference frame BJ. The computing of such instruction(s) is realized iteratively, as long as the user requests displacement Ox in the same achievable direction along the concerned boundary.

FIG. 26f especially illustrates a situation wherein the surgical tool 130 cannot continue its displacement along the boundary 201, 202 without being displaced in a direction opposite to the intended direction of displacement. In such a situation, the surgical tool 130 is thus stopped. The user must then retract such surgical tool by displacing the handle movable part along the first axis x' of the reference frame BJ, in an opposite direction to the one applied until then to be able to continue the planned treatment. The second behavior thus ensures that the intended direction transmitted by the user through the displacement of the handle movable part is respected, at least partially, in the computing of the instruction(s) as long as displacements along said intended direction are possible.

As previously mentioned, the surgical plan comprises a recorded surgical tool access path 205 within the anatomical structure. As detailed with reference to FIGS. 27a to 27d, the surgical tool access path 205 is defined by the entry boundary 206 and by at least one protective boundary 207. The protective boundary 207 is used to restrict the access path of the surgical tool 130 within the region of interest 204, thus protecting the surroundings of the anatomical structure 200 which can be made of soft tissues, nerves, vessels and so on, and which are to be left undamaged. Especially, the control unit is adapted to compute instruction(s) so as to ensure that the surgical tool does not cross such protective boundary. The surgical tool access path 205 constraint within the anatomical structure 200 is defined so as for the planned treatment to be optimized. For instance, this surgical tool access path constraint can be defined so as to provide access to the region of interest 204 while preventing any interference with other anatomical structures. For example, this access path constraint can form a tunnel through which the surgical tool 130 is inserted, and such access path constraint can encompass a pivot point 600 of the surgical tool 130, thus ensuring that such surgical tool 130 is able to reach any part of the region of interest 204 while preventing damaging soft tissues through which such surgical tool 130 has been inserted. Obviously, this is only an example and the access path constraint could be of any geometry within the scope of the invention.

For instance, FIGS. 27a to 27d illustrate, schematically, a situation wherein the planned treatment is minimally invasive surgery, thus where the access path to the anatomical structure is constrained. On these figures the multiple surgical tools 130 represented illustrate different positions and orientations of the same surgical tool 130. In minimally invasive surgical treatments, the surgical tool 130, here realized as a burr 131 similar to the one described with reference to FIGS. 24a to 24e, is, most of the time, inserted in the patient through a small surgical tool access path 205. Especially, the surgical tool access path 205 is sized to only permit the entry of the surgical tool 130. In this case, the contour of the surgical tool access path 205 can be defined as a protective boundary 207, thus preventing the surgical tool 130 to be in contact with said surgical tool access path 205 and thus preventing any damage to the surroundings of such surgical tool access path which includes, among others, soft tissues. As shown, this surgical tool access path 205 is also defined by the entry boundary 206, as described above with reference to FIGS. 24 and 25, which is set at the first surface of the anatomical structure 200 to be treated. Such entry boundary 206 thus forms a limit between the surgical tool access path 205 and the region of interest 204.

In such minimally invasive surgical treatment, it is advantageous to insert the surgical tool 130 through the surgical tool access path 205 and to be able to displace the surgical tool 130 within the region of interest 204 while preventing any damage on the tissues which surrounds said region of interest 204. In order to achieve this, a pivot point 600 or a pivot area can be set by the control unit 300, the control unit 300 being adapted to compute instructions so as for the main axis of extension E of the surgical tool 130 to always cross such pivot point 600. Such pivot point 600 or pivot area is thus fixed with respect to the anatomical structure 200. The pivot point 600 can be shaped as an ad-hoc point, as a line or as a plane within the scope of the invention.

Figure 27A:
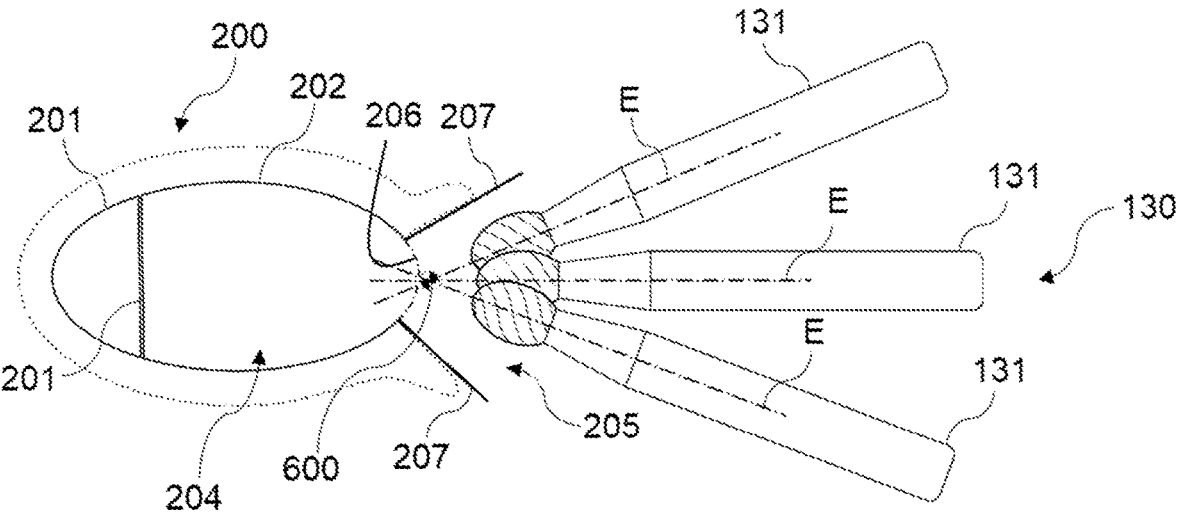
FIGS. 27a to 27d illustrate, schematically, several phases a planned treatment which can be performed thanks to the computer-assisted surgery system, such planned treatment being a minimally invasive surgical treatment.
Figure 27B:
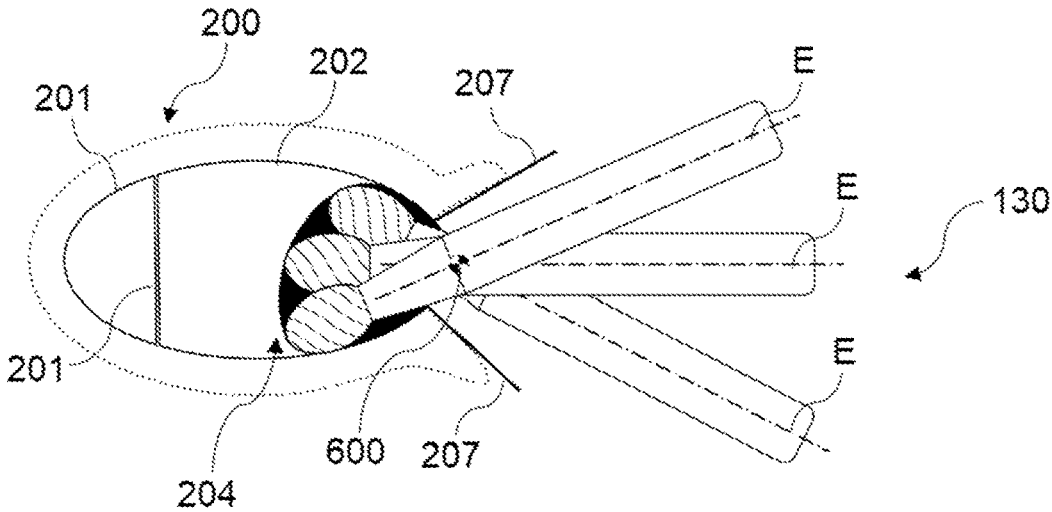
Figure 27C:
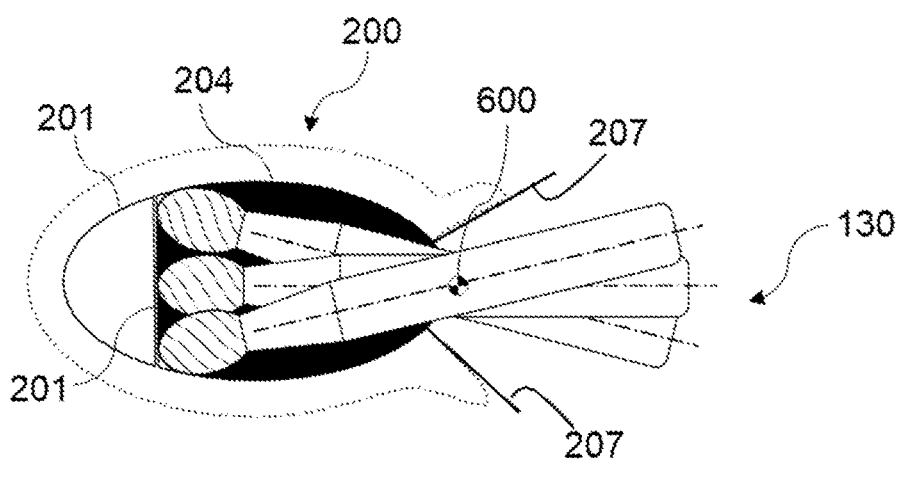
Figure 27D:
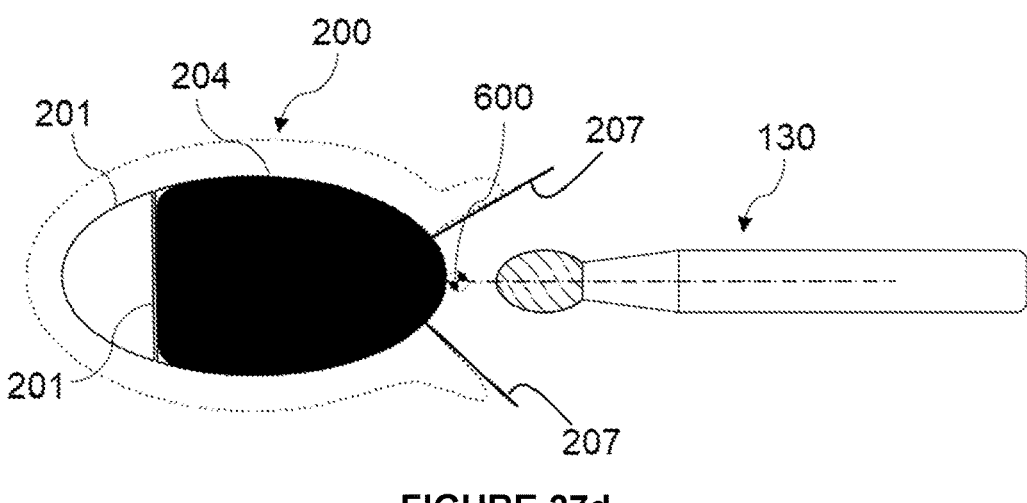

FIGS. 27a to 27d are more particularly representations of successive phases of the planned treatment which consist in a tibial osteotomy similar to the one described with reference to FIGS. 24 and 25. FIG. 27a thus illustrates a first phase wherein the surgical tool 130 is positioned, thanks to the pre-operative mode of the computer-assisted surgery system detailed below, near the entry boundary 206. When the pre-operative mode is enabled, the control unit is adapted to compute instructions so as to ensure that the surgical tool does not cross such entry boundary. As the control unit has defined the surgical tool access path 205 thanks to the protective boundaries 207, the user is constrained, when the operative mode is enabled, to enter the region of interest 204, by crossing the entry boundary 206, through such surgical tool access path 205, as shown on FIG. 27b. Once within the region of interest 204, the user is allowed to displace the surgical tool 130 with respect to the pivot point 600 described above. Such pivot point 600 is fixed with respect to the anatomical structure 200. FIG. 27c illustrates a third phase of the planned treatment wherein a bigger part of the region of interest has been removed and FIG. 27d illustrates a final phase of such planned treatment wherein the entirety of the region of interest 204 has been removed and wherein the surgical tool 130 is removed from the region of interest 204. The combination of boundaries and pivot point used by the control unit to cover the region of interest whilst protecting some tissues make the surgical tool displacement requested through user inputs, extremely easy and safe to achieve with little dexterity needed. The protective boundaries 207 which define the surgical tool access path 205 here ensure that the user does not damage the surroundings of the anatomical structure 200 during the insertion of the surgical tool 130, during the performing of the planned treatment, nor during the removal of said surgical tool 130 from the region of interest 204.

All these different boundaries can for instance be displayed on the human-machine interface previously mentioned. For instance, according to the computed position of such boundaries, the control unit can be adapted to display, on the human-machine interface, an image of the anatomical structure to be treated wherein part(s) of the region of interest on which the planned treatment has already been performed is/are displayed in a first color, wherein part(s) of the region of interest on which the planned treatment remains to be performed is/are displayed in a second color different from the first color, and wherein the region to avoid is displayed in a third color different from the two other colors. Similarly, a region of non-cutting tool to boundary conflict preventing user requested surgical tool displacement can be displayed in yet another color to facilitate the understanding of the inter-active behavior of the control unit. For instance, if the tool is an oscillating saw blade, the human-machine interface can be adapted to display a maximal excursion of the saw blade as a cone during its oscillations. Obviously, this is only a few examples of the information that can be displayed on such human-machine interface and more or less information could be displayed on such human-machine interface within the scope of the invention.

The control unit can be provided with the position of at least one environmental obstacle. The words "environmental obstacle" here refer to an obstacle present in the vicinity of the computer-assisted surgery system of the invention. The control unit 300 can thus be adapted to consider such environmental obstacle in the computing of the instructions to be sent to the motorized joint(s) and to compute said instructions so as to prevent any collision between the surgical tool 130 and such environmental obstacle and also between the robotic arm 110 and said environmental obstacle. As examples of such environmental obstacles, we can cite the markers of the localization unit, a surgery table, any wire present in the operating room, some parts of the patients or safety zones for the practitioners. Obviously, those are only examples of such environmental obstacles and many more of them could be considered by the control unit 300 within the scope of the invention.

According to the invention, the user can also define an enlarged region of interest which corresponds to a part of a region to avoid wherein the user is nevertheless able to perform part of the treatment if he/she requests it. For instance, if something unexpected happens during the surgery that necessitates to perform part of the treatment in the region defined as the "region to avoid", the user can indicate, during said treatment, that he/she wishes to use the surgical tool outside the region of interest, that is to say in the region to avoid. In such case, the system is adapted to authorize the surgical tool to enter the region of avoid, that is to say to override the static boundaries of the region of interest.

Optionally, this overriding of the static boundaries can be associated with the computing of a more stringent working range. For instance, the maximum working speed of the surgical tool, or the maximum displacement speed of such surgical tool can be lowered in such enlarged region of interest. This situation could occur for example if a surgical planning step has defined a bony target region to cut based on Computed Tomography (CT) images, registered such bony target with the tracker attached to the anatomical structure, and if osteophytes were missed on the CT images during image segmentation procedures. Indeed, in such a situation, the user needs to cut said osteophytes, even if they do not appear on the CT images. When he/she sees such osteophytes, the user can thus indicate to the system that he/she needs to override the static boundary. More generally if the segmentation of images has underdefined a target area which is defined as the safe area to be cut for any reason, then the user can define such enlarged region so as to permit to cut all necessary parts of the anatomical structure.

Referring back to FIG. 22, the method of the invention can comprise an additional step S'1 of 3D-modelization of the anatomical structure on which the treatment must be performed. This 3D-modelization can be realized according to at least two different methods described below. Especially, the additional step S'1 can comprise at least a first sub-step during which the 3D-model is acquired as described hereunder, at least a second sub-step wherein the 3D-model is recorded in the storage medium 170 and at least a third sub-step of calibration of the 3D-model of the anatomical structure, that is to say matching said 3D-model with the real anatomical structure to be treated. These first, second and third sub-steps can be realized one after the other or simultaneously, without departing from the scope of the invention.

According to the invention, the 3D-modelization of the anatomical structure can be realized by acquiring images of said anatomical structure, thanks to any known imaging system, such as X-ray, MRI, computed tomography, cone beam computed tomography etc. Alternately, the 3D-modelization of the anatomical structure can be realized thanks to a tracked palpation probe and an associated software. According to this alternative, the user U of the computer-assisted surgery system first has to palpate an accessible surface of the anatomical structure with the tracked palpation probe, thus creating a virtual representation of such accessible surface. The associated software is then adapted to superimpose the information collected thanks to the palpation of the accessible surface of the anatomical structure with some recorded information of a standard 3D-model of such anatomical structure, in order to re-create the 3D-model of said anatomical structure. Regardless the way the 3D-modelization is realized, this first sub-step can be followed by the second sub-step of calibration. This second sub-step aims to match the 3D-model obtained with the real position of the anatomical structure, that is to say to transform such 3D-model into a patient-related coordinate system. Alternately, the first sub-step and the second sub-step can be realized simultaneously. The obtained 3D-model can then for instance be displayed on a human-machine interface of the system.

Optionally, the additional step S'1 of the method can comprise a fourth sub-step of determining the different parts constitutive of the anatomical structure based on the acquired 3D-model. This fourth sub-step can for instance be done, at least partially, manually by the user U who must indicate, for instance on the human-machine interface displaying the 3D-model, the different parts which constitute the anatomical structure. Alternately or concurrently, this fourth sub-step can be realized, at least partially, automatically by the control unit 300. Those information are also recorded in the storage media 170, as constraints related to the surgical plan. Referring back to the example of the osteotomy, the control unit 300 can for instance be adapted to determine which parts of the acquired 3D-model represent cortical bones, which parts of this 3D-model represent soft bones, which parts of this 3D-model represent periosteum, which parts of this 3D-model represent cartilages, and which part of this 3D-model represent soft tissues. Obviously, those are only examples of the kind of anatomical structures which can be identified which does not restrict the invention. The control unit 300 is adapted to consider the corresponding information in the computing of the instructions to be sent to the motorized joints. For instance, the control unit 300 can be adapted to regulate the working speed of the surgical tool based on such information, the working speed being, for instance, slower in the soft bones than in the cortical bones. Also, the control unit 300 can be adapted to consider the periosteum, the cartilages and/or the soft tissues as regions to avoid, thus preventing any damage to such periosteum, cartilages and/or soft tissues. Obviously, this is only an example, and the control unit 300 could be adapted to consider periosteum, the cartilages and/or the soft tissues as the region of interest while the bones would be considered as a region to avoid, depending on the treatment to be performed. For instance, the method of the invention can be used to help the user performing a joint prosthesis implantation, such treatment requiring the removing of at least some of the cartilages of the concerned joint.

Obviously, the third sub-step and the fourth sub-step of the additional step S'1 of the method can be realized in any order, or they even can be realized simultaneously without departing from the scope of the invention.

As previously mentioned, the static boundary defined based on the region of interest and the dynamic boundary are set and, optionally modified, by the control unit. Therefore, the control unit can comprise at least one software adapted to analyze said 3D-model of the anatomical structure and to determine which parts of such anatomical structure are to be removed.

As previously mentioned, the computer-assisted surgery system of the invention can be operated according to at least three different modes, all aiming to help the user to perform the planned treatment. The system can thus comprise a mode selector through which the user can select one of the modes. The mode selector can be connected to the handle to transmit the information related to the selected mode. This connection can be realized thanks to a wire or it can be wireless within the scope of the invention. This mode selector can be integrated in the control unit 300 or it can be formed as a switch which can be arranged on the robotic arm, preferably on the end-effector of such robotic arm. Alternately, this mode selector can be formed on the handle. In a particular embodiment of the invention, the manually activated device previously described can be used as this mode selector. Obviously, this is only one example and the mode selector could be realized differently, for instance, by a voice command, without departing from the scope of the invention. Optionally, the system of the invention can be provided with a light-emitting device adapted to emit light of different colors, depending on the mode selected by the user. Depending on the mode selected by the user, the control unit 300 is thus adapted to ignore some of the inputs in the computing of the instructions.

For instance, the user can first select the collaborative mode. As mentioned above, in the collaborative mode, the user is allowed to control the movements of the robotic arm, by providing to the control unit inputs in the form of measured displacements applied to the movable part of the handle while the surgical tool is deactivated. In this collaborative mode, the control unit is adapted to compute instruction(s) to be sent to the motorized joint(s) based on the intended direction of displacement determined based on the measured displacement. Optionally, the control unit can be adapted to compute instruction(s) to ensure that the surgical tool remains outside a defined region to avoid. Additionally, when the collaborative mode is selected, the surgical tool is deactivated. In other words, the working range computed by the control unit is, when such collaborative mode is selected, define to set the maximum working speed of the surgical tool to zero.

In order to displace the robotic arm through the displacement applied on the handle movable part, such handle preferably encompasses at least six degrees of freedom.

Therefore, the collaborative mode permits to the user to move the motorized joints of the robotic arm, in order to position it as he/she wishes, as long as the intended movement does not result in introducing the surgical tool or the robotic arm in a prohibited area. This collaborative mode can for instance be used at the beginning of the treatment to approximately position the robotic arm 110 in a way permitting to perform the planned treatment, or at least part of this planned treatment. The collaborative mode can also be selected later during the treatment, in order to make the anatomical structure 200 easier to reach. Optionally, when the collaborative mode is selected, the activation mechanism 180 can be deactivated, thus locking the surgical tool 130 in a non-operative position. Such locking forms an extra security system to prevent any unwanted treatment during this approximative positioning step. Alternately, when the collaborative mode is selected, the activation mechanism 180 can be used to control the displacement speed of the robotic arm.

Once the robotic arm is near the region of interest, the user might select the pre-operative mode. The pre-operative mode aims to align the surgical tool 130 with the region of interest. Especially, the pre-operative mode aims to align the main axis of extension of the surgical tool with at least one working direction of the surgical tool within the region of interest, such working direction being defined as a direction along which at least part of the planned treatment can be performed. When the system is set to this pre-operative mode, the displacement sensors of the handle can be deactivated. According to this pre-operative mode, the control unit 300 is adapted to compute instructions 301 to be sent to the motorized joint(s) based on the surgical plan and on the relative position and orientation of the surgical tool with respect to the anatomical structure. The computed instruction 301 thus causes a movement of the robotic arm 110 which permits to align the surgical tool 130 with the recorded region of interest, that is to say wherein the treatment must be performed. Not considering the measured displacement in the computing of the instruction, thus prevents any unwanted action from being performed as long as the surgical tool is not aligned with the region of interest. When the pre-operative mode is selected, the control unit is adapted to compute instruction(s) so as to ensure that the surgical tool does not cross the entry boundary.

Once the surgical tool is in the wanted position, the user U can select the operative mode. Optionally, the control unit 300 can be configured to ignore the selection of the operative mode as long as localization unit 250 indicates that the surgical tool is not aligned with the region of interest. This ensures that the surgical tool can only be activated when it is ready to cross the entry boundary of the region of interest. Advantageously, the control unit 300 can be adapted to not consider measured displacement in the computing of the instructions if it receives an information, from the localization unit, according to which the surgical tool exits the region of interest. Obviously, these are only example of the security considerations that can be implemented in the system of the invention.

When the operative mode is activated, the control unit 300 is configured to continuously compute instructions to be given to the motorized joint(s), in order to perform the planned treatment. When this operative mode is selected, the user U exerts a displacement on the handle movable part which is detected and measured thanks to the displacement sensors. Simultaneously, the user U uses, or not, the activation mechanism 180 which is adapted to consequently transmit an information related to the activation of the surgical tool and to at least one working parameter of this surgical tool, such as its working speed, to the control unit 300.

As the handle 140 is used both during the collaborative mode and the operative mode, the selection of the operative mode can result in a modification of the set of operative degrees of freedom considered by the control unit 300 in the computing of the instructions to be sent to the motorized joint(s). As detailed below, the user might need six degrees of freedom to position the robotic arm when the collaborative mode is selected, but only a few degrees of freedom to perform the planned treatment when the operative mode is selected. Such planned treatment can thus be divided in at least a first phase corresponding to the collaborative mode wherein the user needs all six degrees of freedom and in at least a second phase corresponding to the operative mode wherein the user needs a smaller number of degrees of freedom. The computer-assisted surgery system of the invention can be used during both these phases by enabling the user U, or the control unit 300, to modify the set of degrees of freedom considered by such control unit 300. Advantageously, the set of degrees of freedom considered by the control unit 300 can be modified at any time during the course of the planned treatment, even during a single phase of such planned treatment. More details are given about this below.

Based on all previously cited inputs, the control unit 300 is adapted to compute and send instruction(s) 301 to the motorized joint(s), the execution of such instruction(s) resulting in a displacement of the surgical tool in a direction which includes the intended direction of the displacement determined based on the measured displacement transmitted by the displacement sensors of the handle as one of its components.

As previously described, the control unit can be adapted to modify the user's inputs transmitted through the measured displacement of the handle movable part, with the constraints of the surgical plan and with the provided relative position and orientation of the surgical tool with respect to the anatomical structure, in order to provide the motorized joints with instruction(s) permitting to perform the planned treatment with more accuracy and more sensibility than if the same planned treatment was performed only by the user.

Figure 29:
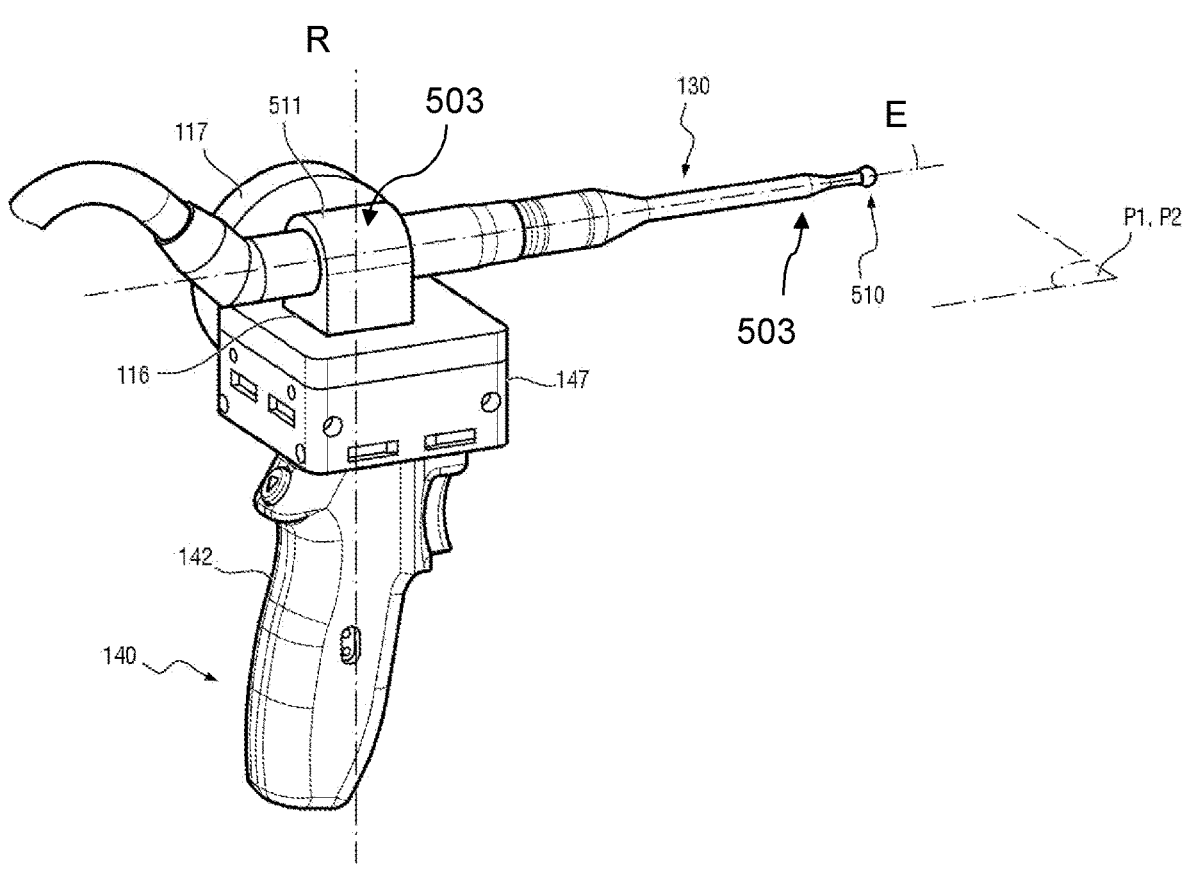
Figure 30:
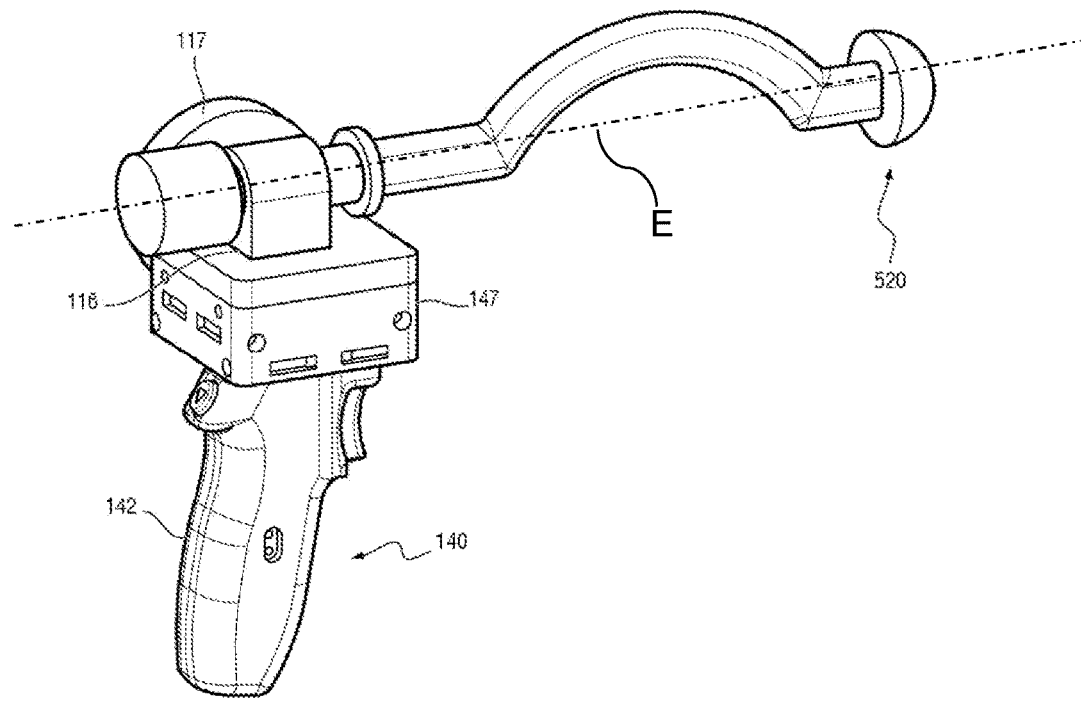

With reference to FIGS. 28 to 30, we are now going to describe different applications of the system 100 of the invention. Obviously, those are only examples and other applications can be considered within the scope of the invention.

According to a first example of application of the invention, the planned treatment can be to realize a cutting within a predefined cutting plane and with a surgical saw, said predefined cutting plane thus forming the region of interest. This kind of treatment requests only movements within one plane and may typically be restricted to a partial surface of the anatomical structure or a contour of such anatomical structure. Consequently, once the operative mode is activated, the handle's movable part is configured to have only three degrees of freedom, upon which two translational degrees of freedom and one rotational degree of freedom, additionally to the activation mechanism adapted to control the working parameters of the surgical tool. At least one of the translational degrees of freedom can be parallel to the main axis of extension E of the surgical saw.

An example of such a surgical saw 500 is for instance illustrated on FIG. 28 which is a perspective view of the handle 140 of the invention associated with such surgical saw 500. As shown, this surgical saw 500 comprises a power tool 501 adapted to drive a saw blade which encompasses a cutting part 502, the power tool 501 being adapted to be fixed, directly or indirectly, to the flange 117 of the robotic arm and the cutting part 502 being adapted to perform the planned treatment. According to the illustrated embodiment, the surgical saw 500 and the handle 140 are fixed to the support 116, itself fixed to the flange 117. The surgical saw 500 illustrated is an oscillating surgical saw 500 which must oscillate in order to perform the cut. Such surgical saw 500 thus presents an axis of rotation R, R', R" around which said surgical saw 500 is adapted to oscillate. As detailed below, this axis of rotation R, R', R" can be displaced, by the control unit or by the user, during the course of the treatment to provide the user the most ergonomic system at any time of such treatment. Obviously, this is only an example of the kind of surgical saw 500 that can be used, and any other surgical saw could be used without departing from the scope of the invention. As mentioned above, the surgical saw 500 mainly extends in the second plane P2 which is parallel to the first plane P1 which includes the first and second directions along which the movable part is adapted to be displaced. This second plane P2 can also be coincident with the plane in which the treatment is to be performed, thus improving the ergonomics of the system. As illustrated, the axis of rotation R of the surgical saw 500 is perpendicular to such second plane P2. This axis of rotation R, R', R" passes through the tool center point 503, 503', 503" and both of them can be modified as the planned treatment is performed.

According to this first example of application, the planned treatment can thus comprise a first phase wherein the collaborative mode is enabled and during which the user needs the six degrees of freedom to position the robotic arm in close proximity with the region of interest as defined for the next phase of the planned treatment, and consequently the surgical tool held by such robotic arm, near such region of interest and a second phase wherein the operative mode is enabled and during which the user needs only three of those degrees of freedom. As previously mentioned, the method of the invention permits to modify the set of degrees of freedom considered by the control unit in its calculation of the instructions, and especially to deactivate three of the six degrees of freedom according to the first example, thus allowing him to perform both phases of said planned treatment with the same handle and with the same computer-assisted surgery system.

As mentioned, the axis of rotation R, R', R" and the tool center point 503, 503', 503" can also be modified automatically by the control unit. For instance, the tool center point 503' can be positioned as a point of the handle's main axis of extension during the first phase of the planned treatment, that is to say near the second end of the robotic arm, and the tool center point 503 can be displaced so as to be positioned on the power tool 501 of the surgical saw 500 during the second phase of this planned treatment, that is to say, closer to this cutting portion 502 of the surgical saw. As schematically shown on FIG. 28, the tool center point 503" can also be displaced near the cutting part 502 of the oscillating saw 500. Regardless its position, the tool center point 503, 503', 503" is always crossed by the current axis of rotation R, R', R" of the surgical saw 500. In other words, the axis of rotation R, R', R" of the surgical saw 500 is formed as an axis, perpendicular to the second plane P2 in which the surgical saw 500 mainly extends, and which crosses the tool center point 503, 503', 503" as defined above. This characteristic also participates to the user-friendliness of the system. Indeed, during the first phase described above, the user controls the robotic arm as a whole, in order to position the surgical tool near the region of interest while during the second phase the user needs to control more particularly the movements of the surgical tool to perform the planned treatment, whether that be an extremity of the surgical tool, such as a surgical tool tip or any other part of the surgical tool. Therefore, the positioning of the tool center point near the second end of the robotic arm is advantageous during said first phase while the positioning of the tool center point near the surgical saw, or near the cutting part 502 of such oscillating saw 500 is advantageous during the second phase to facilitate contouring cuts. By "advantageous", we here mean that the corresponding positioning of the tool center point aims to provide the user the sensation that he/she is actually displacing the corresponding portion of the object as if he/she was directly holding it in her/his own hands while he may actually monitor its displacement hidden from sight, on a remote navigation display.

FIG. 28b is illustrates an assembly of the surgical tool 130, realized according to the first example of application which has just been described, with the handle 140 attached to the robotic arm 110 of the system. FIG. 28b is thus illustrates an embodiment of the invention, wherein the handle 140 is directly attached to the surgical tool 130, thus improving the ergonomics of the system. Especially, the surgical tool 130 is attached to the fixing part of the handle 140. The assembly formed by the surgical tool 130 and the handle fixing part is itself attached to the robotic arm 110 and form the end-effector 115 of such robotic arm 110. As previously mentioned, the handle fixing part and the surgical tool 130 could also be attached to different segments 118 of the robotic arm 110.

Finally, FIG. 28b is illustrates an example of the degrees of freedom that can be controlled through the displacement of the handle movable part, namely a first translational degree of freedom corresponding to the displacements applied along the D1 direction described above, a second translational degree of freedom corresponding to the displacements applied along the D2 direction described above and the rotational degree of freedom.

According to a second example of application of the invention, the planned treatment can be removing a certain volume of a bone thanks to a burr. This kind of treatment requests movements along up to five degrees of freedom. Consequently, once the operative mode is activated, the handle's movable part is configured to drive five of the six degrees of freedom, the rotation of the burr being regulated thanks to the activation mechanism. As mentioned, above, the handle's movable part can comprise up to six degrees of freedom. When such a handle's movable part is used, the selection of the operative mode results in the deactivation of one of the six degrees of freedom. In this way, when the control unit determines the intended direction of displacement of the surgical tool, it only considers the five useful degrees of freedom. The deactivated degree of freedom, in this case, corresponds to a rotational degree of freedom which is, in fact, the same degree of freedom around which the surgical tool works, since said burr is mounted on a drill and adapted to rotate around its own main axis of extension E as illustrated on FIG. 29. As a result, this sixth degree of freedom could optionally remain activated in the handle movable part without departing from the scope of the invention.

The surgical burr is for instance illustrated on FIG. 29 which is a representation, in a perspective view, of such a surgical burr 510. Especially, FIG. 29 illustrates the surgical burr 510 mounted on the handle 140. According to this illustrated embodiment, the end-effector does not comprise the support earlier mentioned, the handle 140 and the surgical tool 130 being directly fixed to the flange formed by the second end 112 of the robotic arm. As shown, the surgical burr 510 is more particularly fixed on the top part 147 of the handle's housing 142. To this goal, the top part 147 of the handle's housing 142 is provided with a fixing device 511 adapted to receive said surgical burr 510. According to the illustrated embodiment, the handle 140 present the "pistol grip" shape described above with reference to FIG. 18. The main axis of extension X of the handle 140 is thus secant with the main axis of extension E of the surgical burr 510.

Especially, according to this second example of application, the surgical tool 130 comprises a power tool 501 adapted to drive a tool, here realized as the burr 510.

Again, the tool center point 503, 503' can be modified depending on the ongoing phase of the planned treatment. According to this second example of application, the volume to be removed can be reached through a small incision. In this case, the planned treatment can be divided in a first phase wherein the burr has to be inserted in the patient's body and in a second phase wherein the concerned volume is removed. In this particular example, it can thus be extremely useful to be able to modify the tool center point between the first phase and the second phase to match such tool center point with the pivot point previously described, so as to improve the accuracy of the displacement requested by the user of the system. In a similar way to what have been described above referring to the first and the second examples of application of the invention, the tool center point 503 can be positioned near the second end of the robotic arm during the first phase while the tool center point 503' can be positioned nearer the surgical tool during the second phase. As illustrated, the axis of rotation R, R' of the surgical tool 130 is displaced so as to always cross the tool center point 503, 503'.

According to this second example of application, the computer-assisted surgery system can be used in spine surgery, for instance to perform the milling of a bone using the burr as the surgical tool, or any surgical tool that can burr a bone such as ultrasonic devices during a minimally invasive procedure for canal decompression for example. In this case, a set of three operative degrees of freedom is selected, by the user or by the control unit so as to permit the user to perform the planned treatment while preserving the constraint of having a fixed entry point on the skin. In such case, the static boundary can be defined as a part of the bone segmented on 3D images that needs to be removed, thus preventing the burr to go in areas that must be avoided, including, but not limited to, the spinal canal.

According to a third example of application, not illustrated here, the planned treatment can be drilling a hole into a bone. According to this second example of application, the surgical tool can for instance be a drill bit. This kind of treatment requests only movements along one direction. Consequently, once the operative mode is activated, the handle's movable part is configured to have only one degree of freedom, and especially, a translational degree of freedom, additionally to the activation mechanism adapted to control the working parameter(s) of the surgical tool. As mentioned, above, the handle's movable part comprises at least three degrees of freedom. When the handle movable part used comprises three degrees of freedom, the selection of the operative mode results, according to the second example of application, in the deactivation of two of the three degrees of freedom. As a result, the control unit is adapted to consider only the movements applied along the remaining degree of freedom in the computing of the instruction. In this way, when the control unit determine the intended direction of displacement of the surgical tool based on the measured displacement, it only considers the only useful degree of freedom of said intended direction, thus preventing, or at least limiting the chances, that the robotic arm is moved in a forbidden direction, that is to say a direction resulting in the surgical tool being taken out of the region of interest.

The handle movable part can comprise six degrees of freedom. According to the second example of application, the planned treatment can thus comprise a first phase during which the user needs the six degrees of freedom to position the surgical tool held by the robotic arm, near the region of interest and a second phase during which the user needs only one of those degrees of freedom. As previously mentioned, the system of the invention permits to modify the set of degrees of freedom considered by the control unit in the computing of the instructions, and especially to deactivate all but one of the degrees of freedom, thus allowing the user to perform both phases of said planned treatment with the same handle and with the same computer-assisted surgery system.

In a similar way to what has been described above with reference to FIG. 29, the tool center point can be positioned near the second end of the robotic arm during the first phase of the planned treatment and this tool center point can be displaced to be positioned closer to the drill bit during the second phase. Also, the axis of rotation of the surgical tool is defined so as to cross such tool center point.

According to this third example of application, the computer-assisted surgery system of the invention can also be used to perform the drilling of an axis in a vertebra, using only one of the degrees of freedom of the handle movable part to displace the drill bit. It can be also used for drilling a tunnel or placing a K-wire for many interventions for knee anterior cruciate ligament surgery, shoulder glenoid axis targeting, placement of screws inside bones such that screws do not go outside bones, placement of screws to lock the distal part of a traumatology nail, placement of several screws inside a femoral neck for fixation of a femoral neck fracture such that all screws do not exit the femoral head or the femoral neck and do not intersect, or the like.

According to a fourth example of application of the invention, the planned treatment can be inserting a femoral prothesis within an acetabulum. The planned treatment can be divided into two phases. A first phase resulting in milling the acetabulum and a second phase resulting in inserting the femoral prothesis. The milling of the acetabulum can be realized thanks to a reamer while the insertion of the femoral prothesis can be realized thanks to a femoral head impactor. An example of such femoral head impactor is for instance illustrated, on FIG. 30.

In a similar way to what have been described with reference to FIG. 29, FIG. 30 represents, in a perspective view, a femoral head impactor 520 fixed to the support 116 to which the top part 147 of the handle's housing 142 is also fixed.

Obviously, the features that have just been described in relation with any of the embodiment illustrated can be combined with features described in relation with any other embodiment without departing from the scope of the invention.

It will be understood from the foregoing that the present invention provides an inter-active system adapted to perform surgical treatments with more accuracy and more sensitivity than the systems already known, thus resulting in a better reproducibility of such surgical treatment.

However, the invention cannot be limited to the means and configurations described and illustrated herein, and it also extends to any equivalent means or configurations and to any technically operative combination of such means. In particular, the shape and arrangement of the handle, of the movable part of the handle, of the robotic arm or of the base can be modified insofar as they fulfil the functionalities described in the present document.

The invention claimed is:

1. A computer-assisted surgery system for treating a region of interest of an anatomical structure with a surgical tool according to a surgical plan, comprising:
    a robotic arm comprising at least three motorized joints;
    a surgical tool attached to the robotic arm;
    a handle comprising:
        a fixing part attached to the robotic arm in a fixed position relative to the surgical tool, and
        a movable part mounted on the fixing part so as to be movable relative to the fixing part according to at least three degrees of freedom,
    at least one activation mechanism configured to control at least one working parameter of the surgical tool;
    a localization unit comprising at least one first tracker configured to be coupled to the surgical tool and at least one second tracker configured to be coupled to the anatomical structure defining a reference frame of the patient, the localization unit being configured to determine in real time a position and orientation of the surgical tool in the reference frame of the patient; and
    a control unit configured to send instructions to at least one motorized joint to move the robotic arm,
    the computer-assisted surgery system being operable in an operative mode allowing a user to control movements of the surgical tool by providing to the control unit inputs in the form of measured displacements of the movable part with respect to the fixing part applied by the user to the movable part of the handle while treating the region of interest with the surgical tool,
    wherein the control unit is configured to, as long as the operative mode is enabled:
        enable motion of the surgical tool with respect to the anatomical structure only if a user moves the movable part of the handle, receive the measured displacement of the movable part with respect to the fixing part of the handle,
based on said measured displacement, determine an intended direction of displacement along which the user wants the surgical tool to be displaced and a requested displacement speed,
receive from the localization unit the position and orientation of the surgical tool in the reference frame of the patient,
based on the intended direction of displacement of the surgical tool, on the requested displacement speed, on the surgical plan and on the position and orientation of the surgical tool in the reference frame of the patient, compute an optimal trajectory and an optimal displacement speed of the surgical tool and compute at least one instruction to be sent to at least one of the motorized joints to move the robotic arm to operate the surgical tool according to the optimal trajectory and optimal displacement speed, and
send the computed instruction to at least one of the motorized joints.

2. The system of claim 1, wherein a reference frame To is attached to the surgical tool, wherein a reference frame BJ is attached to the handle fixing part, the reference frame To and the reference frame BJ being related to each other by a transform matrix determined by the user and/or by the control unit.

3. The system of claim 2, wherein the reference frame To is defined by at least three axes, wherein the reference frame BJ is defined by at least three axes, the transform matrix being determined such that the three axes defining the reference frame To and the three axes defining the reference frame BJ are parallel, two by two.

4. The system of claim 2, wherein the surgical tool comprises an immaterial tool center point which forms an origin of the reference frame To.

5. The system of claim 4, wherein the control unit is configured to modify the immaterial tool center point during the course of the treatment.

6. The system of claim 2, wherein the transform matrix relating the reference frame attached to the surgical tool to the reference frame attached to the handle fixing part is different between a first phase of the planned treatment and a second phase of the planned treatment.

7. The system of claim 1, wherein the activation mechanism is configured to control the requested displacement speed of the robotic arm.

8. The system of claim 1, wherein the control unit is configured to, as long as the operative mode is enabled:
    based on the measured displacement, on the surgical plan and on the position and orientation of the surgical tool in the reference frame of the patient, compute a working range and limit the at least one working parameter of the surgical tool to remain within the computed working range.

9. The system of claim 8, wherein the computed working range is defined by one or several of the following parameters:
    a maximum displacement speed of the surgical tool,
    a minimum displacement speed of the surgical tool,
    a maximum working speed of the surgical tool, and
    a minimum working speed of the surgical tool.

10. The system of claim 1, wherein the control unit or the user sets one of a static boundary or a dynamic boundary, wherein the static boundary is based on the region of interest, the control unit being configured to compute instructions so as to prevent the surgical tool from crossing the static boundary, and wherein the control unit being configured to modify the dynamic boundary during the course of the treatment and the control unit being configured to compute instructions so as to prevent the surgical tool from crossing the dynamic boundary.

11. The system of claim 10, wherein the control unit is configured to reduce a displacement speed of the surgical tool to zero along at least one direction as the surgical tool reaches the static boundary or the dynamic boundary so as to prevent the surgical tool from crossing, respectively, the static boundary or the dynamic boundary.

12. The system of claim 10, wherein when the surgical tool reaches the static boundary or the dynamic boundary, the optimal trajectory is defined so as for the surgical tool to be displaced along the static boundary or along the dynamic boundary.

13. The system of claim 10, wherein the dynamic boundary is set, by the control unit, to prevent the surgical tool to be operated three times at a same location of the region of interest.

14. The system of claim 10, wherein the dynamic boundary is set, by the control unit, so as for the displacements of the robotic arm to be coherent with the attainability of the surgical tool.

15. The system of claim 10, wherein the user defines an extended region of interest, the extended region of interest extending beyond the static boundary.

16. The system of claim 15, wherein the control unit is configured to compute a more stringent working range in the extended region of interest than in the region of interest.

17. The system of claim 1, wherein the control unit or the user sets an entry boundary, based on the region of interest, the entry boundary forming an access zone to the region of interest, the control unit being configured to compute instruction(s) so as for the surgical tool to cross the entry boundary to reach the region of interest.

18. The system of claim 17, wherein the surgical plan comprises a surgical tool access path constraint and wherein the control unit is configured to compute instruction(s) so as for the surgical tool to be displaced within the surgical tool access path for reaching the region of interest, the surgical tool access path being defined by at least the entry boundary and by at least one protective boundary set by the control unit or by the user.

19. The system of claim 1, wherein the control unit is configured to detect a vibration applied on the handle movable part and to filter the detected vibration when computing the instruction(s) to be sent to the motorized joint(s).

20. The system of claim 1, wherein the handle movable part comprises at least one translational degree of freedom, and wherein the at least one translational degree of freedom is parallel to a main axis of extension of the surgical tool.

21. The system of claim 1, further comprising a detecting device configured to detect that the handle is held by a hand of a user, the control unit being configured to enable movement of the surgical tool only if the handle is held by the hand of the user, as long as the operative mode is enabled.

22. The system of claim 1, wherein the handle comprises at least three displacement sensors, each displacement sensor being configured to detect and measure the displacements of the movable part according to at least one respective degree of freedom, and wherein at least two of the displacement sensors are configured to redundantly detect and measure displacements of the movable part according to at least one same degree of freedom.

23. The system of claim 1, wherein the handle is shaped as a pistol grip and wherein an angle formed between a main axis of extension of the handle and a main axis of extension of the surgical tool is greater or equal to 30°.

24. The system of claim 1, wherein a main axis of extension of the handle is aligned with a main axis of extension of the surgical tool.

25. The system of claim 24, wherein the surgical tool is attached to the robotic arm by a shaft and wherein the handle surrounds, at least partially, the shaft of the surgical tool.

26. The system of claim 1, wherein the system is operable in a collaborative mode allowing the user to control movement of the robotic arm by providing to the control unit inputs in the form of measured displacements applied to the movable part of the handle while the surgical tool is deactivated, wherein the control unit is configured to, as long as the collaborative mode is enabled:

receive the measured displacement of the movable part of the handle, determine, based on the measured displacement, an intended direction of displacement, compute at least one instruction to be sent to at least one of the motorized joints to move the robotic arm according to the intended direction of displacement; and send the computed instruction to at least one of the motorized joints.

27. The system of claim 26, wherein the control unit is configured to select a first set of degrees of freedom during a first phase of the treatment and wherein the control unit is configured to select a second set of degrees of freedom during a second phase of the treatment, distinct from the first set of degrees of freedom.

28. The system of claim 27, wherein the system is configured to be operated according to the collaborative mode during the first phase of the treatment and configured to be operated according to the operative mode during the second phase of the treatment.

29. The system of claim 1, wherein the system is operable in a pre-operative mode allowing the control unit to control movement of the robotic arm while the surgical tool is deactivated, wherein the control unit is configured to, as long as the pre-operative mode is enabled:

receive from the localization unit the position and orientation of the surgical tool in the reference frame of the patient, based on the surgical plan and on the relative position and orientation of the surgical tool with respect to the anatomical structure, compute at least one instruction to be sent to at least one of the motorized joints to move the robotic arm to position the surgical tool so as for a main axis of extension of the surgical tool to be aligned with at least one planned working direction within the region of interest, and send the computed instruction to at least one of the motorized joints.

30. The system of claim 1, wherein the region of interest is formed as an infinite plane.

31. The system of claim 1, wherein the region of interest is formed as a planar portion of the anatomical structure.

* * * * *